United States Patent
Ji et al.

(10) Patent No.: US 11,958,906 B2
(45) Date of Patent: Apr. 16, 2024

(54) PHARMACEUTICAL COMPOSITIONS OF MOSUNETUZUMAB AND METHODS OF USE

(71) Applicant: Genentech, Inc., South San Francisco, CA (US)

(72) Inventors: Junyan A. Ji, Foster City, CA (US); Jacqueline Yvonne Tyler, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 18/300,064

(22) Filed: Apr. 13, 2023

(65) Prior Publication Data

US 2023/0331861 A1    Oct. 19, 2023

Related U.S. Application Data

(60) Provisional application No. 63/330,721, filed on Apr. 13, 2022.

(51) Int. Cl.
| | | |
|---|---|---|
| A61K 39/395 | (2006.01) |
| A61K 9/08 | (2006.01) |
| A61K 47/10 | (2017.01) |
| A61K 47/20 | (2006.01) |
| A61K 47/22 | (2006.01) |
| A61K 47/26 | (2006.01) |
| C07K 16/28 | (2006.01) |

(52) U.S. Cl.
CPC ............ *C07K 16/2887* (2013.01); *A61K 9/08* (2013.01); *A61K 47/10* (2013.01); *A61K 47/20* (2013.01); *A61K 47/22* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 7,612,181 B2 | 11/2009 | Wu et al. | |
| 8,258,268 B2 | 9/2012 | Wu et al. | |
| 8,613,919 B1 | 12/2013 | Ma et al. | |
| 8,722,859 B2 | 5/2014 | Miller et al. | |
| 9,011,864 B2 | 4/2015 | Schulz et al. | |
| 10,174,142 B2 | 1/2019 | Savatsky et al. | |
| 11,466,094 B2 | 10/2022 | Chu et al. | |
| 2006/0088523 A1* | 4/2006 | Andya .................... | A61K 47/26 424/133.1 |
| 2011/0171125 A1 | 7/2011 | Elkins et al. | |
| 2012/0244577 A1 | 9/2012 | Dixit et al. | |
| 2013/0150558 A1 | 6/2013 | Williams et al. | |
| 2015/0166661 A1 | 6/2015 | Chen et al. | |
| 2015/0266966 A1 | 9/2015 | Smith et al. | |
| 2015/0284475 A1 | 10/2015 | Zhou et al. | |
| 2016/0000916 A1 | 1/2016 | Crotts et al. | |
| 2016/0145339 A1 | 5/2016 | Zhou et al. | |
| 2016/0368985 A1 | 12/2016 | Hotzel et al. | |
| 2017/0008971 A1 | 1/2017 | Dennis et al. | |
| 2017/0022274 A1 | 1/2017 | Chang et al. | |
| 2020/0231698 A1 | 7/2020 | Fast et al. | |

FOREIGN PATENT DOCUMENTS

| | | | | |
|---|---|---|---|---|
| CN | 102281902 | A | 12/2011 | |
| CN | 106029696 | A | 10/2016 | |
| EP | 2482212 | A1 | 8/2012 | |
| KR | 10-2016-0098464 | A | 8/2016 | |
| RU | 2017105849 | A | 8/2018 | |
| WO | WO-94/04679 | A1 | 3/1994 | |
| WO | WO-2007/146968 | A2 | 12/2007 | |
| WO | WO-2008/119566 | A2 | 10/2008 | |
| WO | WO-2010/057109 | A1 | 5/2010 | |
| WO | WO-2010/081173 | A2 | 7/2010 | |
| WO | WO-2010/114940 | A1 | 10/2010 | |
| WO | WO-2011/090754 | A1 | 7/2011 | |
| WO | WO-2011/143545 | A1 | 11/2011 | |
| WO | WO-2012/075581 | A1 | 6/2012 | |
| WO | WO-2012/123949 | A1 | 9/2012 | |
| WO | WO-2012/162067 | A2 | 11/2012 | |
| WO | WO-2013/128194 | A1 | 9/2013 | |
| WO | WO-2013/163631 | A2 | 10/2013 | |
| WO | WO-2013/192546 | A1 | 12/2013 | |
| WO | WO-2013/192550 | A2 | 12/2013 | |
| WO | WO-2014/083178 | A1 | 6/2014 | |
| WO | WO-2014/107599 | A2 | 7/2014 | |
| WO | WO-2014/108483 | A1 | 7/2014 | |
| WO | WO-2014141152 | A2 * | 9/2014 | ....... A61K 39/39591 |
| WO | WO-2014/170063 | A1 | 10/2014 | |
| WO | WO-2015/013671 | A1 | 1/2015 | |
| WO | WO-2015/095392 | A1 | 6/2015 | |
| WO | WO-2015/143079 | A1 | 9/2015 | |
| WO | WO-2015/184203 | A1 | 12/2015 | |
| WO | WO-2015/184207 | A1 | 12/2015 | |

(Continued)

OTHER PUBLICATIONS

Hossini et al., NPJ Systems Biology and Applications, 2020, vol. 6, p. 1-11.*
Brack et al., "A Bispecific HER2-Targeting FynomAb with Superior Antitumor Activity and Novel Mode of Action," Mol Cancer Ther. 13(8):2030-39 (2014) (11 pages).
Buhmann et al., "Immunotherapy of recurrent B-cell malignancies after allo-SCT with Bi20 (FBTA05), a trifunctional anti-CD3 x anti-CD20 antibody and donor lymphocyte infusion," Bone Marrow Transplant. 43(5):383-97 (2009).
Choi et al., "Bispecific antibodies engage T cells for antitumor immunotherapy," Expert Opin Biol Ther. 11(7):843-53 (2011).

(Continued)

*Primary Examiner* — Yunsoo Kim
(74) *Attorney, Agent, or Firm* — Clark & Elbing LLP; Karen L. Elbing

(57) ABSTRACT

The disclosure provides pharmaceutical compositions comprising mosunetuzumab and methods of using the same.

17 Claims, 14 Drawing Sheets
(13 of 14 Drawing Sheet(s) Filed in Color)
Specification includes a Sequence Listing.

(56) References Cited

FOREIGN PATENT DOCUMENTS

| WO | WO-2016/014942 A1 | 1/2016 |
|---|---|---|
| WO | WO-2016/036678 A1 | 3/2016 |
| WO | WO-2016/081490 A1 | 5/2016 |
| WO | WO-2016/110576 A1 | 7/2016 |
| WO | WO-2016/201300 A1 | 12/2016 |
| WO | WO-2018/093821 A1 | 5/2018 |

OTHER PUBLICATIONS

Diefenbach et al., "An individualized risk mitigation approach for safety: experience from the mosunetuzumab (CD20/CD3 bispecific antibody) development program in relation to neurotoxicity risk," 61st ASH Annual Meeting & Exposition, Dec. 7-10, Orlando, Florida, Poster P-4728 (2019) (1 page).

Donaldson et al., "Design and development of masked therapeutic antibodies to limit off-target effects: application to anti-EGFR antibodies," Cancer Biol Ther. 8(22): 2145-50 (2009).

Drent et al., "A Rational Strategy for Reducing On-Target Off-Tumor Effects of CD38-Chimeric Antigen Receptors by Affinity Optimization," Mol Ther. 25(8):1946-58 (2017).

Haile et al., "Soluble CD80 Restores T Cell Activation and Overcomes Tumor Cell Programmed Death Ligand 1-Mediated Immune Suppression," J Immunol. 191(5):2829-36 (2013) (9 pages).

Hernandez et al., "Pharmacodynamic Effects and Immune Correlates of Response to the CD20/CD3 Bispecific Antibody Mosunetuzumab in Relapsed or Refractory Non-Hodgkin Lymphoma," Blood. 134(Supplement 1):1585 (2019) (4 pages).

"History of Changes for Study: NCT02500407: A Safety, Efficacy and Pharmacokinetic Study of BTCT4465A (Mosunetuzumab) as a Single Agent and Combined With Non-Hodgkin's Lymphoma (NHL) and Chronic Lymphocytic Leukemia (CLL)," ClinicalTrials.gov, last updated Mar. 17, 2022, retrieved Jul. 17, 2023, from <https://classic.clinicaltrials.gov/ct2/history/NCT02500407?V_74=View#StudyPageTop> (10 pages).

Hosseini et al., "Abstract B043: Systems pharmacology modeling of anti-CD20/CD3 T-cell dependent bispecific antibody and its application to clinical trial design," Proceedings of the Second CRI-CIMT-EATI-AACR International Cancer Immunotherapy Conference: Translating Science into Survival; Sep. 25-28; New York, NY. Cancer Immunol Res. 4(11 Suppl):Abstract nr B043 (2016) (4 pages).

Huang et al., "In Vivo Deamidation Characterization of Monoclonal Antibody by LC/MS/MS," Anal Chem. 77(5):1432-9 (2005).

Huang, "Structural chemistry and therapeutic intervention of protein-protein interactions in immune response, human immunodeficiency virus entry, and apoptosis," Pharmacol Ther. 86(3):201-215 (2000).

Igawa et al., "VH/VL interface engineering to promote selective expression and inhibit conformational isomerization of thrombopoietin receptor agonist single-chain diabody," Protein Eng Des Sel. 23(8):667-77 (2010) (11 pages).

Kelley et al., "Thermodynamic Analysis of an Antibody Functional Epitope," Biochemistry. 32(27):6828-35 (1993).

Kiewe et al., "Phase I trial of the trifunctional anti-HER2 x anti-CD3 antibody ertumaxomab in metastatic breast cancer," 2005 ASCO Annual Meeting Proceedings. J Clin Oncol. 23(16S):Abstract 2530 (2005) (1 page).

Kortt et al., "Dimeric and trimeric antibodies: high avidity scFvs for cancer targeting," Biomol Eng. 18:95-108 (2001) (15 pages).

Kuznetzova, E. A., "Brackets in text of legal document as a linguistic and cognitive phenomenon," Vestnik MGOU. Series: Russian Philology. 3:37-42 (2015) (12 pages).

Li et al., "Exposure-response analyses indicate a promising benefit/risk profile of mosunetuzumab in relapsed and refractory non-Hodgkin lymphoma," 61st ASH Annual Meeting & Exposition, Dec. 7-10, 2019, Orlando, Florida. Poster P-1285 (2019) (1 page).

Liu et al., "Affinity-Tuned ErbB2 or EGFR Chimeric Antigen Receptor T Cells Exhibit an Increased Therapeutic Index against Tumors in Mice," Cancer Res. 75(17):3596-607 (2015) (13 pages).

Liu et al., "Heteroantibody duplexes target cells for lysis by cytotoxic T lymphocytes," Proc Natl Acad Sci U S A. 82(24):8648-52 (1985).

Milne et al., "Systematic Analysis of Immune Infiltrates in High-Grade Serous Ovarian Cancer Reveals CD20, FoxP3 and TIA-1 as Positive Prognostic Factors," PLoS One. 4(7):e6412 (2009) (14 pages).

Nishimoto et al., "Toxicity, pharmacokinetics, and dose-finding study of repetitive treatment with the humanized anti-interleukin 6 receptor antibody MRA in rheumatoid arthritis. Phase I/II clinical study," J Rheumatol. 30(7):1426-35 (2003).

Paino et al., "Reply to 'Response to "CD20 Positive Cells are Undetectable in the Majority of Multiple Myeloma Cell Lines and are Not Associated With a Cancer Stem Cell Phenotype,"'" Haematologica. 97(7):1110-1114 (2012) (1 page).

Pan et al. Blocking Neuropilin-1 Function Has an Additive Effect with Anti-VEGF to Inhibit Tumor Growth, Cancer Cell 11(1), Jan. 2007, pp. 53-67.

Roosnek et al., "Triggering T Cells by Otherwise Inert Hybrid Anti-CD3/Antitumor Antibodies Requires Encounter with the Specific Target Cell," J Exp Med. 170(1):297-302 (1989) (6 pages).

Schuster et al., "Immunotherapy with the trifunctional anti-CD20 x anti-CD3 antibody FBTA05 (Lymphomun) in paediatric high-risk patients with recurrent CD20-positive B cell malignancies" British Journal of Haematology, vol. 169, No. 1, 2015, pp. 90-102 (14 pages).

Seung Y. Chu et al., "Immunotherapy with long-lived anti-CD20 x anti-CD3 bispecific antibodies stimulates potent t cell-mediated killing of human b cell lines and of circulating and lymphoid b cells in monkeys: a potential therapy for b cell lymphomas and leukemias," 56th ASH Annual Meeting and Exposition, Dec. 6-9, San Francisco, CA. 124(21):3111 (2014) (1 page).

Shi et al., "Margin-Infiltrating CD20$^+$ B Cells Display an Atypical Memory Phenotype and Correlate with Favorable Prognosis in Hepatocellular Carcinoma," Clin Cancer Res. 19(21):5994-6005 (2013) (13 pages).

Somasundaram et al., "Will Engineered T Cells Expressing CD20 scFv Eradicate Melanoma?" Mol Ther. 19(4):638-40 (2011).

Spiess et al., "Alternative molecular formats and therapeutic applications for bispecific antibodies," Mol Immunol. 67:95-106, Apr. 5, 2022 (2015) (42 pages).

Stein et al., "Novel and Emerging Drugs for Acute Myeloid Leukemia," available in PMC May 22, 2014, published in final edited form as: Curr Cancer Drug Targets. 12(5):522-530 (2012) (19 pages).

Sun et al., "Anti-CD20/CD3 T cell-dependent bispecific antibody for the treatment of B cell malignancies," Sci Transl Med. 7(287):287ra70 (2015) (11 pages).

Weidle et al., "The Intriguing Options of Multispecific Antibody Formats for Treatment of Cancer," Cancer Genomics Proteomics. 10(1):1-18 (2013) (18 pages).

Wells et al., "Reaching for high-hanging fruit in drug discovery at protein-protein interfaces," Nature. 450(7172):1001-9 (2007).

Wuellner et al., "Bispecific CD3/HER2 Targeting FynomAb Induces Redirected T Cell-Mediated Cytolysis with High Potency and Enhanced Tumor Selectivity," Antibodies. 4(4):426-440 (2015) (15 pages).

Yan et al., "Succinimide Formation at Asn 55 in the Complementarity Determining Region of a Recombinant Monoclonal Antibody IgG1 Heavy Chain," J Pharm Sci. 98(10):3509-21 (2009).

Zhu et al., "Engineering high affinity humanized anti-p185HER2/anti-CD3 bispecific F(ab')2 for efficient lysis of p185HER2 overexpressing tumor cells," Int J Cancer. 62(3):319-24 (1995).

International Search Report and Written Opinion for International Patent Application No. PCT/US2023/065716, dated Jul. 27, 2023 (17 pages).

Daugherty et al., "Formulation and delivery issues for monoclonal antibody therapeutics," Adv Drug Deliv Rev. 58(5-6):686-706 (2006).

Ito et al., "Effects of subclass change on the structural stability of chimeric, humanized, and human antibodies under thermal stress," Protein Science. 22(11):1542-51 (Aug. 21, 2013).

Kang et al., "Rapid Formulation Development for Monoclonal Antibodies," BioProcess International. 14(4):40-45 (2016).

(56) References Cited

OTHER PUBLICATIONS

Wang et al., "Antibody structure, instability, and formulation," Journal of Pharmaceutical Sciences 96(1):1-26 (2007).

* cited by examiner

FIG. 1

| | | Required changes to Phase I formulation | | | Pros | | | Cons | | |
|---|---|---|---|---|---|---|---|---|---|---|
| | | Protein concentration | Surfactant concentration | Antioxidants (L-Methionine) | Flexibility of Dose | Consistency/Ease of use | Phase I data can be leveraged | Diluent needed | IV bag size CD8 isolation protocol: restrictions | DP Waste |
| Formulation Options | | | | | | | | | | |
| 1 | 1 mg/mL DP with high surfactant concentration | X | X | X | X | X | | | | |
| 2 | 1 mg/mL DP with low surfactant concentration | X | X | X | X | | | X | | |
| 3 | 60 mg/mL DP with low surfactant concentration | | | | | X | X | X | | X |
| 4 | 10 mg/mL DP with high surfactant concentration | X | X | | | | | X | X | X |
| 5 | 10 mg/mL DP with low surfactant concentration | X | X | | | X | | X | | X |
| Delivery Options | | | | | | | | | | |
| 6 | Syringe Pump with 60 mg/mL DP | | | | | X | X | X | | X |
| 7 | Remove IV bag headspace with 60 mg/mL DP | | | | | | | X | | X |
| 8 | Remove IV bag headspace with 10 mg/mL DP | X | X | | | | | | | X |

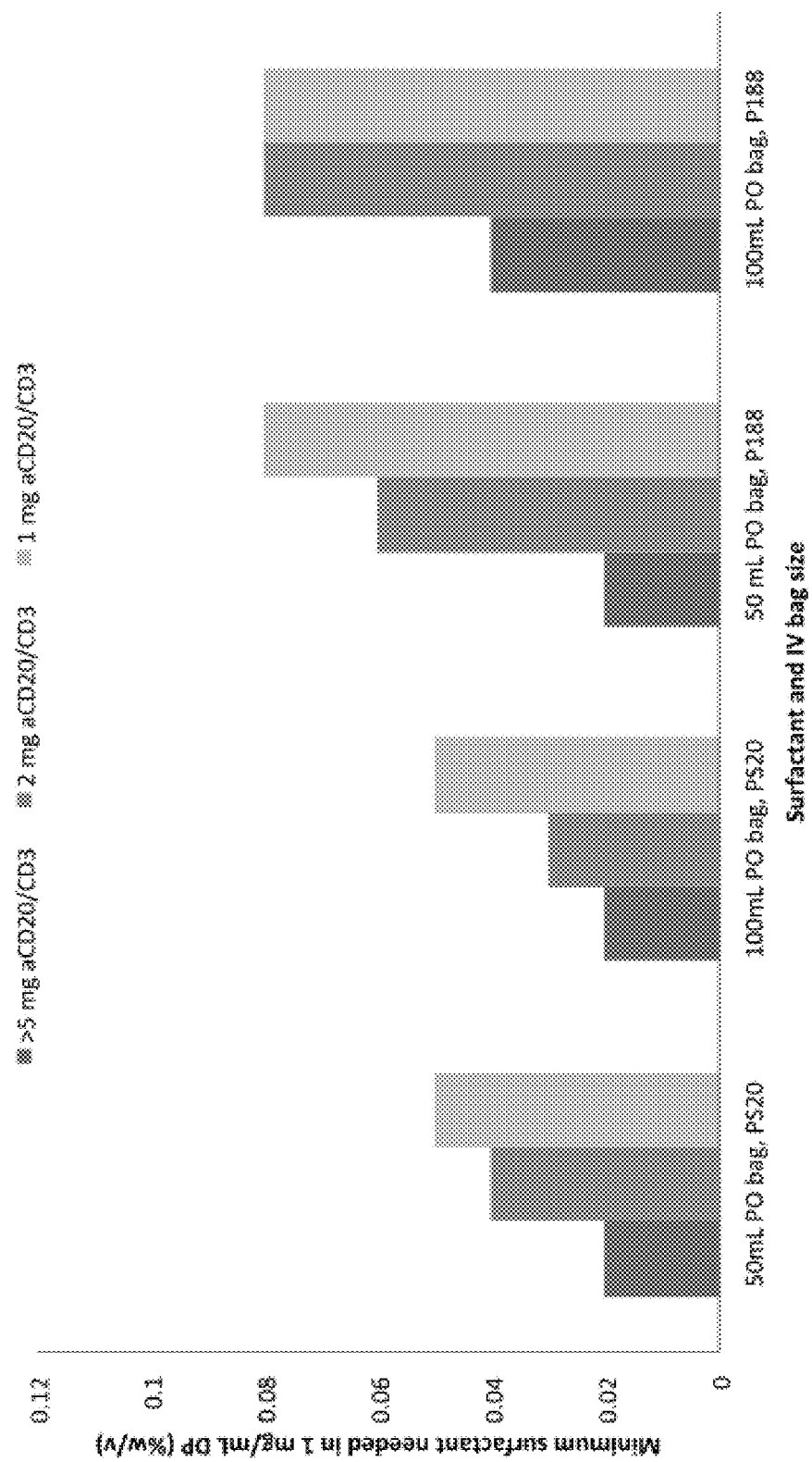

SEQUENCE LISTING

```
Sequence total quantity: 36
SEQ ID NO: 1            moltype = AA   length = 10
FEATURE                 Location/Qualifiers
source                  1..10
                        mol_type = protein
                        organism = synthetic construct
SEQUENCE: 1
GYTFTSYNMH                                                                 10

SEQ ID NO: 2            moltype = AA   length = 17
FEATURE                 Location/Qualifiers
source                  1..17
                        mol_type = protein
                        organism = synthetic construct
SEQUENCE: 2
AIYPGNGDTS YNQKFKG                                                         17

SEQ ID NO: 3            moltype = AA   length = 13
FEATURE                 Location/Qualifiers
source                  1..13
                        mol_type = protein
                        organism = synthetic construct
SEQUENCE: 3
VVYYSNSYWY FDV                                                             13
```

-continued

```
SEQ ID NO: 4           moltype = AA  length = 10
FEATURE                Location/Qualifiers
source                 1..10
                       mol_type = protein
                       organism = synthetic construct
SEQUENCE: 4
RASSSVSYMH                                                              10

SEQ ID NO: 5           moltype = AA  length = 7
FEATURE                Location/Qualifiers
source                 1..7
                       mol_type = protein
                       organism = synthetic construct
SEQUENCE: 5
APSNLAS                                                                  7

SEQ ID NO: 6           moltype = AA  length = 9
FEATURE                Location/Qualifiers
source                 1..9
                       mol_type = protein
                       organism = synthetic construct
SEQUENCE: 6
QQWSFNPPT                                                                9

SEQ ID NO: 7           moltype = AA  length = 122
FEATURE                Location/Qualifiers
source                 1..122
                       mol_type = protein
                       organism = synthetic construct
SEQUENCE: 7
EVQLVESGGG LVQPGGSLRL SCAASGYTFT SYNMHWVRQA PGKGLEWVGA IYPGNGDTSY        60
NQKFKGRFTI SVDKSKNTLY LQMNSLRAED TAVYYCARVV YYSNSYWYFD VWGQGTLVTV       120
SS                                                                     122

SEQ ID NO: 8           moltype = AA  length = 106
FEATURE                Location/Qualifiers
source                 1..106
                       mol_type = protein
                       organism = synthetic construct
SEQUENCE: 8
DIQMTQSPSS LSASVGDRVT ITCRASSSVS YMHWYQQKPG KAPKPLIYAP SNLASGVPSR        60
FSGSGSGTDF TLTISSLQPE DFATYYCQQW SFNPPTFGQG TKVEIK                      106

SEQ ID NO: 9           moltype = AA  length = 5
FEATURE                Location/Qualifiers
source                 1..5
                       mol_type = protein
                       organism = synthetic construct
SEQUENCE: 9
NYYIH                                                                    5

SEQ ID NO: 10          moltype = AA  length = 17
FEATURE                Location/Qualifiers
source                 1..17
                       mol_type = protein
                       organism = synthetic construct
SEQUENCE: 10
WIYPGDGNTK YNEKFKG                                                      17

SEQ ID NO: 11          moltype = AA  length = 10
FEATURE                Location/Qualifiers
source                 1..10
                       mol_type = protein
                       organism = synthetic construct
SEQUENCE: 11
DSYSNYYFDY                                                              10

SEQ ID NO: 12          moltype = AA  length = 17
FEATURE                Location/Qualifiers
source                 1..17
                       mol_type = protein
                       organism = synthetic construct
SEQUENCE: 12
KSSQSLLNSR TRKNYLA                                                      17

SEQ ID NO: 13          moltype = AA  length = 7
FEATURE                Location/Qualifiers
source                 1..7
                       mol_type = protein
```

```
                        organism = synthetic construct
SEQUENCE: 13
WASTRES                                                                 7

SEQ ID NO: 14           moltype = AA   length = 8
FEATURE                 Location/Qualifiers
source                  1..8
                        mol_type = protein
                        organism = synthetic construct
SEQUENCE: 14
TQSFILRT                                                                8

SEQ ID NO: 15           moltype = AA   length = 119
FEATURE                 Location/Qualifiers
source                  1..119
                        mol_type = protein
                        organism = synthetic construct
SEQUENCE: 15
EVQLVQSGAE VKKPGASVKV SCKASGYTFT NYYIHWVRQA PGQGLEWIGW IYPGDGNTKY        60
NEKFKGRATL TADTSTSTAY LELSSLRSED TAVYYCARDS YSNYYFDYWG QGTLVTVSS        119

SEQ ID NO: 16           moltype = AA   length = 112
FEATURE                 Location/Qualifiers
source                  1..112
                        mol_type = protein
                        organism = synthetic construct
SEQUENCE: 16
DIVMTQSPDS LAVSLGERAT INCKSSQSLL NSRTRKNYLA WYQQKPGQPP KLLIYWASTR        60
ESGVPDRFSG SGSGTDFTLT ISSLQAEDVA VYYCTQSFIL RTFGQGTKVE IK               112

SEQ ID NO: 17           moltype = AA   length = 25
FEATURE                 Location/Qualifiers
source                  1..25
                        mol_type = protein
                        organism = synthetic construct
SEQUENCE: 17
EVQLVESGGG LVQPGGSLRL SCAAS                                             25

SEQ ID NO: 18           moltype = AA   length = 14
FEATURE                 Location/Qualifiers
source                  1..14
                        mol_type = protein
                        organism = synthetic construct
SEQUENCE: 18
WVRQAPGKGL EWVG                                                         14

SEQ ID NO: 19           moltype = AA   length = 32
FEATURE                 Location/Qualifiers
source                  1..32
                        mol_type = protein
                        organism = synthetic construct
SEQUENCE: 19
RFTISVDKSK NTLYLQMNSL RAEDTAVYYC AR                                     32

SEQ ID NO: 20           moltype = AA   length = 11
FEATURE                 Location/Qualifiers
source                  1..11
                        mol_type = protein
                        organism = synthetic construct
SEQUENCE: 20
WGQGTLVTVS S                                                            11

SEQ ID NO: 21           moltype = AA   length = 23
FEATURE                 Location/Qualifiers
source                  1..23
                        mol_type = protein
                        organism = synthetic construct
SEQUENCE: 21
DIQMTQSPSS LSASVGDRVT ITC                                               23

SEQ ID NO: 22           moltype = AA   length = 15
FEATURE                 Location/Qualifiers
source                  1..15
                        mol_type = protein
                        organism = synthetic construct
SEQUENCE: 22
WYQQKPGKAP KPLIY                                                        15

SEQ ID NO: 23           moltype = AA   length = 32
```

```
FEATURE              Location/Qualifiers
source               1..32
                     mol_type = protein
                     organism = synthetic construct
SEQUENCE: 23
GVPSRFSGSG SGTDFTLTIS SLQPEDFATY YC                                      32

SEQ ID NO: 24        moltype = AA  length = 10
FEATURE              Location/Qualifiers
source               1..10
                     mol_type = protein
                     organism = synthetic construct
SEQUENCE: 24
FGQGTKVEIK                                                               10

SEQ ID NO: 25        moltype = AA  length = 30
FEATURE              Location/Qualifiers
source               1..30
                     mol_type = protein
                     organism = synthetic construct
SEQUENCE: 25
EVQLVQSGAE VKKPGASVKV SCKASGYTFT                                         30

SEQ ID NO: 26        moltype = AA  length = 14
FEATURE              Location/Qualifiers
source               1..14
                     mol_type = protein
                     organism = synthetic construct
SEQUENCE: 26
WVRQAPGQGL EWIG                                                          14

SEQ ID NO: 27        moltype = AA  length = 32
FEATURE              Location/Qualifiers
source               1..32
                     mol_type = protein
                     organism = synthetic construct
SEQUENCE: 27
RATLTADTST STAYLELSSL RSEDTAVYYC AR                                      32

SEQ ID NO: 28        moltype = AA  length = 11
FEATURE              Location/Qualifiers
source               1..11
                     mol_type = protein
                     organism = synthetic construct
SEQUENCE: 28
WGQGTLVTVS S                                                             11

SEQ ID NO: 29        moltype = AA  length = 23
FEATURE              Location/Qualifiers
source               1..23
                     mol_type = protein
                     organism = synthetic construct
SEQUENCE: 29
DIVMTQSPDS LAVSLGERAT INC                                                23

SEQ ID NO: 30        moltype = AA  length = 15
FEATURE              Location/Qualifiers
source               1..15
                     mol_type = protein
                     organism = synthetic construct
SEQUENCE: 30
WYQQKPGQPP KLLIY                                                         15

SEQ ID NO: 31        moltype = AA  length = 32
FEATURE              Location/Qualifiers
source               1..32
                     mol_type = protein
                     organism = synthetic construct
SEQUENCE: 31
GVPDRFSGSG SGTDFTLTIS SLQAEDVAVY YC                                      32

SEQ ID NO: 32        moltype = AA  length = 10
FEATURE              Location/Qualifiers
source               1..10
                     mol_type = protein
                     organism = synthetic construct
SEQUENCE: 32
FGQGTKVEIK                                                               10
```

```
SEQ ID NO: 33            moltype = AA  length = 452
FEATURE                  Location/Qualifiers
source                   1..452
                         mol_type = protein
                         organism = synthetic construct
SEQUENCE: 33
EVQLVESGGG LVQPGGSLRL SCAASGYTFT SYNMHWVRQA PGKGLEWVGA IYPGNGDTSY    60
NQKFKGRFTI SVDKSKNTLY LQMNSLRAED TAVYYCARVV YYSNSYWYFD VWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YGSTYRVVSV LTVLHQDWLN GKEYKCKVSN KALPAPIEKT ISKAKGQPRE PQVYTLPPSR   360
EEMTKNQVSL WCLVKGFYPS DIAVEWESNG QPENNYKTTP PVLDSDGSFF LYSKLTVDKS   420
RWQQGNVFSC SVMHEALHNH YTQKSLSLSP GK                                452

SEQ ID NO: 34            moltype = AA  length = 213
FEATURE                  Location/Qualifiers
source                   1..213
                         mol_type = protein
                         organism = synthetic construct
SEQUENCE: 34
DIQMTQSPSS LSASVGDRVT ITCRASSSVS YMHWYQQKPG KAPKPLIYAP SNLASGVPSR    60
FSGSGSGTDF TLTISSLQPE DFATYYCQQW SFNPPTFGQG TKVEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                               213

SEQ ID NO: 35            moltype = AA  length = 449
FEATURE                  Location/Qualifiers
source                   1..449
                         mol_type = protein
                         organism = synthetic construct
SEQUENCE: 35
EVQLVQSGAE VKKPGASVKV SCKASGYTFT NYYIHWVRQA PGQGLEWIGW IYPGDGNTKY    60
NEKFKGRATL TADTSTSTAY LELSSLRSED TAVYYCARDS YSNYYFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYGS   300
TYRVVSVLTV LHQDWLNGKE YKCKVSNKAL PAPIEKTISK AKGQPREPQV YTLPPSREEM   360
TKNQVSLSCA VKGFYPSDIA VEWESNGQPE NNYKTTPPVL DSDGSFFLVS KLTVDKSRWQ   420
QGNVFSCSVM HEALHNHYTQ KSLSLSPGK                                    449

SEQ ID NO: 36            moltype = AA  length = 219
FEATURE                  Location/Qualifiers
source                   1..219
                         mol_type = protein
                         organism = synthetic construct
SEQUENCE: 36
DIVMTQSPDS LAVSLGERAT INCKSSQSLL NSRTRKNYLA WYQQKPGQPP KLLIYWASTR    60
ESGVPDRFSG SGSGTDFTLT ISSLQAEDVA VYYCTQSFIL RTFGQGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                         219
```

PHARMACEUTICAL COMPOSITIONS OF MOSUNETUZUMAB AND METHODS OF USE

SEQUENCE LISTING

The instant application contains a Sequence Listing which has been submitted electronically in XML format and is hereby incorporated by reference in its entirety. Said XML copy, created on Mar. 23, 2023, is named 50474-163002_Sequence_Listing_3_23_23 and is 33,967 bytes in size.

FIELD OF THE INVENTION

The present disclosure relates to compositions (e.g., pharmaceutical compositions) comprising mosunetuzumab and methods of using the same.

BACKGROUND

Mosunetuzumab is being increasingly used as treatments for cancers, e.g., CD20-positive cell proliferative disorders (e.g., B cell proliferative disorders, e.g., non-Hodgkin's lymphomas (NHLs) (e.g., follicular lymphoma (FL), diffuse large B cell lymphoma (DLBCL), mantle cell lymphoma (MCL), etc.) or B cell chronic lymphocytic leukemia (CLL). Mosunetuzumab can be formulated in an aqueous carrier for administration to a subject, e.g., by intravenous administration.

One of the major challenges in the development of biotech therapeutics is protein stability, which has to be maintained during multiple process steps involved on their way to market. Furthermore, protein stability has to be maintained during storage as well as during administration to the patient. During storage, handling, and administration of such pharmaceutical compositions, it is necessary to mitigate loss of mosunetuzumab, which can occur through degradation and surface adsorption, such as protein adsorption to surfaces of filters, storage canisters, tubing, syringes, intravenous fluid bags, and other containers. In instances in which the pharmaceutical composition contains a relatively low concentration of mosunetuzumab, protein loss can be dramatically increased by these factors, resulting in reduced therapeutic efficacy of the pharmaceutical composition.

Thus, there is a need in the field to develop pharmaceutical formulations in which mosunetuzumab is stable and protected from loss, e.g., due to surface adsorption.

SUMMARY OF THE DISCLOSURE

The present disclosure relates to compositions (e.g., pharmaceutical compositions) comprising low concentrations of mosunetuzumab and methods of using the same. The disclosed compositions and related methods address the problem of delivering mosunetuzumab that are formulated at low concentration, ensuring that patients receive the intended dose of mosunetuzumab with little to no loss of the protein during storage and administration.

In one aspect, the disclosure provides a pharmaceutical composition that includes mosunetuzumab, a surfactant (e.g., polysorbate 20 (PS20)), methionine, a buffering agent, and a carrier, wherein the concentration of the surfactant is from 0.01% to 0.1% weight-by-volume (w/v), the concentration of methionine is from 1 mM to 50 mM, and the concentration of the buffering agent is from 5 mM to 20 mM.

In some embodiments, the concentration of the surfactant (e.g., PS20) is from 0.01% to 0.1% weight-by-volume (w/v) (e.g., from 0.01% to 0.025%, from 0.025% to 0.5%, from 0.05% to 0.075%, or from 0.075% to 0.1% (w/v), e.g., from 0.01% to 0.02%, from 0.02% to 0.03%, from 0.03% to 0.04%, from 0.04% to 0.05%, from 0.05% to 0.06%, from 0.06% to 0.07%, from 0.07% to 0.08%, from 0.08% to 0.09%, or from 0.09% to 0.1% (w/v), e.g., about 0.01%, about 0.015%, about 0.02%, about 0.025%, about 0.03%, about 0.035%, about 0.04%, about 0.045%, about 0.05%, about 0.055%, about 0.06%, about 0.065%, about 0.07%, about 0.075%, about 0.08%, about 0.085%, about 0.09%, about 0.095%, or about 0.1% (w/v)). In particular embodiments, the concentration of the surfactant (e.g., PS20) is about 0.06 (w/v) (i.e., about 0.6 mg/ml).

In some embodiments, the concentration of methionine is from 1 mM to 50 mM (e.g., from 1 mM to 10 mM, from 10 mM to 20 mM, from 20 mM to 30 mM, from 30 mM to 40 mM, or from 40 mM to 50 mM, e.g., from 5 mM to 45 mM, from 10 mM to 40 mM, from 15 mM to 35 mM, or from 20 mM to 30 mM, e.g., about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM about 40 mM, about 41 mM, about 42 mM, about 43 mM, about 44 mM, about 45 mM, about 46 mM, about 47 mM, about 48 mM, about 49 mM, or about 50 mM). In some embodiments, the concentration of methionine is from about 2.5 mM to about 20 mM. In a particular embodiment, the concentration of methionine is about 10 mM.

In some embodiments, the concentration of the buffering agent is from 5 mM to 20 mM (e.g., from 5 mM to 10 mM, from 10 mM to 15 mM, or from 15 mM to 20 mM, e.g., from 6 mM to 18 mM, from 7 mM to 16 mM, from 8 mM to 15 mM, from 9 mM to 12 mM, or from 8 mM to 12 mM, e.g., about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, or about 20 mM). In some embodiments, the concentration of the buffering agent is from about 8 mM to about 12 mM. In particular embodiments, the concentration of the buffering agent is about 10 mM.

In some embodiments, the molar ratio of the surfactant (e.g., PS20) to mosunetuzumab is 100 or less, e.g., 90 or less, 80 or less, 70 or less, 60 or less, 50 or less, 40 or less, 30 or less, 20 or less, 10 or less, 9 or less, 8 or less, 7 or less, 6 or less, 5 or less, 4 or less, 3 or less, 2 or less, or 1 or less, e.g., from from 0.5 to 100, from 0.5 to 50, from 0.5 to 10, from 0.5 to 5, from 0.5 to 1, from 1 to 5, from 2 to 4, from 5 to 100, from 10 to 70, from 10 to 50, from 10 to 30, or from 50 to 100. In certain embodiments, the molar ratio of the surfactant (e.g., PS20) to mosunetuzumab is from 1 to 100. In some embodiments, the molar ratio of the surfactant (e.g., PS20) to mosunetuzumab is from 50 to 100, from 60 to 80, or from 65 to 75, e.g., about 65, 66, 67, 68, 69, 70, 71, 72, 73, 74, or 75. In particular embodiments, the molar ratio of the surfactant to mosunetuzumab is about 71.

In some embodiments, the concentration of mosunetuzumab is between about 0.5 mg/ml to about 2 mg/ml (e.g., between about 0.5 to about 1.5 mg/ml, between about 0.7 to about 1.3 mg/ml, between about 0.8 to about 1.2 mg/ml, between about 0.9 to about 1.1 mg/ml, between about 0.5 to about 1.0 mg/ml, or between about 1 to about 1.5 mg/ml; e.g., about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml). In a particular embodiment, the concentration of mosunetuzumab is about 1 mg/ml. In some embodiments, the pharmaceutical composition is formulated as a drug product (DP).

In some embodiments, the pharmaceutical composition formulated as a DP has a mosunetuzumab concentration of about 1 mg/ml and/or a molar ratio of surfactant (e.g., PS20) to mosunetuzumab from 50 to 100, from 60 to 80, or from 65 to 75, e.g., about 65, 66, 67, 68, 69, 70, 71, 72, 73, 74, or 75. In some embodiments, the molar ratio of surfactant (e.g., PS20) to mosunetuzumab is from 65 to 75. In a particular embodiment, the molar ratio of surfactant (e.g., PS20) to mosunetuzumab in the DP is about 71.

In some embodiments, the pharmaceutical composition formulated as a DP has a mosunetuzumab concentration of about 1 mg/ml and/or a molar ratio of surfactant (e.g., P188) to mosunetuzumab from 5 to 50, from 5 to 25, from 10 to 15, or from 15 to 20, e.g., about 10, 11, 12, 13, 14, 15, 16, 17, 18, 19, or 20. In a particular embodiment, the molar ratio of surfactant (e.g., P188) to mosunetuzumab is about 14. In another particular embodiment, the molar ratio of surfactant (e.g., P188) to mosunetuzumab is about 17.

In some embodiments, the buffering agent is a histidine, a phosphate, a succinate, an acetate, or a combination thereof. For example, in particular embodiments, the buffering agent is a histidine, such as histidine acetate. The concentration of the buffering agent (e.g., histidine, e.g., histidine acetate) can be, e.g., from 8 mM to 12 mM, e.g., about 8 mM, about 9 mM, about 10 mM, about 11 mM, or about 12 mM. In a particular embodiment, the concentration of the buffering agent (e.g., histidine, e.g., histidine acetate) is about 10 mM.

In some embodiments, the pharmaceutical composition further includes a tonicity agent, such as a sugar, an amino acid, or a salt. In embodiments in which the tonicity agent is a sugar, the sugar can be, e.g., sucrose, glucose, glycerol, or trehalose. In a particular embodiment, the sugar is sucrose. In some embodiments, the concentration of the tonicity agent (e.g., sugar, e.g., sucrose) is from 100 mM to 500 mM (e.g., from 100 mM to 120 mM, from 120 mM to 140 mM, from 140 mM to 160 mM, from 160 mM to 180 mM, from 180 mM to 200 mM, from 200 mM to 220 mM, from 220 mM to 240 mM, from 240 mM to 260 mM, from 260 mM to 280 mM, from 280 mM to 300 mM, from 300 mM to 320 mM, from 320 mM to 340 mM, from 340 mM to 360 mM, from 360 mM to 380 mM, from 380 mM to 400 mM, from 400 mM to 420 mM, from 420 mM to 440 mM, from 440 mM to 460 mM, from 460 mM to 480 mM, or from 480 mM to 500 mM, e.g., from 100 mM to 400 mM, from 150 mM to 350 mM, or from 200 mM to 300 mM, e.g., about 100 mM, about 150 mM, about 200 mM, about 210 mM, about 220 mM, about 230 mM, about 240 mM, about 250 mM, about 260 mM, about 270 mM, about 280 mM, about 290 mM, about 300 mM, about 350 mM, about 400 mM, about 450 mM, or about 500 mM). In a particular embodiment, the concentration of the tonicity agent (e.g., sugar, e.g., sucrose) is about 240 mM.

In some embodiments, the pharmaceutical composition has a pH from 4.5 to 8 (e.g., from 4.5 to 5.0, from 5.0 to 5.5, from 5.5 to 6.0, from 6.0 to 6.5, from 6.5 to 7.0, from 7.0 to 7.5, or from 7.5 to 8.0, e.g., about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0). In some embodiments, the pH of the pharmaceutical composition is from 5.5 to 6.1. In a particular embodiment, the pH of the pharmaceutical composition is about 5.8.

In some embodiments, mosunetuzumab has a methionine at position 257 (i.e., Met257 or M257) of the Fc region (as in the EU index). In some embodiments, oxidation of the methionine at position 257 of the Fc region is less than 10% (e.g., less than 9%, less than 8%, less than 7%, less than 6%, less than 5%, less than 4%, less than 3%, less than 2%, or less than 1%; e.g., 0-9%, 0-8%, 0-7%, 0-6%, 0-5%, 0-4%, 0-3%, 0-2%, 0-1%, 1-5%, 1-10%, 2-9%, 3-8%, or 4-7%; e.g., about 10%, about 9%, about 8%, about 7%, about 6%, about 4%, about 4%, about 3%, about 2%, about 1%, or about 0%) over two weeks at 40° C. In some embodiments, the oxidation of the methionine at position 257 of the Fc region is no more than about 6% over two weeks at 40° C.

In another aspect, the pharmaceutical composition includes mosunetuzumab, a surfactant (e.g., PS20 or poloxamer 188 (P188)), methionine, and a carrier, wherein the pharmaceutical composition has a pH of about 5.8. In some embodiments, In some embodiments, the concentration of mosunetuzumab is between about 0.5 mg/ml to about 2 mg/ml (e.g., between about 0.5 to about 1.5 mg/ml, between about 0.7 to about 1.3 mg/ml, between about 0.8 to about 1.2 mg/ml, between about 0.9 to about 1.1 mg/ml, between about 0.5 to about 1.0 mg/ml, or between about 1 to about 1.5 mg/ml; e.g., about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml). In a particular embodiment, the concentration of mosunetuzumab is about 1 mg/ml.

In some embodiments, the concentration of the surfactant is from 0.05% to 0.1% (w/v) (e.g., from 0.05% to 0.075% or from 0.075% to 0.1% (w/v), e.g., from 0.05% to 0.06%, from 0.06% to 0.07%, from 0.07% to 0.08%, from 0.08% to 0.09%, or from 0.09% to 0.1% (w/v), e.g., about 0.05%, about 0.055%, about 0.06%, about 0.065%, about 0.07%, about 0.075%, about 0.08%, about 0.085%, about 0.09%, about 0.095%, or about 0.1% (w/v)), and the concentration of methionine is of about 10 mM.

In some embodiments, the molar ratio of the surfactant (e.g., PS20 or P188) to mosunetuzumab is 100 or less. In some embodiments, the surfactant is PS20, and the molar ratio of the surfactant (e.g., PS20) to mosunetuzumab is 100 or less, e.g., 90 or less, 80 or less, 70 or less, 60 or less, 50 or less, 40 or less, 30 or less, 20 or less, 10 or less, 9 or less, 8 or less, 7 or less, 6 or less, 5 or less, 4 or less, 3 or less, 2 or less, or 1 or less; e.g., from 0.5 to 100, from 0.5 to 50, from 0.5 to 10, from 0.5 to 5, from 0.5 to 1, from 1 to 5, from 2 to 4, from 5 to 100, from 10 to 70, from 10 to 50, from 10 to 30, from 15 to 20, from 50 to 100, from 60 to 80, or from 65 to 75. In certain embodiments, the molar ratio of PS20 to mosunetuzumab is from 50 to 100. In some embodiments, the molar ratio of PS20 to mosunetuzumab is from 50 to 100, from 60 to 80, or from 65 to 75; e.g., about 65, 66, 67, 68, 69, 70, 71, 72, 73, 74, or 75. In some embodiments, the surfactant is PS20 and the concentration of PS20 is about 0.06% (w/v). In a particular embodiment, the molar ratio of PS20 to mosunetuzumab is about 71.

In some embodiments, the concentration of mosunetuzumab is between about 0.5 mg/ml to about 2 mg/ml, e.g., about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml. In a particular embodiment, the concentration of mosunetuzumab is about 1 mg/ml. In some embodiments, the pharmaceutical composition is formulated as a DP.

In some embodiments, the molar ratio of the surfactant (e.g., P188) to mosunetuzumab is 100 or less. In some embodiments, the concentration of P188 is about 0.08% (w/v) or about 0.1% (w/v). In some embodiments, the molar ratio of P188 to mosunetuzumab is 100 or less, e.g., 90 or less, 80 or less, 70 or less, 60 or less, 50 or less, 40 or less, 30 or less, 20 or less, 10 or less, 9 or less, 8 or less, 7 or less, 6 or less, 5 or less, 4 or less, 3 or less, 2 or less, or 1 or less; e.g., from 0.5 to 100, from 0.5 to 50, from 0.5 to 10, from 0.5 to 5, from 0.5 to 1, from 1 to 5, from 2 to 4, from 1 to 20, from 1 to 30, from 1 to 15, from 10 to 20, from 5 to 100, from 10 to 70, from 5 to 50, from 10 to 50, from 10 to 30, from 15 to 20, or from 10 to 15. In some embodiments, the molar ratio of P188 to mosunetuzumab is from 5 to 50. In some embodiments, the molar ratio of P188 to mosunetuzumab is from 5 to 50, from 5 to 25, from 10 to 15, or from 15 to 20; e.g., about 10, 11, 12, 13, 14, 15, 16, 17, 18, 19, or 20. In a particular embodiment, the molar ratio of P188 to mosunetuzumab is about 14. In another particular embodiment, the molar ratio of P188 to mosunetuzumab is about 17.

In some embodiments, the pharmaceutical composition further includes histidine acetate at a concentration of about 10 mM and/or sucrose at a concentration of about 240 mM.

In another aspect, the disclosure features a pharmaceutical composition comprising mosunetuzumab, PS20, and a carrier, wherein the molar ratio of the PS20 to mosunetuzumab is 100 or less, and the concentration of PS20 is from 0.01% to 0.1% weight-by-volume (w/v).

In some embodiments, the pharmaceutical composition is in a unit dosage form (e.g., liquid formulation for infusion, liquid formulation for injection, or liquid formulation for dilution). In a particular embodiment, the pharmaceutical composition is a liquid formulation for dilution. In a particular embodiment, the liquid formulation for dilution is supplied in a container having a volume of about 50 ml (e.g., about 40 ml, about 45 ml, about 46 ml, about 47 ml, about 48 ml, about 49 ml, about 50 ml, about 51 ml, about 52 ml, about 53 ml, about 54 ml, about 55 ml, or about 60 ml). In some embodiments, the volume of the liquid formulation for dilution is between 20-40 ml (e.g., between 20-30 ml, between 30-40 ml, between 20-35 ml, between 25-40 ml, between 25-35 ml, or between 28-32 ml; e.g., about 20 ml, about 25 ml, about 26 ml, about 27 ml, about 28 ml, about 29 ml, about 30 ml, about 31 ml, about 32 ml, about 33 ml, about 34 ml, about 35 ml, or about 40 ml). In a particular embodiment, the volume of the liquid formulation for dilution is about 30 ml. In another particular embodiment, the liquid formulation for dilution is supplied in a container having a volume of about 2 ml (e.g., about 1 ml, about 1.5 ml, about 1.6 ml, about 1.7 ml, about 1.8 ml, about 1.9 ml, about 2 ml, about 2.1 ml, about 2.2 ml, about 2.3 ml, about 2.4 ml, about 2.5 ml, or about 3 ml). In some embodiments, the volume of the liquid formulation for dilution is between 0.2-2 ml (e.g., between 0.2-1.5 ml, between 0.5-2 ml, between 0.5-1 ml, or between 0.8-1.2 ml; e.g., about 0.2 ml, about 0.5 ml, about 0.6 ml, about 0.7 ml, about 0.8 ml, about 0.9 ml, about 1 ml, about 1.1 ml, about 1.2 ml, about 1.3 ml, about 1.4 ml, about 1.5 ml, or about 2 ml). In a particular embodiment, the volume of the liquid formulation for dilution is about 1 ml.

In some embodiments, the liquid formulation is for dilution with a diluent. In some embodiments, the liquid formulation is for dilution with a saline solution. In some embodiments, the liquid formulation is for dilution with a normal saline solution. In some embodiments, the normal saline solution comprises sodium chloride (NaCl). In some embodiments, the normal saline solution comprises between 0.1-1.5% (e.g., between 0.1-1.2%, between 0.3-1.5%, between 0.4-0.5%, between 0.3-1%, between 0.8-1%, between 0.85-0.95%; e.g., about 0.1%, about 0.3%, about 0.4%, about 0.45%, about 0.5%, about 0.6%, about 0.7%, about 0.8%, about 0.85%, about 0.9%, about 0.95%, about 1%, or about 1.2%) (w/v) NaCl).

In some embodiments, the pharmaceutical composition is in a container (e.g., a stainless steel container or a nickel-steel alloy container (e.g., HASTELLOY®), such as a tank (e.g., mini-tank), or can (e.g., mini-can).

In some embodiments, the pharmaceutical composition comprises no more than 1,000 particles having a diameter ≥2 µm per ml (e.g., 900 or fewer, 800 or fewer, 700 or fewer, 600 or fewer, 500 or fewer, 400 or fewer, 300 or fewer, 200 or fewer, or 100 or fewer particles having a diameter ≥2 µm per ml, e.g., from 0 to 100, from 100 to 200, from 200 to 300, from 300 to 400, from 400 to 500, from 500 to 600, from 600 to 700, from 700 to 800, from 800 to 900, or from 900 to 1,000 particles having a diameter 2 µm per ml). In some embodiments, the carrier is water.

In some embodiments, the pharmaceutical composition has a shelf-life of at least 36 months when stored at 5° C.±3° C. and protected from light (e.g., at least 38 months, at least 40 months, at least 42 months, at least 44 months, at least 46 months, at least 48 months, at least 60 months, at least 72 months, or at least 96 months). In some embodiments, the pharmaceutical composition is stable through one or more freeze-thaw cycles (e.g., two or more freeze-thaw cycles, three or more freeze-thaw cycles, four or more freeze-thaw cycles, five or more freeze-thaw cycles, six or more freeze-thaw cycles, eight or more freeze-thaw cycles, or more). In a particular embodiment, the pharmaceutical composition is stable through three or more freeze-thaw cycles. In some embodiments, the pharmaceutical composition is stable for about two weeks or longer at about 25° C. (e.g., about three weeks, about four weeks, about six weeks, about eight weeks, about 10 weeks, about 12 weeks, about 24 weeks, or longer at about 25° C.). In a particular embodiment, the pharmaceutical composition is stable for about four weeks or longer at about 25° C. In some embodiments, the pharmaceutical composition is stable for about 48 months or longer at −20° C. (e.g., about 48 months, about 60 months, about 72 months, about 84 months, about 96 months, or longer at −20° C.).

In some embodiments of any of the aspects and embodiments recited above or herein, the pharmaceutical composition has a purity of about 85% or higher, e.g., as assessed by size-exclusion high-performance liquid chromatography (SE-HPLC). In some embodiments, the purity is about 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, e.g., from 85% to 90%, from 90% to 95%, or from 95% to 100%, e.g., as assessed by SE-HPLC. In a particular embodiment, the pharmaceutical composition has a purity of about 90% or higher as assessed by SE-HPLC, or about 95% or higher as assessed by SE-HPLC. In some embodiments, the pharmaceutical composition has a purity of about 95% or higher as assessed by SE-HPLC for about 36 months or longer at about 5° C. (e.g., 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, as assessed by SE-HPLC for about 36 months or longer at about 5° C., e.g., from 85% to 90%, from 90% to 95%, or from 95% to 100%, as assessed by SE-HPLC for about 36 months or longer at about 5° C.). In a particular embodiment, the pharmaceutical composition has a purity of about 95% or higher as assessed by SE-HPLC for about 42 months or longer at about 5° C., e.g., for about 42 months, for about 60 months, for about 72 months, for about 84 months, for about 96 months, or longer, at about 5° C.

In any of the preceding aspects and embodiments, the pharmaceutical composition has a purity of about 75% or higher as assessed by non-reduced capillary electrophoresis sodium dodecyl sulfate (CE-SDS) assay (e.g., about 76% or higher, about 77% or higher, about 78% or higher, about 79% or higher, about 80% or higher, about 81% or higher, about 82% or higher, about 83% or higher, about 84% or higher, 85% or higher, about 86% or higher, about 87% or higher, about 88% or higher, about 89% or higher, about 90% or higher, about 91% or higher, about 92% or higher, about 93% or higher, about 94% or higher, about 95% or higher, about 96% or higher, about 97% or higher, about 98% or higher, about 99% or higher, as assessed by non-reduced CE-SDS assay, e.g., from 75% to 80%, from 80% to 85%, from 85% to 90%, from 90% to 95%, or from 95% to 100%, as assessed by non-reduced CE-SDS assay). In a particular embodiment, the pharmaceutical composition has a purity of about 80% or higher as assessed by non-reduced CE-SDS assay. For example, in some embodiments, the pharmaceutical composition has a purity of about 85% or higher as assessed by non-reduced CE-SDS assay. In some embodiments, the pharmaceutical composition has a purity of about 85% or higher as assessed by non-reduced CE-SDS assay for about 36 months or longer at about 5° C. (e.g., 85% or higher, about 86% or higher, about 87% or higher, about 88% or higher, about 89% or higher, about 90% or higher, about 91% or higher, about 92% or higher, about 93% or higher, about 94% or higher, about 95% or higher, about 96% or higher, about 97% or higher, about 98% or higher, about 99% or higher, as assessed by non-reduced CE-SDS assay, e.g., from 85% to 90%, from 90% to 95%, or from 95% to 100%, as assessed by non-reduced CE-SDS assay for about 36 months or longer at about 5° C.). In some embodiments, the pharmaceutical composition has a purity of about 85% or higher as assessed by non-reduced CE-SDS assay for about 42 months or longer at about 5° C. (e.g., about 85% or higher, about 86% or higher, about 87% or higher, about 88% or higher, about 89% or higher, about 90% or higher, about 91% or higher, about 92% or higher, about 93% or higher, about 94% or higher, about 95% or higher, about 96% or higher, about 97% or higher, about 98% or higher, about 99% or higher, as assessed by non-reduced CE-SDS assay, e.g., from 85% to 90%, from 90% to 95%, or from 95% to 100%, as assessed by non-reduced CE-SDS assay for about 42 months or longer at about 5° C.). In some embodiments, the non-reduced CE-SDS assay is a microchip CE-SDS (mCE-SDS) assay.

In some embodiments, the pharmaceutical composition having the any of the above shelf-life, purity, or stability properties recited above is a DS. In other embodiments, the pharmaceutical composition having the any of the shelf-life, purity, or stability properties recited above is a DP. In some embodiments, the pharmaceutical composition having the any of the shelf-life or stability properties recited above is frozen (e.g., stored at a temperature between −80° C. and 2° C. (e.g., about −40° C. or −20° C.)).

In some embodiments of any of the preceding aspects and embodiments, the pharmaceutical composition is formulated for intravenous administration. In some embodiments, the pharmaceutical composition does not contain a preservative. In some embodiments, the pharmaceutical composition is formulated for administration by infusion after dilution with saline or a diluent (e.g., a saline solution; e.g., a normal saline solution; e.g., a normal saline solution comprising 0.45% or 0.9% (w/v) NaCl). In some embodiments, the liquid formulation is for dilution with an aqueous solution. In some embodiments, the liquid formulation is for dilution with a saline solution. In some embodiments, the liquid formulation is for dilution with a normal saline solution. In some embodiments, the normal saline solution comprises sodium chloride (NaCl). In some embodiments, the normal saline solution comprises between 0.1-1.5% (e.g., between 0.1-1.2%, between 0.3-1.5%, between 0.4-0.5%, between 0.3-1%, between 0.8-1%, between 0.85-0.95%; e.g., about 0.1%, about 0.3%, about 0.4%, about 0.45%, about 0.5%, about 0.6%, about 0.7%, about 0.8%, about 0.85%, about 0.9%, about 0.95%, about 1%, or about 1.2%) (w/v) NaCl.

In another aspect, a pharmaceutical composition of any of the preceding aspects and embodiments is for use as a medicament.

In another aspect, a pharmaceutical composition of any of the preceding aspects and embodiments is for use in a treating or delaying progression of a cancer in a subject in need thereof (e.g., a human subject in need thereof).

In yet another aspect, a pharmaceutical composition of any of the preceding aspects and embodiments is for use in enhancing immune function in a subject having a cancer.

In some embodiments, the cancer is a non-Hodgkin's lymphoma (NHL). In some embodiments, the NHL is selected from the group consisting of chronic lymphoid leukemia (CLL), B cell lymphoma, splenic diffuse red pulp small B cell lymphoma, B cell lymphoma with features intermediate between diffuse large B cell lymphoma and Burkitt lymphoma, Burkitt-like lymphoma with 11q aberration, B cell lymphoma with features intermediate between diffuse large B cell lymphoma and classical Hodgkin lymphoma, diffuse large B cell lymphoma (DLBCL), germinal center B cell-like (GCB) diffuse large B cell lymphoma (DLBCL), activated B cell-like (ABC) DLBCL, primary cutaneous follicle center lymphoma, T-cell/histiocyte-rich large B cell lymphoma, primary DLBCL of the central nervous system, primary cutaneous DLBCL (leg type), Epstein-Barr virus (EBV)-positive DLBCL of the elderly, DLBCL associated with chronic inflammation, primary mediastinal (thymic) large B cell lymphoma, intravascular large B cell lymphoma, ALK-positive large B cell lymphoma, large B cell lymphoma arising in HHV8-associated multicentric Castleman disease, B cell leukemia, follicular lymphoma (FL), in situ follicular neoplasia, mantle cell lymphoma (MCL), in situ mantle cell neoplasia, acute myeloid leukemia (AML), marginal zone lymphoma (MZL), small lymphocytic leukemia (SLL), lymphoplasmacytic lymphoma (LL), Waldenstrom macroglobulinemia (WM), central nervous system lymphoma (CNSL), Burkitt's lymphoma (BL), B cell prolymphocytic leukemia, splenic marginal zone lymphoma, hairy cell leukemia, splenic lymphoma/leukemia, hairy cell leukemia variant, α heavy chain disease, γ heavy chain disease, μ heavy chain disease, plasma cell myeloma, solitary plasmacytoma of bone, extraosseous plasmacytoma, extranodal marginal zone lymphoma of mucosa-associated lymphoid tissue (MALT lymphoma), nodal marginal zone lymphoma, pediatric nodal marginal zone lymphoma, pediatric follicular lymphoma, lymphomatoid granulomatosis, plasmablastic lymphoma, and primary effusion lymphoma. In a particular embodiment, the cancer is germinal center B cell-like (GCB) DLBCL, activated B cell-like (ABC) DLBCL, follicular lymphoma (FL), mantle cell lymphoma (MCL), acute myeloid leukemia (AML), chronic lymphoid leukemia (CLL), marginal zone lymphoma (MZL), small lymphocytic leukemia (SLL), lymphoplasmacytic lymphoma (LL), Waldenstrom macroglobulinemia (WM), central nervous system lymphoma (CNSL), or Burkitt's lymphoma (BL).

In some embodiments, mosunetuzumab is formulated for administration to the subject at a dose from about 0.1 mg to about 100 mg (e.g., from 0.1 mg to 80 mg, from 0.5 to 70 mg, from 1 mg to 60 mg, from 0.1 mg to 2 mg, from 0.5 mg to 1.5 mg, from 1 mg to 5 mg, from 1.5 mg to 2.5 mg, from 1 mg to 30 mg, from 15 mg to 45 mg, from 5 mg to 10 mg, from 10 mg to 15 mg, from 20 mg to 40 mg, to 20 mg to 30 mg, from 30 mg to 40 mg, from 25 mg to 35 mg, from 50 mg to 100 mg, from 50 mg to 60 mg, from 55 mg to 65 mg, from 60 mg to 70 mg, from 70 mg to 80 mg, from 80 mg to 90 mg, or from 90 to 100 mg, e.g., about 0.5 mg, about 1 mg, about 1.5 mg, about 2 mg, about 2.5 mg, about 3 mg, about 4 mg, about 5 mg, about 6 mg, about 7 mg, about 8 mg, about 9 mg, about 10 mg, about 11 mg, about 12 mg, about 13 mg, about 13.5 mg, about 14 mg, about 15 mg, about 16 mg, about 17 mg, about 18 mg, about 19 mg, about 20 mg, about 25 mg, about 30 mg, about 40 mg, about 45 mg, about 50 mg, about 60 mg, about 70 mg, about 75 mg, about 80 mg, about 90 mg, or about 100 mg). In some embodiments, the method includes administering mosunetuzumab to the subject at a dose from about 1 mg to about 60 mg. In particular embodiments, the method includes administering mosunetuzumab to the subject at a dose of about 1 mg, about 2 mg, about 6 mg, about 9 mg, about 13.5 mg, about 20 mg, about 30 mg, or about 60 mg. In some embodiments, the method includes administering mosunetuzumab to the subject at a dose of about 1 mg, 2 mg, 30 mg, or 60 mg.

In some embodiments, the pharmaceutical composition is administered to the subject after dilution with a saline solution. In some embodiments, the saline solution is a normal saline solution. In some embodiments, the normal saline solution comprises sodium chloride (NaCl). In some embodiments, the normal saline solution comprises between 0.1-1.5% (e.g., between 0.1-1.2%, between 0.3-1.5%, between 0.4-0.5%, between 0.3-1%, between 0.8-1%, between 0.85-0.95%; e.g., about 0.1%, about 0.3%, about 0.4%, about 0.45%, about 0.5%, about 0.6%, about 0.7%, about 0.8%, about 0.85%, about 0.9%, about 0.95%, about 1%, or about 1.2%) (w/v) NaCl). In particular embodiments, the normal saline solution comprises 0.45% or 0.9% (w/v) NaCl. In some embodiments, after dilution with the normal saline solution, the concentration of mosunetuzumab is from about 0.01 mg/ml to about 0.3 mg/ml (e.g., about 0.01 mg/ml, about 0.02 mg/ml, about 0.03 mg/ml, about 0.04 mg/ml, about 0.05 mg/ml, about 0.75 mg/ml, about 0.1 mg/ml, about 0.11 mg/ml, about 0.12 mg/ml, about 0.13 mg/ml, about 0.14 mg/ml, about 0.15 mg/ml, about 0.16 mg/ml, about 0.17 mg/ml, about 0.18 mg/ml, about 0.19 mg/ml, about 0.2 mg/ml, about 0.21 mg/ml, about 0.22 mg/ml, about 0.23 mg/ml, about 0.24 mg/ml, about 0.25 mg/ml, about 0.26 mg/ml, about 0.27 mg/ml, about 0.28 mg/ml, about 0.29 mg/ml, or about 0.3 mg/ml). In particular embodiments, after dilution with the normal saline solution, the concentration of mosunetuzumab is about 0.01 mg/ml, about 0.02 mg/ml, about 0.04 mg/ml, about 0.12 mg/ml, about 0.24 mg/ml, or about 0.3 mg/ml.

In some embodiments, the subject is to be co-administered with at least one additional therapeutic agent (e.g., one, two, three, four, or more additional therapeutic agents). In some embodiments, the at least one additional therapeutic agent includes a PD-1 axis binding antagonist. In some embodiments, the PD-1 axis binding antagonist is selected from the group consisting of a PD-L1 binding antagonist, a PD-1 binding antagonist, and a PD-L2 binding antagonist. In some embodiments, the PD-1 axis binding antagonist is a PD-L1 binding antagonist (e.g., atezolizumab (MPDL3280A), MDX-1105 (BMS-936559; described in WO 2016/201425), and MED14736 (durvalumab)). In some embodiments, the PD-1 axis binding antagonist is a PD-1 binding antagonist (e.g., MDX-1106 (nivolumab), MK-3475 (lambrolizumab), AMG 404, REGN2810 (cemiplimab; LIBTAYO®), and AMP-224 (described in WO 2017/058780)). In some embodiments, the PD-1 axis binding antagonist is a PD-L2 binding antagonist (e.g., an antibody (e.g., an anti-PD-L2 antibody) or an immunoadhesin). In some embodiments, the at least one additional therapeutic agent comprises obinutuzumab, rituximab, an antibody-drug conjugate (ADC), a corticosteroid, or tocilizumab. In some embodiments, the at least one additional therapeutic agent comprises an ADC (e.g., an anti-CD79b ADC; e.g., polatuzumab vedotin). In some embodiments, the subject is a human.

In another aspect, the disclosure features a method of treating or delaying the progression of a cancer in a subject in need thereof. In some embodiments, the method includes administering to the subject an effective amount of the pharmaceutical composition of any of the preceding aspects.

In another aspect, the disclosure features a method of enhancing immune function in a subject having a cancer, e.g., by administering to the subject an effective amount of the pharmaceutical composition of any of the preceding aspects.

In some embodiments, the cancer is a non-Hodgkin's lymphoma (NHL). In some embodiments, the NHL is selected from the group consisting of chronic lymphoid leukemia (CLL), B cell lymphoma, splenic diffuse red pulp small B cell lymphoma, B cell lymphoma with features intermediate between diffuse large B cell lymphoma and Burkitt lymphoma, Burkitt-like lymphoma with 11q aberration, B cell lymphoma with features intermediate between diffuse large B cell lymphoma and classical Hodgkin lymphoma, diffuse large B cell lymphoma (DLBCL), germinal center B cell-like (GCB) diffuse large B cell lymphoma (DLBCL), activated B cell-like (ABC) DLBCL, primary cutaneous follicle center lymphoma, T-cell/histiocyte-rich large B cell lymphoma, primary DLBCL of the central nervous system, primary cutaneous DLBCL (leg type), Epstein-Barr virus (EBV)-positive DLBCL of the elderly, DLBCL associated with chronic inflammation, primary mediastinal (thymic) large B cell lymphoma, intravascular large B cell lymphoma, ALK-positive large B cell lymphoma, large B cell lymphoma arising in HHV8-associated multicentric Castleman disease, B cell leukemia, follicular lymphoma (FL), in situ follicular neoplasia, mantle cell lymphoma (MCL), in situ mantle cell neoplasia, acute myeloid leukemia (AML), marginal zone lymphoma (MZL), small lymphocytic leukemia (SLL), lymphoplasmacytic lymphoma (LL), Waldenstrom macroglobulinemia (WM), central nervous system lymphoma (CNSL), Burkitt's lymphoma (BL), B cell prolymphocytic leukemia, splenic marginal zone lymphoma, hairy cell leukemia, splenic lymphoma/leukemia, hairy cell leukemia variant, α heavy chain disease, γ heavy chain disease, μ heavy chain disease, plasma cell myeloma, solitary plasmacytoma of bone, extraosseous plasmacytoma, extranodal marginal zone lymphoma of mucosa-associated lymphoid tissue (MALT lymphoma), nodal marginal zone lymphoma, pediatric nodal marginal zone lymphoma, pediatric follicular lymphoma, lymphomatoid granulomatosis, plasmablastic lymphoma, and primary effusion lymphoma. In a particular embodiment, the cancer is germinal center B cell-like (GCB) DLBCL, activated B cell-like (ABC) DLBCL, follicular lymphoma (FL), mantle cell lymphoma (MCL), acute myeloid leukemia (AML), chronic lymphoid leukemia (CLL), marginal zone lymphoma (MZL), small lymphocytic leukemia (SLL), lymphoplasmacytic lymphoma (LL), Waldenstrom macroglobulinemia (WM), central nervous system lymphoma (CNSL), or Burkitt's lymphoma (BL).

In some embodiments, the NHL is DLBCL, GCB DLBCL, ABC DLBCL, FL, MCL, AML, CLL, MZL, SLL, LL, WM, CNSL, or BL. In some embodiments, the NHL is FL or DLBCL. In some embodiments, the NHL is relapsed and/or refractory (R/R). In some embodiments, the NHL is R/R NHL. In some embodiments, the R/R FL has relapsed after or is refractory to at least two (e.g., two, three, four, five, six, seven, eight, nine, ten, or more) prior systemic therapies. In some embodiments, the prior systemic therapy or therapies include an anti-CD20 monoclonal antibody. In some embodiments, the prior systemic therapy or therapies include an alkylating agent (e.g., bendamustine, chlorambucil, cyclophosphamide, ifosfamide, mechlorethamine, melphalan, carmustine, lomustine, streptozocin, busulfan, dacarbazine, temozolomide, altretamine, or thiotepa). In a particular embodiment, the prior systemic therapy or therapies include both an anti-CD20 monoclonal antibody and an alkylating agent.

In some embodiments, mosunetuzumab is administered to the subject at a dose from about 0.1 mg to about 100 mg (e.g., from 0.1 mg to 80 mg, from 0.5 to 70 mg, from 1 mg to 60 mg, from 0.1 mg to 2 mg, from 0.5 mg to 1.5 mg, from 1 mg to 5 mg, from 1.5 mg to 2.5 mg, from 1 mg to 30 mg, from 15 mg to 45 mg, from 5 mg to 10 mg, from 10 mg to 15 mg, from 20 mg to 40 mg, to 20 mg to 30 mg, from 30 mg to 40 mg, from 25 mg to 35 mg, from 50 mg to 100 mg, from 50 mg to 60 mg, from 55 mg to 65 mg, from 60 mg to 70 mg, from 70 mg to 80 mg, from 80 mg to 90 mg, or from 90 to 100 mg, e.g., about 0.5 mg, about 1 mg, about 1.5 mg, about 2 mg, about 2.5 mg, about 3 mg, about 4 mg, about 5 mg, about 6 mg, about 7 mg, about 8 mg, about 9 mg, about 10 mg, about 11 mg, about 12 mg, about 13 mg, about 13.5 mg, about 14 mg, about 15 mg, about 16 mg, about 17 mg, about 18 mg, about 19 mg, about 20 mg, about 25 mg, about 30 mg, about 40 mg, about 45 mg, about 50 mg, about 60 mg, about 70 mg, about 75 mg, about 80 mg, about 90 mg, or about 100 mg). In some embodiments, the method includes administering mosunetuzumab to the subject at a dose from about 1 mg to about 60 mg. In particular embodiments, the method includes administering mosunetuzumab to the subject at a dose of about 1 mg, about 2 mg, about 6 mg, about 9 mg, about 13.5 mg, about 20 mg, about 30 mg, or about 60 mg. In some embodiments, the method includes administering mosunetuzumab to the subject at a dose of about 1 mg, 2 mg, 30 mg, or 60 mg.

In some embodiments, the pharmaceutical composition is administered to the subject after dilution with a saline solution. In some embodiments, the saline solution is a normal saline solution. In some embodiments, the normal saline solution comprises sodium chloride (NaCl). In some embodiments, the normal saline solution comprises between 0.1-1.5% (e.g., between 0.1-1.2%, between 0.3-1.5%, between 0.4-0.5%, between 0.3-1%, between 0.8-1%, between 0.85-0.95%; e.g., about 0.1%, about 0.3%, about 0.4%, about 0.45%, about 0.5%, about 0.6%, about 0.7%, about 0.8%, about 0.85%, about 0.9%, about 0.95%, about 1%, or about 1.2%) (w/v) NaCl). In particular embodiments, the normal saline solution comprises 0.45% or 0.9% (w/v) NaCl. In some embodiments, after dilution with the normal saline solution, the concentration of mosunetuzumab is from about 0.01 mg/ml to about 0.3 mg/ml (e.g., about 0.01 mg/ml, about 0.02 mg/ml, about 0.03 mg/ml, about 0.04 mg/ml, about 0.05 mg/ml, about 0.75 mg/ml, about 0.1 mg/ml, about 0.11 mg/ml, about 0.12 mg/ml, about 0.13 mg/ml, about 0.14 mg/ml, about 0.15 mg/ml, about 0.16 mg/ml, about 0.17 mg/ml, about 0.18 mg/ml, about 0.19 mg/ml, about 0.2 mg/ml, about 0.21 mg/ml, about 0.22 mg/ml, about 0.23 mg/ml, about 0.24 mg/ml, about 0.25 mg/ml, about 0.26 mg/ml, about 0.27 mg/ml, about 0.28 mg/ml, about 0.29 mg/ml, or about 0.3 mg/ml). In particular embodiments, after dilution with the normal saline solution, the concentration of mosunetuzumab is about 0.01 mg/ml, about 0.02 mg/ml, about 0.04 mg/ml, about 0.12 mg/ml, about 0.24 mg/ml, or about 0.3 mg/ml.

In one aspect, the pharmaceutical compositions (e.g., comprising mosunetuzumab) disclosed herein is administered to a subject in a dosing regimen comprising at least three 21-day (±3 days) dosing cycles, wherein (a) the first 21-day dosing cycle comprises a first dose (C1D1), a second dose (C1D2), and a third dose (C1D3) of mosunetuzumab administered to the subject on or about days 1, 8 (±1 day), and 15 (±1 day), respectively, of the first dosing cycle, wherein the C1D1 is about 1 mg (±0.5), the C1D2 is about 2 (±0.5) mg, and the C1D3 is about 60 (±5) mg; (b) the second dosing cycle comprises a single dose (C2D1) of mosunetuzumab administered to the subject on or about day 1 of the second dosing cycle, wherein the C2D1 is about 60 (±5) mg; and (c) the third dosing cycle comprises a single dose (C3D1) of mosunetuzumab administered to the subject on or about day 1 of the third dosing cycle, wherein the C3D1 is about 30 (±3) mg. In some embodiments, the dosing regimen comprises one to fourteen additional dosing cycles each comprising an additional single dose of about 30 (±0.5) mg of mosunetuzumab. In some embodiments, the dosing regimen comprises one to five (e.g., one, two, three, four, or five) additional dosing cycles. In a particular embodiment, the dosing regimen comprises five additional dosing cycles. In some embodiments, each additional single dose of mosunetuzumab is administered to the subject on or about day 1 of each respective additional dosing cycle.

In some embodiments, the subject is co-administered with at least one additional therapeutic agent (e.g., one, two, three, four, or more additional therapeutic agents). In some embodiments, the at least one additional therapeutic agent includes a PD-1 axis binding antagonist. In some embodiments, the PD-1 axis binding antagonist is selected from the group consisting of a PD-L1 binding antagonist, a PD-1 binding antagonist, and a PD-L2 binding antagonist. In some embodiments, the PD-1 axis binding antagonist is a PD-L1 binding antagonist (e.g., atezolizumab (MPDL3280A), MDX-1105 (BMS-936559), and MED14736 (durvalumab)). In some embodiments, the PD-1 axis binding antagonist is a PD-1 binding antagonist (e.g., MDX-1106 (nivolumab), MK-3475 (lambrolizumab), AMG 404, REGN2810 (cemiplimab; LIBTAYO®), and AMP-224 (described in WO 2017/058780). In some embodiments, the PD-1 axis binding antagonist is a PD-L2 binding antagonist (e.g., an antibody (e.g., an anti-PD-L2 antibody) or an immunoadhesin). In some embodiments, the at least one additional therapeutic agent comprises obinutuzumab, rituximab, an antibody-drug conjugate (ADC), a corticosteroid, or tocilizumab. In some embodiments, the at least one additional therapeutic agent comprises an ADC (e.g., an anti-CD79b ADC, e.g., polatuzumab vedotin).

In some embodiments, the pharmaceutical composition is administered intravenously. In some embodiments, the subject is a human.

Each and every embodiment can be combined unless the context clearly suggests otherwise. Each and every embodiment can be applied to each and every aspect of the disclosure unless the context clearly suggests otherwise.

Specific embodiments of the present disclosure will become evident from the following more detailed description of certain preferred embodiments and the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a table summarizing delivery and in-use considerations for various phase III drug product (DP) formulations.

FIG. 3 is a graph showing the effect of various IV bag sizes and mosunetuzumab quantities on minimum surfactant (PS20 or P188) concentrations required for prevention of aggregation and particle formation in 1 mg/ml DP. The first bar for each set of conditions on the x-axis (left to right) represents >5 mg of mosunetuzumab, the second bar represents 2 mg of mosunetuzumab, and the third bar represents 1 mg of mosunetuzumab.

DETAILED DESCRIPTION OF EMBODIMENTS OF THE DISCLOSURE

I. Definitions

Figure 2:
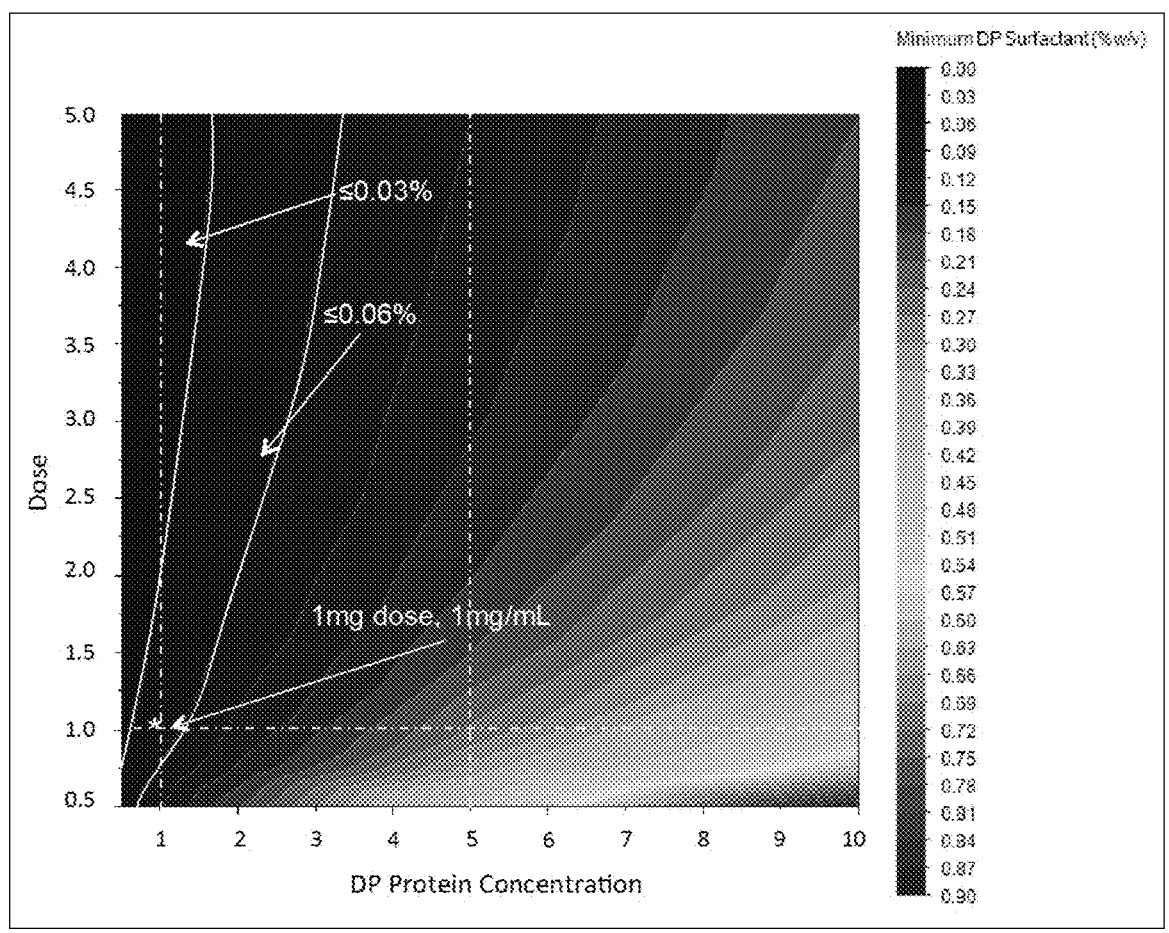
FIG. 2 is a graph showing minimum PS20 concentration (% w/v) as a function of dose and DP protein concentration, determined by IV bag shaking study in 100 ml PO bags. The x-axis shows DP protein concentration in mg/ml, while the y-axis shows dose in mg.

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art.

The term "about" as used herein refers to the usual error range for the respective value readily known to the skilled person in this technical field. Reference to "about" a value or parameter herein includes (and describes) embodiments that are directed to that value or parameter per se.

As used herein, the singular forms "a," "an," and "the" include plural referents unless the context clearly dictates otherwise. For example, reference to "an isolated peptide" means one or more isolated peptides.

Throughout this specification and claims, the word "comprise," or variations such as "comprises" or "comprising" will be understood to imply the inclusion of a stated integer or group of integers but not the exclusion of any other integer or group of integers.

The terms "pharmaceutical composition" and "pharmaceutical formulation" are used interchangeably herein and refer to a preparation which is in such form as to permit the biological activity of an active ingredient contained therein to be effective, and which contains no additional components which are unacceptably toxic to a subject to which the formulation would be administered.

A "pharmaceutically acceptable carrier" or "carrier" refers to an ingredient in a pharmaceutical formulation, other than an active ingredient, which is nontoxic to a subject. A pharmaceutically acceptable carrier or carrier includes, but is not limited to, a buffer, excipient, stabilizer, or preservative.

The term "shelf-life" refers to the length of time that a product (e.g., mosunetuzumab) may be stored without becoming unfit for use (e.g., by administration to a subject) or sale. In some embodiments, the shelf-life is the length of time in which a composition (e.g., a pharmaceutical composition) is stable. For example, in some embodiments, a composition herein has a shelf-life of at least 36 months when stored at 5° C.±3° C. and protected from light.

A "stable" pharmaceutical formulation is one in which the protein (e.g., mosunetuzumab) therein essentially retains its physical stability and/or chemical stability and/or biological activity upon storage. Preferably, the formulation essentially retains its physical and chemical stability, as well as its biological activity upon storage (e.g., frozen storage). The storage period is generally selected based on the intended shelf-life of the formulation. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected amount of light exposure and/or temperature for a selected time period. Stability can be evaluated qualitatively and/or quantitatively in a variety of different ways, including evaluation of aggregate formation (for example, using size exclusion chromatography, by measuring turbidity, and/or by visual inspection); evaluation of ROS formation (for example, by using a light stress assay or an 2,2'-azobis(2-amidinopropane) dihydrochloride (AAPH) stress assay); oxidation of specific amino acid residues of the protein (for example, a Met residue of an antibody (e.g., mosunetuzumab)); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact polypeptides; peptide map (for example, tryptic or LYS-C) analysis; evaluating biological activity or target binding function of the protein (e.g., binding of an antibody to its antigen, e.g., binding of mosunetuzumab to a T cell and/or a target cell); and the like. Instability may involve any one or more of: aggregation, deamidation (e.g., Asn deamidation), oxidation (e.g., Met oxidation and/or Trp oxidation), isomerization (e.g., Asp isomerization), clipping/hydrolysis/fragmentation (e.g., hinge region fragmentation), succinimide formation, unpaired cysteine(s), N-terminal extension, C-terminal processing, glycosylation differences, and the like.

A protein (e.g., mosunetuzumab) "retains its physical stability" in a pharmaceutical formulation if it shows no signs or very little of aggregation, precipitation, fragmentation, and/or denaturation upon visual examination of color and/or clarity, or as measured by UV light scattering or by size exclusion chromatography.

A protein (e.g., mosunetuzumab) "retains its chemical stability" in a pharmaceutical formulation, if the chemical stability at a given time is such that the protein (e.g., mosunetuzumab) is considered to still retain its biological activity as defined below. Chemical stability can be assessed by detecting and quantifying chemically altered forms of the protein (e.g., mosunetuzumab). Chemical alteration may involve protein oxidation, which can be evaluated using tryptic peptide mapping, reverse-phase high-performance liquid chromatography (HPLC) and liquid chromatography-mass spectrometry (LC/MS), for example. Other types of chemical alteration include charge alteration of the protein (e.g., mosunetuzumab), which can be evaluated by ion-exchange chromatography or icIEF, for example.

A protein (e.g., mosunetuzumab) "retains its biological activity" in a pharmaceutical formulation, if the biological activity of the protein (e.g., mosunetuzumab) at a given time is within about 20% (such as within about 10%) of the biological activity exhibited at the time the pharmaceutical formulation was prepared (within the errors of the assay), as determined, for example, in a receptor binding assay.

As used herein, "biological activity" of a protein (e.g., mosunetuzumab) refers to the ability of the protein to bind its target, for example, the ability of an antibody to bind its antigen (e.g., the ability of a mosunetuzumab to bind a T cell and/or a target cell). It can further include a biological response, which can be measured in vitro or in vivo. Such activity may be antagonistic or agonistic.

A protein (e.g., mosunetuzumab) which is "susceptible to oxidation" is one comprising one or more residue(s) that has been found to be prone to oxidation such as, but not limited to, methionine (Met), cysteine (Cys), histidine (His), tryptophan (Trp), and tyrosine (Tyr). For example, one or more methionine residues (e.g., Methionine 257, Met247, or M257) in mosunetuzumab, may be susceptible to oxidation.

The term "percent oxidation" refers to the percentage of proteins (e.g., mosunetuzumab) in a formulation (e.g., a pharmaceutical composition) that are oxidized at a particular amino acid residue, for example, a Met residue. Percent oxidation can be determined by, e.g., mass spectrometry (MS) analysis of one or more tryptic peptides, in which one or more particular oxidation-prone amino acid residues reside. Percent oxidation may be determined, for example, following an AAPH stress test, within 9 months, 12 months, 18 months, or two years from the initial production of the protein (e.g., mosunetuzumab) or pharmaceutical composition thereof.

The term "as assessed by an AAPH stress test," as used herein, means that the percent oxidation at a particular amino acid residue (for example, a Met residue, e.g., at Met257) is determined by mass spectrometry analysis of tryptic peptides following formulating the protein (e.g., mosunetuzumab) with AAPH (e.g., about 0 mM AAPH, about 1 mM AAPH, about 3 mM AAPH, about 3.5 mM AAPH, or about 5 mM AAPH), for example, in a formulation of about 10 mg/ml mosunetuzumab, about 10 mM histidine acetate, about 240 mM sucrose, about 0.06 (w/v) polysorbate 20, pH about 5.8 for about 24 hours at about 40° C. The stressed protein (e.g., mosunetuzumab) is digested with trypsin and the digested peptides are subjected to LC-MS-MS to determine the percentage of oxidation.

As used herein, "buffer" refers to a buffered solution that resists changes in pH by the action of its acid-base conjugate components (also referred to herein as "buffering agents"). In some embodiments, the buffer of this disclosure has a pH in the range of from about 4.5 to about 8. In some embodiments, the buffer has a pH in the range from about 5.5 to 6.1 (e.g., about 5.5, about 5.6, about 5.7, about 5.8, about 5.9, about 6.0, or about 6.1), e.g., about pH 5.8. Exemplary buffering agents for use in the disclosure include, but are not limited to, histidine (e.g., histidine acetate), an acetate, a phosphate, a succinate, a borate, a citrate, a tartrate, a lactate, or a combination thereof. In some embodiments, the histidine is histidine acetate. In some embodiments, the phosphate is sodium phosphate monobasic, sodium phosphate dibasic, sodium phosphate tribasic, potassium phosphate monobasic, potassium phosphate dibasic, potassium phosphate tribasic, or a mixture thereof.

As used herein, a "tonicity agent" refers to an agent that can be added to a liquid (e.g., an aqueous solution) to adjust the tonicity of said liquid. Tonicity refers to a measure of an osmotic pressure gradient between two solutions. In some embodiments, tonicity agents cannot cross a semipermeable membrane (e.g., a semi-permeable cell membrane) that otherwise permits the liquid (e.g., an aqueous solution) or other components of the liquid (e.g., other solutes) to cross. In some embodiments, tonicity agents are used to reduce local irritation by preventing osmotic shock at the site of application. Exemplary tonicity agents include carbohydrates (e.g., sucrose, glucose, dextrose, glycerol, glycerin, mannitol, and trehalose), amino acids, and salts (e.g., sodium chloride and potassium chloride).

As used herein, a "surfactant" refers to a surface-active agent, preferably a nonionic surfactant. Examples of surfactants herein include polysorbate (for example, polysorbate 20, polysorbate 40, polysorbate 60, polysorbate 65, polysorbate 80, polysorbate 85); poloxamer (e.g., poloxamer 188); TRITON®; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.); polyethyl glycol, polypropyl glycol, and copolymers of ethylene and propylene glycol (e.g., PLURONIC® type block copolymers, e.g., PLURONIC® F-68); and the like. In one embodiment, the surfactant herein is polysorbate 20 (PS20). In yet another embodiment, the surfactant herein is poloxamer 188 (P188).

A "preservative" is a compound which can be optionally included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl, and benzyl alcohol; alkyl parabens such as methyl or propyl paraben; catechol; resorcinol; cyclohexanol; 3-pentanol, and m-cresol. In one embodiment, the preservative herein is benzyl alcohol. In some embodiments, the formulation does not include a preservative.

The "molar ratio of the surfactant to mosunetuzumab" (surfactant:antibody) is the ratio of surfactant to mosunetuzumab, where each component is expressed in molarity (also referred to as molar concentration). Equation (1) depicts this ratio:

$$\text{Molar ratio (surfactant: mosunetuzumab)} = \frac{\text{Surfactant } M}{\text{Mosunetuzumab } M} \quad (1)$$

As used herein, a "drug substance" or "DS" refers to a pharmaceutical composition formulated for storage prior to administration to a subject, e.g., frozen storage. A DS may have a concentration of mosunetuzumab that is greater than the concentration of mosunetuzumab to be administered to the subject. Accordingly, in some instances, the DS is diluted prior to administration to the subject.

As used herein, a "drug product" or "DP" refers to a pharmaceutical composition in its final configuration such that it is ready to be administered to a subject (e.g., in final vial configuration). The concentration of mosunetuzumab in a DP may be the concentration at which it is to be administered to the subject. Alternatively, if the DP is to be administered with a diluent (e.g., a saline solution; e.g., a normal saline solution; e.g., a normal saline solution comprising 0.45% or 0.9% (w/v) NaCl), or if it is intended to be administered in combination with other therapeutic reagents, the DP may be at a higher concentration than the concentration at which it is to be administered to the subject.

As used herein, a "saline" solution refers to an aqueous solution comprising a salt (e.g., an ionic salt, e.g., sodium chloride (NaCl)). In some embodiments, a saline solution comprises a normal saline solution. In some embodiments, a normal saline solution comprises 0.45% or 0.9% NaCl. In some embodiments, a normal saline solution is used to dilute a liquid formulation prior to intravenous administration.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *PCR Protocols: A Guide to Methods and Applications* (Innis, et al. 1990. Academic Press, San Diego, CA), and Harlow and Lane (1988) *Antibodies: A Laboratory Manual* ch. 14 (Cold Spring Harbor Laboratory, Cold Spring Harbor, NY).

As appropriate, procedures involving the use of commercially available kits and reagents are generally carried out in accordance with manufacturer defined protocols and/or parameters unless otherwise noted. Before the present methods and uses therefore are described, it is to be understood that this disclosure is not limited to the particular methodology, protocols, cell lines, animal species or genera, constructs, and reagents described as such can, of course, vary. It is also to be understood that the terminology used herein is for the purpose of describing particular embodiments only, and is not intended to limit the scope of the present disclosure which will be limited only by the appended claims.

The term "antibody" herein is used in the broadest sense and encompasses various antibody structures, including but not limited to monoclonal antibodies, polyclonal antibodies, multispecific antibodies (e.g., mosunetuzumab), and antibody fragments, so long as they exhibit the desired antigen-binding activity (e.g., an antigen-binding fragment of an antibody).

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

By "binding domain" is meant a part of a compound or a molecule that specifically binds to a target epitope, antigen, ligand, or receptor. Binding domains can be part of a molecule such as an antibody (e.g., a monoclonal, polyclonal, recombinant, humanized, or chimeric antibody), an antibody fragment, or a portion thereof (e.g., a Fab fragment, Fab'$_2$, scFv antibody, SMIP, domain antibody, diabody, minibody, scFv-Fc, affibody, nanobody, or a VH and/or VL domain of an antibody), receptor, ligand, aptamer, or other molecule having an identified binding partner.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., supra);

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al. *Kuby Immunology*, 6th ed., W.H. Freeman and Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., supra.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

"Percent (%) amino acid sequence identity" or "percent (%) sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN® (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX® operating system, including digital UNIX® V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "chimeric" antibody refers to an antibody in which a portion of the heavy and/or light chain is derived from a particular source or species, while the remainder of the heavy and/or light chain is derived from a different source or species.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., supra. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The terms "full-length antibody," "intact antibody," and "whole antibody" are used herein interchangeably to refer to an antibody having a structure substantially similar to a native antibody structure or having heavy chains that contain an Fc region as defined herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227:381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized XENOMOUSE™ (see, e.g., U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B cell hybridoma technology.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical composition.

"Native antibodies" refer to naturally occurring immunoglobulin molecules with varying structures. For example, native IgG antibodies are heterotetrameric glycoproteins of about 146,000 Daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

As used herein, the term "half antibody" refers to one immunoglobulin heavy chain associated with one immunoglobulin light chain.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "cluster of differentiation 3" or "CD3," as used herein, refers to any native CD3 from any vertebrate source, including mammals such as primates (e.g., humans and cynomolgus monkeys (cyno)) and rodents (e.g., mice and rats), unless otherwise indicated, including, for example, CD3ε, CD3γ, CD3α, and CD3β chains. The term encompasses "full-length," unprocessed CD3 (e.g., unprocessed or unmodified CD3ε or CD3γ), as well as any form of CD3 that results from processing in the cell. The term also encompasses naturally occurring variants of CD3, including, for example, splice variants or allelic variants. CD3 includes, for example, human CD3ε protein (NCBI RefSeq No. NP_000724), which is 207 amino acids in length, human CD3γ protein (NCBI RefSeq No. NP_000064), which is 182 amino acids in length, cyno CD3ε protein (NCBI RefSeq No. NP_001270544.1), which is 198 amino acids in length, and cyno CD3γ protein (NCBI RefSeq No. NP_001270839.1), which is 181 amino acids in length.

The term "cluster of differentiation 20" or "CD20," as used herein, refers to any native CD20 from any vertebrate source, including mammals such as primates (e.g., humans) and rodents (e.g., mice and rats), unless otherwise indicated. The term encompasses "full-length," unprocessed CD20, as well as any form of CD20 that results from processing in the cell. The term also encompasses naturally occurring variants of CD20, including, for example, splice variants or allelic variants. CD20 includes, for example, human CD20 protein (see, e.g., NCBI RefSeq Nos. NP_068769.2 and NP_690605.1), which is 297 amino acids in length and may be generated, for example, from variant mRNA transcripts that lack a portion of the 5' UTR (see, e.g., NCBI RefSeq No. NM_021950.3) or longer variant mRNA transcripts (see, e.g., NCBI RefSeq No. NM_152866.2).

The terms "anti-CD20/anti-CD3 antibody," "anti-CD20/anti-CD3 bispecific antibody," "anti-CD20/anti-CD3 TDB," or variants thereof, refer to a multispecific antibody (e.g., a bispecific antibody) that is capable of binding to CD20 and CD3 with sufficient affinity such that the antibody is useful as a diagnostic and/or therapeutic agent in targeting CD20 and/or CD3. In one embodiment, the extent of binding of an anti-CD20/anti-CD3 antibody to an unrelated, non-CD3 protein and/or non-CD20 protein is less than about 10% of the binding of the antibody to CD3 and/or CD20 as measured, e.g., by a radioimmunoassay (RIA). In certain embodiments, the anti-CD20/anti-CD3 bispecific antibody binds to CD20 and CD3 with a dissociation constant ($K_D$) of ≤1 μM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). In some embodiments, the anti-CD20/anti-CD3 antibody is mosunetuzumab. Mosunetuzumab (also known as BTCT4465A or RG7828) is defined by International Nonproprietary Names for Pharmaceutical Substances (INN) List 117 (WHO Drug Information, Vol. 31, No. 2, 2017, p. 304-305). In some instances, mosunetuzumab is an anti-CD20/anti-CD3 bispecific antibody (anti-CD20/anti-CD3 T-cell dependent bispecific antibody) described in PCT Pat. Pub. No. WO 2015/095392, which is incorporated herein by reference in its entirety.

A "subject" or an "individual" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the subject or individual is a human.

As used herein, "administering" is meant a method of giving a dosage of mosunetuzumab or a composition (e.g., a pharmaceutical composition, e.g., a pharmaceutical composition including mosunetuzumab to a subject. The pharmaceutical compositions utilized in the methods described herein can be administered, for example, intravenously, intradermally, intramuscularly, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions. The method of administration can vary depending on various factors (e.g., the pharmaceutical composition being administered and the severity of the condition, disease, or disorder (e.g., cancer) being treated).

As used herein, a "week" is 7 days±2 days.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, pharmaceutical compositions of the disclosure are used to delay development of a disease or to slow the progression of a disease.

As used herein, "enhancing immune function" in a subject means to induce, cause, stimulate, sustain, or amplify the innate or adaptive immune response. In some embodiments, enhancing immune function includes enhancing T-cell function. In some embodiments, the level of enhancement is as least 50%, alternatively 60%, 70%, 80%, 90%, 100%, 120%, 150%, 200%. The manner of measuring this enhancement is known to one of ordinary skill in the art.

As used herein, "enhancing T-cell function" means to induce, cause, or stimulate a T-cell to have a sustained or amplified biological function, or renew or reactivate exhausted or inactive T-cells. Examples of enhancing T-cell function include: increased secretion of γ-interferon from CD8+ T-cells, increased proliferation, increased antigen responsiveness (e.g., viral, pathogen, or tumor clearance) relative to such levels before the intervention. In some embodiment, the level of enhancements is as least 50%, alternatively 60%, 70%, 80%, 90%, 100%, 120%, 150%, 200%, 300%, 400%, 500%. The manner of measuring this enhancement is known to one of ordinary skill in the art.

As used herein, "delaying progression" of a cancer means to defer, hinder, slow, retard, stabilize, and/or postpone development of the cancer. This delay can be of varying lengths of time, depending on the history of the cancer and/or individual being treated. As is evident to one skilled in the art, a sufficient or significant delay can, in effect, encompass prevention, in that the individual does not develop the cancer. For example, a late stage cancer, such as development of metastasis, may be delayed.

By "reduce" or "inhibit" is meant the ability to cause an overall decrease, for example, of 20% or greater, of 50% or greater, or of 75%, 85%, 90%, 95%, or greater. In certain embodiments, reduce or inhibit can refer to the effector function of an antibody that is mediated by the antibody Fc region, such effector functions specifically including complement-dependent cytotoxicity (CDC), antibody-dependent cellular cytotoxicity (ADCC), and antibody-dependent cellular phagocytosis (ADCP).

A "disorder" is any condition that would benefit from treatment including, but not limited to, chronic and acute disorders or diseases including those pathological conditions which predispose the mammal to the disorder in question.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include, but not limited to, B cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In other embodiments, the cancer is selected from a class of mature B cell cancers excluding Hodgkin's Lymphoma but including diffuse large B cell lymphoma (DLBCL), germinal-center B cell-like (GCB) DLBCL, activated B cell-like (ABC) DLBCL, follicular lymphoma (FL), mantle cell lymphoma (MCL), acute myeloid leukemia (AML), chronic lymphoid leukemia (CLL), marginal zone lymphoma (MZL), small lymphocytic leukemia (SLL), lymphoplasmacytic lymphoma (LL), Waldenstrom macroglobulinemia (WM), central nervous system lymphoma (CNSL), Burkitt's lymphoma (BL), B cell prolymphocytic leukemia, Splenic marginal zone lymphoma, Hairy cell leukemia, Splenic lymphoma/leukemia, unclassifiable, Splenic diffuse red pulp small B cell lymphoma, Hairy cell leukemia variant, Heavy chain diseases, a Heavy chain disease, γ Heavy chain disease, μ Heavy chain disease, Plasma cell myeloma, Solitary plasmacytoma of bone, Extraosseous plasmacytoma, Extranodal marginal zone lymphoma of mucosa-associated lymphoid tissue (MALT lymphoma), Nodal marginal zone lymphoma, Pediatric nodal marginal zone lymphoma, Pediatric follicular lymphoma, Primary cutaneous follicle center lymphoma, T-cell/histiocyte rich large B cell lymphoma, Primary DLBCL of the CNS, Primary cutaneous DLBCL, leg type, EBV-positive DLBCL of the elderly, DLBCL associated with chronic inflammation, Lymphomatoid granulomatosis, Primary mediastinal (thymic) large B cell lymphoma, Intravascular large B cell lymphoma, ALK-positive large B cell lymphoma, Plasmablastic lymphoma, Large B cell lymphoma arising in HHV8-associated multicentric Castleman disease, Primary effusion lymphoma: B cell lymphoma, unclassifiable, with features intermediate between diffuse large B cell lymphoma and Burkitt lymphoma, and B cell lymphoma, unclassifiable, with features intermediate between diffuse large B cell lymphoma and classical Hodgkin lymphoma.

"Tumor," as used herein, refers to all neoplastic cell growth and proliferation, whether malignant or benign, and all pre-cancerous and cancerous cells and tissues. The terms "cancer", "cancerous", "cell proliferative disorder", "proliferative disorder", and "tumor" are not mutually exclusive as referred to herein.

The term "tumor antigen," as used herein, may be understood as those antigens that are presented on tumor cells. These antigens can be presented on the cell surface with an extracellular part, which is often combined with a transmembrane and cytoplasmic part of the molecule. These antigens can sometimes be presented only by tumor cells and never by the normal ones. Tumor antigens can be exclusively expressed on tumor cells or might represent a tumor specific mutation compared to normal cells. In this case, they are called tumor-specific antigens. More common are tumor antigens that are presented by tumor coils and normal cells, and they are called tumor-associated antigens. These tumor-associated antigens can be overexpressed compared to normal cells or are accessible, for antibody binding in tumor cells due to the less compact structure of the tumor tissue, compared to normal tissue.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

An "effective amount" of a pharmaceutical composition, for example, a pharmaceutical composition including mosunetuzumab is at least the minimum amount required to achieve the desired therapeutic or prophylactic result, such as a measurable improvement of a cancer. An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this disclosure, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

The term "package insert" is used to refer to instructions customarily included in commercial packages of therapeutic products, that contain information about the indications, usage, dosage, administration, combination therapy, contraindications and/or warnings concerning the use of such therapeutic products.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 (nivolumab) described herein. In another specific aspect, a PD-1 binding antagonist is MK-3475 (lambrolizumab) described herein. In another specific aspect, a PD-1 binding antagonist is AMG 404 described herein. In another specific aspect, a PD-1 binding antagonist is REGN2810 (cemiplimab; LIBTAYO®) described herein. In another specific aspect, a PD-1 binding antagonist is AMP-224 described herein and in PCT Pub. No. WO 2017/058780.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is atezolizumab (MPDL3280A) described herein. In still another specific aspect, an anti-PD-L1 antibody is MDX-1105 (BMS-936559) described herein and in PCT Pub. No. WO 2016/201425. In still another specific aspect, an anti-PD-L1 antibody is MED14736 (durvalumab) described herein.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

II. Pharmaceutical Compositions

This disclosure provides pharmaceutical compositions that include mosunetuzumab, and uses thereof, for example, for treatment of cancers (e.g., hematological cancers). Pharmaceutical compositions of the disclosure can be formulated to support relatively low concentrations of mosunetuzumab.

In one aspect, the disclosure provides a pharmaceutical composition that includes mosunetuzumab, a surfactant (e.g., polysorbate 20 (PS20)), methionine, a buffering agent, and a carrier. In the pharmaceutical composition, the concentration of PS20 is from 0.01% to 0.1% weight-by-volume (w/v), the concentration of methionine is from 1 mM to 50 mM, and the concentration of the buffering agent is from 5 mM to 20 mM.

The pharmaceutical compositions may have a concentration of mosunetuzumab is between about 0.5 mg/ml to about 2 mg/ml, e.g., about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml. In a particular embodiment, the concentration of mosunetuzumab is about 1 mg/ml.

In some instances, the molar ratio of the surfactant (e.g., PS20) to mosunetuzumab is 100 or less, 90 or less, 80 or less, 70 or less, 60 or less, 50 or less, 40 or less, 30 or less, 20 or less, 10 or less, 9 or less, 8 or less, 7 or less, 6 or less, 5 or less, 4 or less, 3 or less, 2 or less, or 1 or less, e.g., from 0.5 to 100, from 0.5 to 50, from 0.5 to 10, from 0.5 to 5, from 0.5 to 1, from 1 to 5, from 2 to 4, from 5 to 100, from 10 to 70, from 10 to 50, from 5 to 25, from 10 to 30, or from 50 to 100, from 60 to 80, or from 65 to 75. In certain embodiments, the molar ratio of the surfactant to mosunetuzumab is from 50 to 100. In some embodiments, the molar ratio of the surfactant to mosunetuzumab is from 50 to 100, from 60 to 80, or from 65 to 75, e.g., about 65, 66, 67, 68, 69, 70, 71, 72, 73, 74, or 75. In some embodiments, the DP may have a molar ratio of surfactant (e.g., PS20) to mosunetuzumab from 50 to 100. For example, in a particular embodiment, a DP may have a molar ratio of surfactant (e.g., PS20) to mosunetuzumab of about 71. In some embodiments, the DP may have a molar ratio of surfactant (e.g., P188) to mosunetuzumab from 5 to 25. For example, in a particular embodiment, a DP may have a molar ratio of surfactant (e.g., PS20) to mosunetuzumab of about 17.

The disclosed pharmaceutical compositions include a surfactant. Any suitable surfactant can be used. In some embodiments, the surfactant is preferably a nonionic surfactant (e.g., a polysorbate (a polyoxyethylene (n) sorbitan monolaurate), a poloxamer, a polyoxyethelene alkyl ether, an alkyl phenyl polyoxyethylene ether, or a combination thereof). In some embodiments, the nonionic surfactant is a polysorbate (e.g., polysorbate 20 (PS20; e.g., polyoxyethylene (20) sorbitan monolaurate, e.g., TWEEN 20®; e.g., Super Refined™ PS20 (a PS20 that has been subjected to proprietary flash chromatographic process for greater purity and is available from Avantor Performance Materials, LLC (Center Valley, PA, U.S.))) or polysorbate 80 (PS80; e.g., polyoxyethylene (20) sorbitan monooleate, e.g., TWEEN 80®; e.g., Super Refined™ PS80 (Avantor)). In a particular embodiment, the polysorbate is polysorbate 20 (PS20). In other embodiments, the nonionic surfactant is a poloxamer (e.g., poloxamer 188, poly(ethylene glycol)-block-poly(propylene glycol)-block-poly(ethylene glycol)).

Any suitable concentration of the surfactant may be used. The concentration of surfactant in the pharmaceutical composition can be selected based on the desired molar ratio of surfactant to mosunetuzumab. In some embodiments of any of the pharmaceutical compositions described herein, the concentration of the surfactant (e.g., PS20 or P188) is about 0.001% (w/v) to about 2% (w/v), e.g., about 0.001%, about 0.005%, about 0.01%, about 0.02%, about 0.03%, about 0.04%, about 0.05%, about 0.06%, about 0.07%, about 0.08%, about 0.09%, about 0.1%, about 0.15%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, or about 2% (w/v). In some embodiments, the concentration of the surfactant (e.g., PS20 or P188) is about 0.01% (w/v) to about 0.1% (w/v). In some embodiments, the concentration of the surfactant (e.g., PS20 or P188) is about 0.05% (w/v) to about 0.1% (w/v). In a particular embodiment, the surfactant is PS20, and the concentration of PS20 is about 0.06% (w/v). In certain embodiments, the surfactant is P188, and the concentration of P188 is about 0.1% (w/v).

Any of the pharmaceutical compositions described herein can include a stabilizer. Any suitable stabilizer can be used. For example, in some embodiments, the stabilizer is thiosorbitol, ascorbic acid, monothioglycerol, a cyclodextrin, Trolox ((±)-6-hydroxy-2,5,7,8-tetramethylchroman-2-carboxylic acid), pyridoxine, mannitol, a metal chelator, an amino acid, or a combination thereof. In some embodiments, the stabilizer is an amino acid. In some embodiments, the amino acid is methionine, cysteine, tryptophan, or a combination thereof. In a particular embodiment, the amino acid is methionine.

Any suitable concentration of the stabilizer (e.g., methionine) may be used. For example, in some embodiments of any of the preceding pharmaceutical compositions, the concentration of the stabilizer (e.g., methionine) is about 0.01 mM to about 50 mM, e.g., about 0.01 mM, about 0.05 mM, about 0.1 mM, about 0.2 mM, about 0.3 mM, about 0.4 mM, about 0.5 mM, about 0.6 mM, about 0.7 mM, about 0.8 mM, about 0.9 mM, about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM, or about 50 mM. In some embodiments, the concentration of the stabilizer (e.g., methionine) is about 1 mM to about 50 mM, about 2 mM to about 50 mM, about 3 mM to about 50 mM, about 4 mM to about 50 mM, about 5 mM to about 50 mM, about 6 mM to about 50 mM, about 7 mM to about 50 mM, about 8 mM to about 50 mM, about 9 mM to about 50 mM, about 10 mM to about 50 mM, about 15 mM to about 50 mM, about 20 mM to about 50 mM, about 25 mM to about 50 mM, about 30 mM to about 50 mM, about 1 mM to about 40 mM, about 2 mM to about 40 mM, about 3 mM to about 40 mM, about 4 mM to about 40 mM, about 5 mM to about 40 mM, about 5 mM to about 40 mM, about 6 mM to about 40 mM, about 7 mM to about 40 mM, about 8 mM to about 40 mM, about 9 mM to about 40 mM, about 10 mM to about 40 mM, about 15 mM to about 40 mM, about 20 mM to about 40 mM, about 25 mM to about 40 mM, about 30 mM to about 40 mM, about 1 mM to about 30 mM, about 2 mM to about 30 mM, about 3 mM to about 30 mM, about 4 mM to about 30 mM, about 5 mM to about 30 mM, about 6 mM to about 30 mM, about 7 mM to about 30 mM, about 8 mM to about 30 mM, about 9 mM to about 30 mM, about 10 mM to about 30 mM, about 11 mM to about 30 mM, about 12 mM to about 30 mM, about 13 mM to about 30 mM, about 14 mM to about 30 mM, about 15 mM to about 30 mM, about 20 mM to about 30 mM, about 25 mM to about 30 mM, about 1 mM to about 20 mM, about 2 mM to about 20 mM, about 3 mM to about 20 mM, about 4 mM to about 20 mM, about 5 mM to about 20 mM, about 6 mM to about 20 mM, about 7 mM to about 20 mM, about 8 mM to about 20 mM, about 9 mM to about 20 mM, about 10 mM to about 20 mM, about 11 mM to about 20 mM, about 12 mM to about 20 mM, about 13 mM to about 20 mM, about 14 mM to about 20 mM, about 15 mM to about 20 mM, about 1 mM to about 15 mM, about 2 mM to about 15 mM, about 3 mM to about 15 mM, about 4 mM to about 15 mM, about 5 mM to about 15 mM, about 6 mM to about 15 mM, about 7 mM to about 15 mM, about 8 mM to about 15 mM, about 9 mM to about 15 mM, about 10 mM to about 15 mM, about 11 mM to about 15 mM, about 12 mM to about 15 mM, about 13 mM to about 15 mM, about 14 mM to about 15 mM, about 1 mM to about 10 mM, about 2 mM to about 10 mM, about 3 mM to about 10 mM, about 4 mM to about 10 mM, about 5 mM to about 10 mM, about 6 mM to about 10 mM, about 7 mM to about 10 mM, about 8 mM to about 10 mM, about 9 mM to about 10 mM, about 1 mM to about 5 mM, about 2 mM to about 5 mM, about 3 mM to about 5 mM, or about 4 mM to about 5 mM.

In some embodiments, the concentration of methionine is from 2.5 mM to 20 mM (e.g., from 2.5 mM to 5 mM, from 5 mM to 7.5 mM, from 7.5 mM to 10 mM, from 10 mM to 12.5 mM, from 12.5 mM to 15 mM, from 15 mM to 17.5 mM, or from 17.5 mM to 20 mM, e.g., from 3 mM to 18 mM, from 4 mM to 16 mM, from 5 mM to 14 mM, or from 8 mM to 12 mM, e.g., about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, or about 20 mM). In a particular embodiment, the concentration of methionine is about 10 mM.

In a pharmaceutical composition containing mosunetuzumab, oxidation of a methionine at position 257 of the Fc region is less than 10% (e.g., less than 9%, less than 8%, less than 7%, less than 6%, less than 5%, less than 4%, less than 3%, less than 2%, or less than 1%; e.g., 0-9%, 0-8%, 0-7%, 0-6%, 0-5%, 0-4%, 0-3%, 0-2%, 0-1%, 1-5%, 1-10%, 2-9%, 3-8%, or 4-7%; e.g., about 10%, about 9%, about 8%, about 7%, about 6%, about 4%, about 4%, about 3%, about 2%, about 1%, or about 0%) over two weeks at 40° C. In a particular embodiment, the oxidation of the methionine at position 257 of the Fc region is no more than about 6% (e.g., 0-6%) over two weeks at 40° C.

Any of the preceding compositions (e.g., pharmaceutical compositions) can further include a buffering agent. Any suitable buffering agent can be used. In some embodiments, the buffering agent is histidine, an acetate, a phosphate, a succinate, or a combination thereof. In some embodiments, the histidine is a histidine acetate. Alternative buffering agents include sodium phosphate monobasic, sodium phosphate dibasic, sodium phosphate tribasic, potassium phosphate monobasic, potassium phosphate dibasic, potassium phosphate tribasic, or a mixture thereof.

In certain instances, the concentration of the buffering agent (e.g., histidine, e.g., histidine acetate) is from 5 mM to 20 mM. For example, the buffering agent can be from 5 mM to 10 mM, from 10 mM to 15 mM, or from 15 mM to 20 mM, e.g., from 6 mM to 18 mM, from 7 mM to 16 mM, from 8 mM to 15 mM, from 9 mM to 12 mM, or from 8 mM to 12 mM, e.g., about 5 mM, about 6 mM, about 7 mM, about 8 mM, about 9 mM, about 10 mM, about 11 mM about 12 mM, about 13 mM, about 14 mM, about 15 mM, about 16 mM, about 17 mM, about 18 mM, about 19 mM, or about 20 mM. In particular instances, the concentration of the buffering agent (e.g., histidine, e.g., histidine acetate) can be, e.g., from 8 mM to 12 mM, e.g., about 8 mM, about 9 mM, about 10 mM, about 11 mM, or about 12 mM. In a particular embodiment, the concentration of the buffering agent (e.g., histidine, e.g., histidine acetate) is about 10 mM. In a particular embodiment, the buffering agent is L-histidine acetate and present at a concentration of about 10 mM.

In some embodiments, the pharmaceutical composition includes a tonicity agent, such as a carbohydrate (e.g., sucrose, glucose, dextrose, glycerol, glycerin, mannitol, and trehalose), an amino acid, or a salt (e.g., sodium chloride and potassium chloride). In embodiments in which the tonicity agent is a sugar, the sugar can be, e.g., sucrose, glucose, glycerol, or trehalose. In a particular embodiment, the sugar is sucrose. The concentration of the tonicity agent (e.g., sugar, e.g., sucrose) can be from about 100 mM to about 500 mM. For example, the concentration of the tonicity agent (e.g., sugar, e.g., sucrose) can be from 100 mM to 120 mM, from 120 mM to 140 mM, from 140 mM to 160 mM, from 160 mM to 180 mM, from 180 mM to 200 mM, from 200 mM to 220 mM, from 220 mM to 240 mM, from 240 mM to 260 mM, from 260 mM to 280 mM, from 280 mM to 300 mM, from 300 mM to 320 mM, from 320 mM to 340 mM, from 340 mM to 360 mM, from 360 mM to 380 mM, from 380 mM to 400 mM, from 400 mM to 420 mM, from 420 mM to 440 mM, from 440 mM to 460 mM, from 460 mM to 480 mM, or from 480 mM to 500 mM, e.g., from 100 mM to 400 mM, from 150 mM to 350 mM, or from 200 mM to 300 mM, e.g., about 100 mM, about 150 mM, about 200 mM, about 210 mM, about 220 mM, about 230 mM, about 240 mM, about 250 mM, about 260 mM, about 270 mM, about 280 mM, about 290 mM, about 300 mM, about 350 mM, about 400 mM, about 450 mM, or about 500 mM). In some embodiments, the concentration of the tonicity agent is about 240 mM. In a particular embodiment, the tonicity agent is sucrose and present at a concentration of about 240 mM.

The pH of the pharmaceutical compositions can be any suitable pH. In some embodiments, the pharmaceutical composition has a pH range from about 4.5 to about 8 (e.g., from 4.5 to 5.0, from 5.0 to 5.5, from 5.5 to 6.0, from 6.0 to 6.5, from 6.5 to 7.0, from 7.0 to 7.5, or from 7.5 to 8.0, e.g., about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0). In some embodiments, the pH of the pharmaceutical composition is from 5.5 to 6.1. In a particular embodiment, the pH of the pharmaceutical composition is about 5.8.

In addition to the specific components described above, the pharmaceutical compositions of the disclosure can also be optionally prepared by mixing mosunetuzumab having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the used dosages and concentrations employed, and include, but are not limited to: buffers, such as phosphate, citrate, and other organic acids; antioxidants, including ascorbic acid and methionine; preservatives, such as octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol, m-Cresol; low molecular weight (less than about 10 residues) polypeptides; proteins, such as serum albumin, gelatin, or immunoglobulins; hydrophilic polymers, such as polyvinylpyrrolidone; amino acids such as glycine, glutamine, asparagine, histidine, arginine, or lysine; carbohydrates, such as monosaccharides (e.g., glucose, mannose), disaccharides (e.g., sucrose, trehalose), or polysaccharides (e.g., dextrins), or sugar alcohols, such as mannitol or sorbitol; chelating agents such as ethylenediaminetetraacetic acid (EDTA); salt-forming counter-ions such as sodium; metal complexes (e.g., Zn-protein complexes); and/or non-ionic surfactants such as polyethylene glycol (PEG). Exemplary pharmaceutically acceptable carriers include interstitial drug dispersion agents, such as soluble neutral-active hyaluronidase glycoproteins (sHASEGP's), for example, human soluble PH-20 hyaluronidase glycoproteins, such as rHuPH20 (HYLENEX®, Baxter International, Inc.). Certain exemplary sHASEGPs and methods of use, including rHuPH20, are described in U.S. Pat. Pub. Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine acetate buffer.

In some embodiments, the pharmaceutical composition is in a unit dosage form (e.g., liquid formulation for infusion, liquid formulation for injection, or liquid formulation for dilution). In a particular embodiment, the pharmaceutical composition is a liquid formulation for dilution. In a particular embodiment, the liquid formulation for dilution is supplied in a container having a volume of about 50 ml (e.g., about 40 ml, about 45 ml, about 46 ml, about 47 ml, about 48 ml, about 49 ml, about 50 ml, about 51 ml, about 52 ml, about 53 ml, about 54 ml, about 55 ml, or about 60 ml). In some embodiments, the volume of the liquid formulation for dilution is between 20-40 ml (e.g., between 20-30 ml, between 30-40 ml, between 20-35 ml, between 25-40 ml, between 25-35 ml, or between 28-32 ml; e.g., about 20 ml, about 25 ml, about 26 ml, about 27 ml, about 28 ml, about 29 ml, about 30 ml, about 31 ml, about 32 ml, about 33 ml, about 34 ml, about 35 ml, or about 40 ml). In a particular embodiment, the volume of the liquid formulation for dilution is about 30 ml. In another particular embodiment, the liquid formulation for dilution is supplied in a container having a volume of about 2 ml (e.g., about 1 ml, about 1.5 ml, about 1.6 ml, about 1.7 ml, about 1.8 ml, about 1.9 ml, about 2 ml, about 2.1 ml, about 2.2 ml, about 2.3 ml, about 2.4 ml, about 2.5 ml, or about 3 ml). In some embodiments, the volume of the liquid formulation for dilution is between 0.2-2 ml (e.g., between 0.2-1.5 ml, between 0.5-2 ml, between 0.5-1 ml, or between 0.8-1.2 ml; e.g., about 0.2 ml, about 0.5 ml, about 0.6 ml, about 0.7 ml, about 0.8 ml, about 0.9 ml, about 1 ml, about 1.1 ml, about 1.2 ml, about 1.3 ml, about 1.4 ml, about 1.5 ml, or about 2 ml). In a particular embodiment, the volume of the liquid formulation for dilution is about 1 ml.

In some embodiments, the liquid formulation is for dilution with a diluent. In some embodiments, the liquid formulation is for dilution with a saline solution. In some embodiments, the liquid formulation is for dilution with a normal saline solution. In some embodiments, the normal saline solution comprises sodium chloride (NaCl). In some embodiments, the normal saline solution comprises between 0.1-1.5% (e.g., between 0.1-1.2%, between 0.3-1.5%, between 0.4-0.5%, between 0.3-1%, between 0.8-1%, between 0.85-0.95%; e.g., about 0.1%, about 0.3%, about 0.4%, about 0.45%, about 0.5%, about 0.6%, about 0.7%, about 0.8%, about 0.85%, about 0.9%, about 0.95%, about 1%, or about 1.2%) (w/v) NaCl).

The formulation herein may also contain more than one active ingredient as necessary for the particular indication being treated, preferably those with complementary activities that do not adversely affect each other. For example, it may be desirable to further provide an additional therapeutic agent (e.g., a chemotherapeutic agent, a cytotoxic agent, a growth inhibitory agent, and/or an anti-hormonal agent, such as those recited herein above). Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, for example, films, or microcapsules.

The formulations to be used for in vivo administration are generally sterile. Sterility may be readily accomplished, e.g., by filtration through sterile filtration membranes.

Any of the pharmaceutical compositions described herein can have a shelf-life of at least about 12 months (e.g., at least about 12 months, at least about 18 months, at least about 24 months, at least about 30 months, at least about 36 months, at least about 42 months, at least about 48 months, at least about 54 months, at least about 60 months, at least about 66 months, or at least about 72 months) when stored at 5° C.±3°

C. and protected from light. In some embodiments, the pharmaceutical composition has a shelf-life of at least 36 months when stored at 5° C.±3° C. and protected from light. In some embodiments, the composition has a shelf-life of at least 42 months when stored at 5° C.±3° C. and protected from light. In some embodiments, the composition has a shelf-life of at least 48 months when stored at 5° C.±3° C. and protected from light.

In some embodiments, the shelf-life when stored at 5° C.±3° C. and protected from light is between about 1 month and about 72 months (e.g., about 1 month, about 5 months, about 10 months, about 15 months, about 20 months, about 24 months, about 25 months, about 30 months, about 35 months, about 40 months, about 45 months, about 48 months, about 50 months, about 55 months, about 60 months, about 65 months, about 70 months, or about 72 months). In some embodiments, the shelf-life when stored at 5° C.±3° C. and protected from light is between about 1 month and about 72 months, about 1 month and about 70 months, about 1 month and about 65 months, about 1 month and about 60 months, about 1 month and about 55 months, about 1 month and about 50 months, about 1 month and about 48 months, about 1 month and about 45 months, about 1 month and about 40 months, about 1 month and about 35 months, about 1 month and about 30 months, about 1 month and about 25 months, about 1 month and about 24 months, about 1 month and about 20 months, about 1 month and about 18 months, about 1 month and about 15 months, about 1 month and about 12 months, about 1 month and about 9 months, about 1 month and about 6 months, about 1 month and about 3 months, about 5 months and about 72 months, about 5 months and about 70 months, about 5 months and about 65 months, about months and about 60 months, about 5 months and about 55 months, about 5 months and about 50 months, about 5 months and about 48 months, about 5 months and about 45 months, about 5 months and about 40 months, about 5 months and about 35 months, about 5 months and about 30 months, about months and about 25 months, about 5 months and about 24 months, about 5 months and about 20 months, about 5 months and about 18 months, about 5 months and about 15 months, about 5 months and about 12 months, about 5 months and about 9 months, about 5 months and about 6 months, about months and about 72 months, about 10 months and about 70 months, about 10 months and about 65 months, about 10 months and about 60 months, about 10 months and about 55 months, about 10 months and about 50 months, about 10 months and about 48 months, about 10 months and about 45 months, about 10 months and about 40 months, about 10 months and about 35 months, about 10 months and about 30 months, about 10 months and about 25 months, about 10 months and about 24 months, about months and about 20 months, about 10 months and about 18 months, about 10 months and about 15 months, about 10 months and about 12 months, about 12 months and about 72 months, about 12 months and about 70 months, about 12 months and about 65 months, about 12 months and about 60 months, about 12 months and about 55 months, about 12 months and about 50 months, about 12 months and about 48 months, about 12 months and about 45 months, about 12 months and about 40 months, about 12 months and about 35 months, about 12 months and about 30 months, about 12 months and about 25 months, about 12 months and about 24 months, about 12 months and about 20 months, about 12 months and about 18 months, about 12 months and about 15 months, about 18 months and about 72 months, about 18 months and about 70 months, about 18 months and about 65 months, about 18 months and about 60 months, about 18 months and about 55 months, about 18 months and about 50 months, about 18 months and about 48 months, about 18 months and about 45 months, about 18 months and about 40 months, about 18 months and about 35 months, about 18 months and about 30 months, about 18 months and about 25 months, about 18 months and about 24 months, about 18 months and about 20 months, about 24 months and about 72 months, about 24 months and about 70 months, about 24 months and about 65 months, about 24 months and about 60 months, about 24 months and about 55 months, about 24 months and about 50 months, about 24 months and about 48 months, about 24 months and about 45 months, about 24 months and about 40 months, about 24 months and about 35 months, about 24 months and about 30 months, about 24 months and about 25 months, about 30 months and about 72 months, about 30 months and about 70 months, about 30 months and about 65 months, about 30 months and about 60 months, about 30 months and about 55 months, about 30 months and about 50 months, about 30 months and about 48 months, about 30 months and about 45 months, about 30 months and about 40 months, about 30 months and about 35 months, about 30 months and about 36 months, about 36 months and about 72 months, about 36 months and about 70 months, about 36 months and about 65 months, about 36 months and about 60 months, about 36 months and about 55 months, about 36 months and about 50 months, about 36 months and about 48 months, about 36 months and about 45 months, about 36 months and about 40 months, about 40 months and about 72 months, about 40 months and about 70 months, about 40 months and about 65 months, about 40 months and about 60 months, about 40 months and about 55 months, about 40 months and about 50 months, about 40 months and about 48 months, about 40 months and about 45 months, about 42 months and about 72 months, about 42 months and about 70 months, about 42 months and about 65 months, about 42 months and about 60 months, about 42 months and about 55 months, about 42 months and about 50 months, about 42 months and about 48 months, about 42 months and about 45 months, about 46 months and about 72 months, about 46 months and about 70 months, about 46 months and about 65 months, about 46 months and about 60 months, about 46 months and about 55 months, about 46 months and about 50 months, about 46 months and about 48 months, about 48 months and about 72 months, about 48 months and about 70 months, about 48 months and about 65 months, about 48 months and about 60 months, about 48 months and about 55 months, about 48 months and about 50 months, about 50 months and about 72 months, about 50 months and about 70 months, about 50 months and about 65 months, about 50 months and about 60 months, about 50 months and about 55 months, about 55 months and about 72 months, about 55 months and about 70 months, about 55 months and about 65 months, about 55 months and about 60 months, about 60 months and about 72 months, about 60 months and about 70 months, or about 60 months and about 65 months.

A stable pharmaceutical composition may include, e.g., no more than 1,000 particles having a diameter ≥2 μm per ml. For example, a pharmaceutical composition may have 900 or fewer, 800 or fewer, 700 or fewer, 600 or fewer, 500 or fewer, 400 or fewer, 300 or fewer, 200 or fewer, or 100 or fewer particles having a diameter ≥2 μm per ml (e.g., from 0 to 100, from 100 to 200, from 200 to 300, from 300 to 400, from 400 to 500, from 500 to 600, from 600 to 700, from 700 to 800, from 800 to 900, or from 900 to 1,000 particles having a diameter ≥2 μm per ml). In some embodiments, the carrier is water.

Additionally or alternatively, a stable pharmaceutical can have a purity of about 85% or higher. In some embodiments, the purity is about 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, e.g., from 85% to 90%, from 90% to 95%, or from 95% to 100%, e.g., as assessed by size-exclusion high performance liquid chromatography (SE-HPLC). In a particular embodiment, the pharmaceutical composition has a purity of about 90% or higher as assessed by SE-HPLC, or about 95% or higher as assessed by SE-HPLC. In some embodiments, the pharmaceutical composition has a purity of about 95% or higher as assessed by SE-HPLC for about 36 months or longer at about 5° C. (e.g., 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, as assessed by SE-HPLC for about 36 months or longer at about 5° C., e.g., from 85% to 90%, from 90% to 95%, or from 95% to 100%, as assessed by SE-HPLC for about 36 months or longer at about 5° C. In particular instances, a pharmaceutical composition has a purity of about 95% or higher as assessed by SE-HPLC for about 42 months or longer at about 5° C., e.g., for about 42 months, for about 60 months, for about 72 months, for about 84 months, for about 96 months, or longer, at about 5° C.

In some instances, the disclosure provides a pharmaceutical composition having a purity of about 75% or higher as assessed by non-reduced capillary electrophoresis sodium dodecyl sulfate (CE-SDS) assay (e.g., about 76% or higher, about 77% or higher, about 78% or higher, about 79% or higher, about 80% or higher, about 81% or higher, about 82% or higher, about 83% or higher, about 84% or higher, 85% or higher, about 86% or higher, about 87% or higher, about 88% or higher, about 89% or higher, about 90% or higher, about 91% or higher, about 92% or higher, about 93% or higher, about 94% or higher, about 95% or higher, about 96% or higher, about 97% or higher, about 98% or higher, about 99% or higher, as assessed by non-reduced CE-SDS assay, e.g., from 75% to 80%, from 80% to 85%, from 85% to 90%, from 90% to 95% or from 95% to 100%, as assessed by non-reduced CE-SDS assay). In a particular embodiment, the pharmaceutical composition has a purity of about 80% or higher as assessed by non-reduced CE-SDS assay. For example, in some embodiments, the pharmaceutical composition has a purity of about 85% or higher as assessed by non-reduced CE-SDS assay. In some embodiments, the pharmaceutical composition has a purity of about 85% or higher as assessed by non-reduced CE-SDS assay for about 36 months or longer at about 5° C. (e.g., 85% or higher, about 86% or higher, about 87% or higher, about 88% or higher, about 89% or higher, about 90% or higher, about 91% or higher, about 92% or higher, about 93% or higher, about 94% or higher, about 95% or higher, about 96% or higher, about 97% or higher, about 98% or higher, about 99% or higher, as assessed by non-reduced CE-SDS assay, e.g., from 85% to 90%, from 90% to 95%, or from 95% to 100%, as assessed by non-reduced CE-SDS assay for about 36 months or longer at about 5° C.). In some embodiments, the pharmaceutical composition has a purity of about 85% or higher as assessed by non-reduced CE-SDS assay for about 42 months or longer at about 5° C. (e.g., 85% or higher, about 86% or higher, about 87% or higher, about 88% or higher, about 89% or higher, about 90% or higher, about 91% or higher, about 92% or higher, about 93% or higher, higher, about 94% or higher, about 95% or higher, about 96% or higher, about 97% or higher, about 98% or higher, about 99% or higher, as assessed by non-reduced CE-SDS assay, e.g., from 85% to 90%, from 90% to 95%, or from 95% to 100%, as assessed by non-reduced CE-SDS assay for about 42 months or longer at about 5° C.).

III. Mosunetuzumab

Mosunetuzumab may incorporate any of the features, singly or in combination, as described herein.

In some instances, mosunetuzumab includes (1) an anti-CD20 arm having a first binding domain comprising at least one, two, three, four, five, or six HVRs selected from (a) an HVR-H1 comprising the amino acid sequence of GYTFT-SYNMH (SEQ ID NO: 1); (b) an HVR-H2 comprising the amino acid sequence of AIYPGNGDTSYNQKFKG (SEQ ID NO: 2); (c) an HVR-H3 comprising the amino acid sequence of VVYYSNSYWYFDV (SEQ ID NO: 3); (d) an HVR-L1 comprising the amino acid sequence of RASSSVSYMH (SEQ ID NO: 4); (e) an HVR-L2 comprising the amino acid sequence of APSNLAS (SEQ ID NO: 5); and (f) an HVR-L3 comprising the amino acid sequence of QQWSFNPPT (SEQ ID NO: 6); and (2) an anti-CD3 arm having a second binding domain comprising at least one, two, three, four, five, or six HVRs selected from (a) an HVR-H1 comprising the amino acid sequence of NYYIH (SEQ ID NO: 9); (b) an HVR-H2 comprising the amino acid sequence of WIYPGDGNTKYNEKFKG (SEQ ID NO: 10); (c) an HVR-H3 comprising the amino acid sequence of DSYSNYYFDY (SEQ ID NO: 11); (d) an HVR-L1 comprising the amino acid sequence of KSSQSLLNSRTRK-NYLA (SEQ ID NO: 12); (e) an HVR-L2 comprising the amino acid sequence of WASTRES (SEQ ID NO: 13); and (f) an HVR-L3 comprising the amino acid sequence of TQSFILRT (SEQ ID NO: 14). In some instances, mosunetuzumab comprises (1) an anti-CD20 arm comprising at least one (e.g., 1, 2, 3, or 4) of heavy chain framework regions FR-H1, FR-H2, FR-H3, and FR-H4 comprising the sequences of SEQ ID NOs: 17-20, respectively, and/or at least one (e.g., 1, 2, 3, or 4) of the light chain framework regions FR-L1, FR-L2, FR-L3, and FR-L4 comprising the sequences of SEQ ID NOs: 21-24, respectively, and (2) an anti-CD3 arm comprising at least one (e.g., 1, 2, 3, or 4) of heavy chain framework regions FR-H1, FR-H2, FR-H3, and FR-H4 comprising the sequences of SEQ ID NOs: 25-28, respectively, and/or at least one (e.g., 1, 2, 3, or 4) of the light chain framework regions FR-L1, FR-L2, FR-L3, and FR-L4 comprising the sequences of SEQ ID NOs: 29-32, respectively. In some instances, mosunetuzumab comprises (1) an anti-CD20 arm comprising a first binding domain comprising (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 7; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 8; or (c) a VH domain as in (a) and a VL domain as in (b), and (2) an anti-CD3 arm comprising a second binding domain comprising (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 15; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 16; or (c) a VH domain as in (a) and a VL domain as in (b). In some instances, mosunetuzumab comprises (1) an anti-CD20 arm comprising a first binding domain comprising a VH domain comprising an amino acid sequence of SEQ ID NO: 7 and a VL domain comprising an amino acid sequence of SEQ ID NO: 8 and (2) an anti-CD3 arm comprising a second binding domain comprising a VH domain comprising an amino acid sequence of SEQ ID NO: 15 and a VL domain comprising an amino acid sequence of SEQ ID NO: 16.

In some instances, mosunetuzumab has the International Nonproprietary Names for Pharmaceutical Substances (INN) List 117 (WHO Drug Information, Vol. 31, No. 2, 2017, p. 303), or CAS Registry No. 1905409-39-3, and having (1) an anti-CD20 arm comprising the heavy chain and light chain sequences of SEQ ID NOs: 33 and 34, respectively; and (2) an anti-CD3 arm comprising the heavy chain and light chain sequences of SEQ ID NOs: 35 and 36, respectively.

In some instances, mosunetuzumab comprises (1) an anti-CD20 arm comprising a first binding domain comprising (a) α heavy chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 33; (b) a light chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 34; or (c) α heavy chain as in (a) and a light chain as in (b), and (2) an anti-CD3 arm comprising a second binding domain comprising (a) α heavy chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 35; (b) a light chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 36; or (c) α heavy chain as in (a) and a light chain as in (b). In some instances, mosunetuzumab comprises (1) an anti-CD20 arm comprising a first binding domain comprising α heavy chain comprising an amino acid sequence of SEQ ID NO: 33 and a light chain comprising an amino acid sequence of SEQ ID NO: 34 and (2) an anti-CD3 arm comprising a second binding domain comprising α heavy chain comprising an amino acid sequence of SEQ ID NO: 35 and a light chain comprising an amino acid sequence of SEQ ID NO: 36.

Amino acid sequences of mosunetuzumab are summarized in Table 1 below.

TABLE 1

| Sequence IDs for Mosunetuzumab | | | |
|---|---|---|---|
| CD3 Arm | | CD20 Arm | |
| SEQ ID NO: | Description | SEQ ID NO: | Description |
| 9 | CD3 HVR-H1 | 1 | CD20 HVR-H1 |
| 10 | CD3 HVR-H2 | 2 | CD20 HVR-H2 |
| 11 | CD3 HVR-H3 | 3 | CD20 HVR-H3 |
| 12 | CD3 HVR-L1 | 4 | CD20 HVR-L1 |
| 13 | CD3 HVR-L2 | 5 | CD20 HVR-L2 |
| 14 | CD3 HVR-L3 | 6 | CD20 HVR-L3 |

TABLE 1-continued

| Sequence IDs for Mosunetuzumab | | | |
|---|---|---|---|
| CD3 Arm | | CD20 Arm | |
| SEQ ID NO: | Description | SEQ ID NO: | Description |
| 15 | CD3 VH | 7 | CD20 VH |
| 16 | CD3 VL | 8 | CD20 VL |
| 35 | CD3 heavy chain | 33 | CD20 heavy chain |
| 36 | CD3 light chain | 34 | CD20 light chain |

Mosunetuzumab may be produced using recombinant methods and compositions, for example, as described in U.S. Pat. No. 4,816,567.

IV. Recombinant Methods and Compositions

Mosunetuzumab may be produced using recombinant methods and compositions, for example, as described in U.S. Pat. No. 4,816,567. In one embodiment, an isolated nucleic acid or one or more isolated nucleic acids encoding mosunetuzumab described herein is provided. In some embodiments, such nucleic acid(s) may encode an amino acid sequence comprising the VL and/or an amino acid sequence comprising the VH of mosunetuzumab (e.g., the light and/or heavy chains of mosunetuzumab). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of mosunetuzumab and an amino acid sequence comprising the VH of mosunetuzumab, or (2) a first vector comprising a nucleic acid that encodes an amino acid sequence comprising the VL of mosunetuzumab and a second vector comprising a nucleic acid that encodes an amino acid sequence comprising the VH of mosunetuzumab. In one embodiment, the host cell is eukaryotic, e.g., a Chinese Hamster Ovary (CHO) cell or lymphoid cell (e.g., Y0, NS0, or Sp2/0 cell). Antibodies can be made by culturing a host cell comprising a nucleic acid encoding mosunetuzumab, as provided above, under conditions suitable for expression of the antibody, and optionally recovering mosunetuzumab from the host cell (or host cell culture medium).

For recombinant production of mosunetuzumab, one or more nucleic acids encoding mosunetuzumab, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of an antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. See also Charlton, *Methods in Molecular Biology*, Vol. 248 (B. K. C. Lo, ed., Humana Press, Totowa, NJ, 2003), pp. 245-254, describing expression of antibody fragments in *E. coli*. After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, NJ), pp. 255-268 (2003).

V. Assays

Mosunetuzumab of the pharmaceutical compositions of the disclosure may be identified, screened for, or characterized for its physical/chemical properties and/or biological activities by various assays known in the art and described herein.

1. Binding Assays

In one aspect, mosunetuzumab of the pharmaceutical compositions of the disclosure is tested for its antigen binding activity, for example, by known methods such as ELISA, Western blot, etc.

For example, competition assays can be used to identify an antibody that competes with mosunetuzumab for binding to its antigen. In an exemplary competition assay configured to characterize binding to CD3, immobilized CD3 is incubated in a solution comprising a first labeled antibody that binds to CD3 and a second unlabeled antibody that is being tested for its ability to compete with the first antibody for binding to CD3. The second antibody may be present in a hybridoma supernatant. As a control, immobilized CD3 is incubated in a solution comprising the first labeled antibody but not the second unlabeled antibody. After incubation under conditions permissive for binding of the first antibody to CD3, excess unbound antibody is removed, and the amount of label associated with immobilized CD3 is measured. If the amount of label associated with immobilized CD3 is substantially reduced in the test sample relative to the control sample, then that indicates that the second antibody is competing with the first antibody for binding to CD3. See, e.g., Harlow and Lane (1988) *Antibodies: A Laboratory Manual.* Ch. 14 (Cold Spring Harbor Laboratory, Cold Spring Harbor, NY).

2. Activity Assays

In one aspect, assays are provided for identifying antibodies thereof having biological activity. Biological activity may include, for example, binding to an antigen, such as CD3 (e.g., CD3 on the surface of a T cell), or a peptide fragment thereof, either in vivo, in vitro, or ex vivo. In the case of mosunetuzumab, biological activity may also include, for example, effector cell activation (e.g., T cell (e.g., CD8+ and/or CD4+ T cell) activation), effector cell population expansion (i.e., an increase in T cell count), target cell (e.g., CD20-positive cell) population reduction (i.e., a decrease in the population of cells expressing CD20 on their cell surfaces), and/or target cell killing. Antibodies having such biological activity in vivo and/or in vitro are provided.

In some embodiments, antibody activity includes the ability to support B cell killing and/or the activation of the cytotoxic T cells. In certain embodiments, mosunetuzumab is tested for such B cell killing and/or the activation of the cytotoxic effect of T cells biological activity by any of the methods described herein, in particular the Examples. In some embodiments of any of these activity assays, PBMCs may be isolated from whole blood of healthy donors by FICOLL® separation. In particular, human blood may be collected in heparinized syringes, and PBMCs isolated using Leucosep and FICOLL-PAQUE® Plus. If needed CD4+ T and CD8+ T cells may be separated with MILTENYI® kits according to manufacturer's instructions.

Cells may be washed in RPMI medium containing 10% FBS, supplemented with GlutaMax™, penicillin & streptomycin, and ~0.2 million suspended cells added to a 96-well U-bottom plate. Cells may be cultured in RPMI1640 supplemented with 10% FBS at 37° C. in a humidified standard cell culture incubator. For BJAB cell killing assays, 20,000 BJAB cells may be incubated with effector cells, either as huPBMCs or purified T cells, as indicated ratios per assay, in the presence of various concentrations of mosunetuzumab for 24 hours. For endogenous B cell killing assays, 200,000 huPBMCs may be incubated with various concentrations of mosunetuzumab for 24 hours.

After culturing, cells can be washed with FACS buffer (0.5% BSA, 0.05% Na azide in PBS). Cells may then be stained in FACS buffer, washed with FACS buffer and suspended in 100 μl of FACS buffer containing 1 μg/ml propidium iodide. Data may be collected on a FACSCalibur™ flow cytometer and analyzed using FLOWJO®. Live B cells may be gated out as PI-CD19+ or PI-CD20+ B cells by FACS, and absolute cell count may be obtained with FITC beads added to reaction mix as an internal counting control. The percent (%) of cell killing may be calculated based on non-mosuentuzumab treated controls. Activated T cells may be detected by CD69 and CD25 surface expression using anti-CD69-FITC and anti-CD25-PE.

3. Stability Assays

Suitable assays for determining the stability of a pharmaceutical composition (e.g., of mosunetuzumab) are known in the art and are described herein. For example, a pharmaceutical composition can be evaluated qualitatively and/or quantitatively in a variety of different ways, including evaluation of aggregate formation (for example, using size exclusion chromatography, by measuring turbidity, and/or by visual inspection); evaluation of reactive oxygen species (ROS) formation (for example, by using a light stress assay or an 2,2'-azobis(2-amidinopropane) dihydrochloride (AAPH) stress assay); oxidation of specific amino acid residues of the protein (for example, a Met residue of an antibody); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact polypeptides (e.g., antibodies); peptide map (for example, tryptic or LYS-C) analysis; evaluating biological activity or target binding function of the protein (e.g., binding of an antibody to its antigen); and the like. Instability may involve any one or more of: aggregation, deamidation (e.g., Asn deamidation), oxidation (e.g., Met oxidation), isomerization (e.g., Asp isomerization), clipping/hydrolysis/fragmentation (e.g., hinge region fragmentation), succinimide formation, unpaired cysteine(s), N-terminal extension, C-terminal processing, glycosylation differences, and the like. Exemplary assays are described in the Examples below.

VI. Therapeutic Methods and Uses

The pharmaceutical compositions (i.e., comprising mosunetuzumab) described herein can be formulated for use as a medicament for treating cancer. Thus, the disclosure features methods involving administration of the pharmaceutical composition to a subject in need thereof, e.g., a subject having cancer. A pharmaceutical composition of the present disclosure may be used to treat or delay progression of a cancer in a subject in need thereof (e.g., a human subject in need thereof) or to enhance immune function in a subject having a cancer.

In some embodiments, mosunetuzumab binds to a CD3 molecule located on an immune effector cell and a CD20 molecule located on a target cell (e.g., CD20-positive cell) other than the immune effector cell (e.g., a CD20 molecule located on (e.g., expressed by) a target cell (e.g., CD20-positive cell), such as a B cell. In some embodiments, mosunetuzumab activates the immune effector cell following binding to the CD3 molecule and to CD20. Upon activation, the immune effector cell can exert a cytotoxic effect and/or an apoptotic effect on the target cell (e.g., CD20-positive cell).

In some embodiments, the cancer is a non-Hodgkin's lymphoma (NHL). In some embodiments, the NHL is selected from the group consisting of chronic lymphoid leukemia (CLL), B cell lymphoma, splenic diffuse red pulp small B cell lymphoma, B cell lymphoma with features intermediate between diffuse large B cell lymphoma and Burkitt lymphoma, Burkitt-like lymphoma with 11q aberration, B cell lymphoma with features intermediate between diffuse large B cell lymphoma and classical Hodgkin lymphoma, diffuse large B cell lymphoma (DLBCL), germinal center B cell-like (GCB) diffuse large B cell lymphoma (DLBCL), activated B cell-like (ABC) DLBCL, primary cutaneous follicle center lymphoma, T-cell/histiocyte-rich large B cell lymphoma, primary DLBCL of the central nervous system, primary cutaneous DLBCL (leg type), Epstein-Barr virus (EBV)-positive DLBCL of the elderly, DLBCL associated with chronic inflammation, primary mediastinal (thymic) large B cell lymphoma, intravascular large B cell lymphoma, ALK-positive large B cell lymphoma, large B cell lymphoma arising in HHV8-associated multicentric Castleman disease, B cell leukemia, follicular lymphoma (FL), in situ follicular neoplasia, mantle cell lymphoma (MCL), in situ mantle cell neoplasia, acute myeloid leukemia (AML), marginal zone lymphoma (MZL), small lymphocytic leukemia (SLL), lymphoplasmacytic lymphoma (LL), Waldenstrom macroglobulinemia (WM), central nervous system lymphoma (CNSL), Burkitt's lymphoma (BL), B cell prolymphocytic leukemia, splenic marginal zone lymphoma, hairy cell leukemia, splenic lymphoma/leukemia, hairy cell leukemia variant, α heavy chain disease, γ heavy chain disease, µ heavy chain disease, plasma cell myeloma, solitary plasmacytoma of bone, extraosseous plasmacytoma, extranodal marginal zone lymphoma of mucosa-associated lymphoid tissue (MALT lymphoma), nodal marginal zone lymphoma, pediatric nodal marginal zone lymphoma, pediatric follicular lymphoma, lymphomatoid granulomatosis, plasmablastic lymphoma, and primary effusion lymphoma. In a particular embodiment, the cancer is germinal center B cell-like (GCB) DLBCL, activated B cell-like (ABC) DLBCL, follicular lymphoma (FL), mantle cell lymphoma (MCL), acute myeloid leukemia (AML), chronic lymphoid leukemia (CLL), marginal zone lymphoma (MZL), small lymphocytic leukemia (SLL), lymphoplasmacytic lymphoma (LL), Waldenstrom macroglobulinemia (WM), central nervous system lymphoma (CNSL), or Burkitt's lymphoma (BL).

In some embodiments, the NHL is DLBCL, GCB DLBCL, ABC DLBCL, FL, MCL, AML, CLL, MZL, SLL, LL, WM, CNSL, or BL. In some embodiments, the NHL is FL or DLBCL. In some embodiments, the NHL is relapsed and/or refractory (R/R). In some embodiments, the NHL is R/R NHL. In some embodiments, the R/R FL has relapsed after or is refractory to at least two (e.g., two, three, four, five, six, seven, eight, nine, ten, or more) prior systemic therapies. In some embodiments, the prior systemic therapy or therapies include an anti-CD20 monoclonal antibody. In some embodiments, the prior systemic therapy or therapies include an alkylating agent (e.g., bendamustine, chlorambucil, cyclophosphamide, ifosfamide, mechlorethamine, melphalan, carmustine, lomustine, streptozocin, busulfan, dacarbazine, temozolomide, altretamine, or thiotepa). In a particular embodiment, the prior systemic therapy or therapies include both an anti-CD20 monoclonal antibody and an alkylating agent.

In some embodiments, the cancer is selected from the group consisting of breast cancer, colorectal cancer, non-small cell lung cancer (NSCLC), multiple myeloma, renal cancer, prostate cancer, liver cancer, head and neck cancer, melanoma, ovarian cancer, mesothelioma, and glioblastoma.

Mosunetuzumab can be formulated for administration to the subject at a dose from about 0.1 mg to about 100 mg (e.g., from 0.1 mg to 80 mg, from 0.5 to 70 mg, from 1 mg to 60 mg, from 0.1 mg to 2 mg, from 0.5 mg to 1.5 mg, from 1 mg to 5 mg, from 1.5 mg to 2.5 mg, from 1 mg to 30 mg, from 15 mg to 45 mg, from 5 mg to 10 mg, from 10 mg to 15 mg, from 20 mg to 40 mg, to 20 mg to 30 mg, from 30 mg to 40 mg, from 25 mg to 35 mg, from 50 mg to 100 mg, from 50 mg to 60 mg, from 55 mg to 65 mg, from 60 mg to 70 mg, from 70 mg to 80 mg, from 80 mg to 90 mg, or from 90 to 100 mg, e.g., about 0.5 mg, about 1 mg, about 1.5 mg, about 2 mg, about 2.5 mg, about 3 mg, about 4 mg, about 5 mg, about 6 mg, about 7 mg, about 8 mg, about 9 mg, about 10 mg, about 11 mg, about 12 mg, about 13 mg, about 13.5 mg, about 14 mg, about 15 mg, about 16 mg, about 17 mg, about 18 mg, about 19 mg, about 20 mg, about 25 mg, about 30 mg, about 40 mg, about 45 mg, about 50 mg, about 60 mg, about 70 mg, about 75 mg, about 80 mg, about 90 mg, or about 100 mg). In some embodiments, the method includes administering mosunetuzumab to the subject at a dose from about 1 mg to about 60 mg. In particular embodiments, the method includes administering mosunetuzumab to the subject at a dose of about 1 mg, about 2 mg, about 6 mg, about 9 mg, about 13.5 mg, about 20 mg, about 30 mg, or about 60 mg. In some embodiments, the method includes administering mosunetuzumab to the subject at a dose of about 1 mg, 2 mg, 30 mg, or 60 mg.

In some embodiments, the pharmaceutical composition is administered to the subject after dilution with a saline solution. In some embodiments, the saline solution is a normal saline solution. In some embodiments, the normal saline solution comprises sodium chloride (NaCl). In some embodiments, the normal saline solution comprises between 0.1-1.5% (e.g., between 0.1-1.2%, between 0.3-1.5%, between 0.4-0.5%, between 0.3-1%, between 0.8-1%, between 0.85-0.95%; e.g., about 0.1%, about 0.3%, about 0.4%, about 0.45%, about 0.5%, about 0.6%, about 0.7%, about 0.8%, about 0.85%, about 0.9%, about 0.95%, about 1%, or about 1.2%) (w/v) NaCl). In particular embodiments, the normal saline solution comprises 0.45% or 0.9% (w/v) NaCl. In some embodiments, after dilution with the normal saline solution, the concentration of mosunetuzumab is from about 0.01 mg/ml to about 0.3 mg/ml (e.g., about 0.01 mg/ml, about 0.02 mg/ml, about 0.03 mg/ml, about 0.04 mg/ml, about 0.05 mg/ml, about 0.75 mg/ml, about 0.1 mg/ml, about 0.11 mg/ml, about 0.12 mg/ml, about 0.13 mg/ml, about 0.14 mg/ml, about 0.15 mg/ml, about 0.16 mg/ml, about 0.17 mg/ml, about 0.18 mg/ml, about 0.19 mg/ml, about 0.2 mg/ml, about 0.21 mg/ml, about 0.22 mg/ml, about 0.23 mg/ml, about 0.24 mg/ml, about 0.25 mg/ml, about 0.26 mg/ml, about 0.27 mg/ml, about 0.28 mg/ml, about 0.29 mg/ml, or about 0.3 mg/ml). In particular embodiments, after dilution with the normal saline solution, the concentration of mosunetuzumab is about 0.01 mg/ml, about 0.02 mg/ml, about 0.04 mg/ml, about 0.12 mg/ml, about 0.24 mg/ml, or about 0.3 mg/ml.

In one aspect, the pharmaceutical compositions (e.g., comprising mosunetuzumab) disclosed herein is administered to a subject in a dosing regimen comprising at least three 21-day (±3 days) dosing cycles, wherein (a) the first 21-day dosing cycle comprises a first dose (C1D1), a second dose (C1D2), and a third dose (C1D3) of mosunetuzumab administered to the subject on or about days 1, 8 (±1 day), and 15 (±1 day), respectively, of the first dosing cycle, wherein the C1D1 is about 1 mg (±0.5), the C1D2 is about 2 (±0.5) mg, and the C1D3 is about 60 (±5) mg; (b) the second dosing cycle comprises a single dose (C2D1) of mosunetuzumab administered to the subject on or about day 1 of the second dosing cycle, wherein the C2D1 is about 60 (±5) mg; and (c) the third dosing cycle comprises a single dose (C3D1) of mosunetuzumab administered to the subject on or about day 1 of the third dosing cycle, wherein the C3D1 is about 30 (±3) mg. In some embodiments, the dosing regimen comprises one to fourteen additional dosing cycles each comprising an additional single dose of about 30 (±0.5) mg of mosunetuzumab. In some embodiments, the dosing regimen comprises one to five (e.g., one, two, three, four, or five) additional dosing cycles. In a particular embodiment, the dosing regimen comprises five additional dosing cycles. In some embodiments, each additional single dose of mosunetuzumab is administered to the subject on or about day 1 of each respective additional dosing cycle.

The disclosure further provides methods for co-administration of the pharmaceutical composition (i.e., comprising mosunetuzumab) with at least one additional therapeutic agent (e.g., one, two, three, four, or more additional therapeutic agents) are also disclosed. For example, additional therapeutic agents include PD-1 axis binding antagonists, such as PD-L1 binding antagonists, PD-1 binding antagonists, and a PD-L2 binding antagonists. PD-L1 binding antagonists useful in the methods and pharmaceutical compositions include, e.g., atezolizumab (MPDL3280A), MDX-1105 (BMS-936559), and MED14736 (durvalumab). For example, in some particular instances, the anti-PD-L1 antibody is atezolizumab (CAS Registry Number: 1422185-06-5). MDX-1105, also known as BMS-936559, is an anti-PD-L1 antibody described in PCT Pub. No. WO 2007/005874 and PCT Pub. No. WO 2016/201425. MED14736 (durvalumab) is an anti-PD-L1 monoclonal antibody described in PCT Pub. No. WO 2011/066389 and U.S. Pub. No. 2013/034559. Examples of anti-PD-L1 antibodies useful for the methods of this disclosure, and methods for making them are described in PCT Pub. Nos. WO 2010/077634, WO 2007/005874, and WO 2011/066389, and also in U.S. Pat. No. 8,217,149, and U.S. Pub. No. 2013/034559, which are incorporated herein by reference.

PD-1 binding antagonists include anti-PD-1 antibodies, such as an anti-PD-1 antibody selected from the group consisting of MDX-1106 (nivolumab), MK-3475 (pembrolizumab), MEDI-0680 (AMP-514), PDR001, AMG 404, REGN2810 (cemiplimab; LIBTAYO®), and BGB-108. MDX-1106, also known as MDX-1106-04, ONO-4538, BMS-936558, or nivolumab, is an anti-PD-1 antibody described in PCT Pub. No. WO 2006/121168. MK-3475, also known as pembrolizumab or lambrolizumab, is an anti-PD-1 antibody described in PCT Pub. No. WO 2009/114335. In other instances, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In other instances, the PD-1 binding antagonist is REGN2810 (LIBTAYO®), also known as cemiplimab. In other instances, the PD-1 binding antagonist is AMP-224, a B7-DC Fc or PD-L2 Fc fusion protein described in PCT Pub. No. WO 2017/058780.

PD-L2 binding antagonists include, e.g., antibodies (e.g., an anti-PD-L2 antibody) and immunoadhesins. In some embodiments, an additional therapeutic agent includes obinutuzumab (an anti-CD20 antibody), rituximab (an anti-CD20 antibody), an antibody-drug conjugate (ADC), a corticosteroid, or tocilizumab (an anti-IL-6R antibody).

For example, an additional therapeutic agent useful for co-administration can be an ADC, such as an anti-CD79b ADC (e.g., polatuzumab vedotin; see, for example, *WHO Drug Information* (2012) vol. 26, No. 4, 437-438).

In instances for which the methods described herein involve a combination therapy, such as a particular combination therapy noted above, the combination therapy encompasses the co-administration of the pharmaceutical composition (i.e., comprising mosunetuzumab) with one or more additional therapeutic agents, and such co-administration may be combined administration or separate administration. Additionally, the two or more therapeutic agents may be formulated together or separately. In cases where two or more therapeutic agents are administered separately, administration of the pharmaceutical composition (i.e., comprising mosunetuzumab) can occur prior to, simultaneously, and/or following, administration of the additional therapeutic agent or agents.

The pharmaceutical compositions of the disclosure may be administered, for example, intravenously. In a particular embodiment, mosunetuzumab is administered intravenously. In particular, mosunetuzumab drug product is diluted in a saline solution (e.g., a normal saline solution) before administration. In some embodiments, the normal saline solution comprises sodium chloride (NaCl). In some embodiments, the normal saline solution comprises between 0.1-1.5% (e.g., between 0.1-1.2%, between 0.3-1.5%, between 0.4-0.5%, between 0.3-1%, between 0.8-1%, between 0.85-0.95%; e.g., about 0.1%, about 0.3%, about 0.4%, about 0.45%, about 0.5%, about 0.6%, about 0.7%, about 0.8%, about 0.85%, about 0.9%, about 0.95%, about 1%, or about 1.2%) (w/v) NaCl). For example, the following dilutions can be used to deliver the indicated dose using a drug product of 1 mg/ml mosunetuzumab (Table 2):

TABLE 2

Dilution of mosunetuzumab formulations (1 mg/ml drug product)

| Dose of mosun-etuzumab | Volume of mosunetuzumab in 0.9% or 0.45% sodium chloride solution | Size of infusion bag | Final concentration of mosunetuzumab |
|---|---|---|---|
| 1 mg | 1 ml | 50 ml or 100 ml | 0.02 mg/ml or 0.01 mg/ml |
| 2 mg | 2 ml | 50 ml or 100 ml | 0.04 mg/ml or 0.02 mg/ml |
| 30 mg | 30 ml | 100 ml or 250 ml | 0.3 mg/ml or 0.12 mg/ml |
| 60 mg | 60 ml | 250 ml | 0.24 mg/ml |

In one embodiment, administration of mosunetuzumab and administration of an additional therapeutic agent can occur within about one month, or within about one, two or three weeks, or within about one, two, three, four, five, or six days, of each other.

The methods described herein may result in an improved benefit-risk profile for patients having cancer being treated with mosunetuzumab. In some instances, treatment using the methods described herein that result in administering mosunetuzumab in the context of a fractionated, dose-escalation dosing regimen may result in a reduction (e.g., by 20% or greater, 25% or greater, 30% or greater, 35% or greater, 40% or greater, 45% or greater, 50% or greater, 55% or greater, 60% or greater, 65% or greater, 70% or greater, 75% or greater, 80% or greater, 85% or greater, 90% or greater, 95% or greater, 96% or greater, 97% or greater, 98% or greater, or 99% or greater) or complete inhibition (100% reduction) of undesirable events, such as cytokine-driven toxicities (e.g., cytokine release syndrome (CRS)), infusion-related reactions (IRRs), macrophage activation syndrome (MAS), neurologic toxicities, severe tumor lysis syndrome (TLS), neutropenia, thrombocytopenia, elevated liver enzymes, and/or central nervous system (CNS) toxicities, following treatment with mosunetuzumab using the fractionated, dose-escalation dosing regimen of the disclosure relative to treatment with mosunetuzumab using an non-fractioned dosing regimen.

For all the methods and pharmaceutical formulations described herein, mosunetuzumab would be formulated, dosed, and administered consistent with good medical practice. Factors for consideration in this context include the particular cancer being treated, the particular mammal being treated, the clinical condition of the individual patient, the cause of the cancer, the site of delivery of the agent, the method of administration, the scheduling of administration, and other factors known to medical practitioners. Mosunetuzumab need not be, but is optionally formulated with, one or more agents currently used to prevent or treat the cancer in question. The effective amount of such other agents depends on the amount of mosunetuzumab present in the formulation, the type of cancer or treatment, and other factors discussed above. Mosunetuzumab may be suitably administered to the patient over a series of treatments.

VII. Articles of Manufacture

In another aspect of the disclosure, an article of manufacture containing materials useful for the treatment, prevention, and/or diagnosis of the cancer described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a pharmaceutical composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is mosunetuzumab, as described herein. The label or package insert indicates that the composition is used for treating the condition of choice (e.g., a cancer) and further includes information related to at least one of the dosing regimens described herein.

The pharmaceutical composition can be supplied in a container having a volume from 1 ml to 100 ml (e.g., from 1 ml to 5 ml, from 5 ml to 10 ml, from 10 ml to 15 ml, from 15 ml to 20 ml, from 20 ml to 25 ml, from 25 ml to 30 ml, from 30 ml to 40 ml, from 40 ml to 50 ml, from 50 ml to 60 ml, from 60 ml to 70 ml, from 70 ml to 80 ml, from 80 ml to 90 ml, or from 90 ml to 100 ml, e.g., about 1 ml, about 2 ml, about 3 ml, about 4 ml, about 5 ml, about 10 ml, about 15 ml, about 20 ml, about 25 ml, about 30 ml, about 40 ml, about 50 ml, about 60 ml, about 70 ml, about 80 ml, about 90 ml, or about 100 ml). In a particular embodiment, the container has a volume of about 50 ml (e.g., about 40 ml, about 45 ml, about 46 ml, about 47 ml, about 48 ml, about 49 ml, about 50 ml, about 51 ml, about 52 ml, about 53 ml, about 54 ml, about 55 ml, or about 60 ml). In another particular embodiment, the container has a volume of about 2 ml (e.g., about 1 ml, about 1.5 ml, about 1.6 ml, about 1.7 ml, about 1.8 ml, about 1.9 ml, about 2 ml, about 2.1 ml, about 2.2 ml, about 2.3 ml, about 2.4 ml, about 2.5 ml, or about 3 ml).

In some embodiments, the container is a stainless-steel container or a nickel-steel alloy container (e.g., HASTELLOY®), such as a tank, mini-tank, canister, can, etc. In some instances, the pharmaceutical composition in such a container is a DS, which can be further diluted prior to use, e.g., into a DP (e.g., in final vial configuration). Alternatively, the pharmaceutical composition in the container is a DP. In some embodiments, if the DP is to be administered with a diluent (e.g., a saline solution; e.g., a normal saline solution; e.g., a normal saline solution comprising 0.45% or 0.9% (w/v) NaCl), or if it is intended to be administered in combination with other therapeutic reagents, the DP may be at a higher concentration than the concentration at which it is to be administered to the subject. In some embodiments, the DP is in a container such as an IV bag or a syringe (e.g., for delivery via syringe pump). In some embodiments, the DP can be diluted in an IV bag using a diluent (e.g., a saline solution; e.g., a normal saline solution; e.g., a normal saline solution comprising 0.45% or 0.9% (w/v) NaCl).

In some embodiments, the article of manufacture includes a vial (e.g., a glass vial) having a volume of about 1 ml or more, for example, about 1 ml, about 2 ml, about 3 ml, about 4 ml, about 5 ml, about 6 ml, about 7 ml, about 8 ml, about 9 ml, about 10 ml, about 11 ml, about 12 ml, about 13 ml, about 14 ml, about 15 ml, about 16 ml, about 17 ml, about 18 ml, about 19 ml, about 20 ml, about 25 ml, about 30 ml, about 35 ml, about 40 ml, about 50 ml, or more. In a particular embodiment, the vial has a volume of about 50 ml (e.g., about 40 ml, about 45 ml, about 46 ml, about 47 ml, about 48 ml, about 49 ml, about 50 ml, about 51 ml, about 52 ml, about 53 ml, about 54 ml, about 55 ml, or about 60 ml). In another particular embodiment, the vial has a volume of about 2 ml (e.g., about 1 ml, about 1.5 ml, about 1.6 ml, about 1.7 ml, about 1.8 ml, about 1.9 ml, about 2 ml, about 2.1 ml, about 2.2 ml, about 2.3 ml, about 2.4 ml, about 2.5 ml, or about 3 ml). In some embodiments, the vial is for single use. In some embodiments, the vial contains about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 30, about 45, about 60, or more of mosunetuzumab. In some embodiments, the vial includes a pharmaceutical composition comprising mosunetuzumab, polysorbate 20 (PS20), methionine, a buffering agent, and a carrier, wherein the molar ratio of the PS20 to mosunetuzumab is 100 or less, the concentration of PS20 is from 0.01% to 0.1% weight-by-volume (w/v), the concentration of methionine is from 1 mM to 50 mM, and the concentration of the buffering agent from 5 mM to 20 mM. In some embodiments, the container closure system comprises one or more, or all, of a glass vial, a stopper, and a cap.

Moreover, the article of manufacture may comprise (a) a first container with a composition contained therein, wherein the pharmaceutical composition comprises mosunetuzumab described herein; and (b) a second container with a pharmaceutical composition contained therein, wherein the pharmaceutical composition comprises a further cytotoxic or otherwise therapeutic agent. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents (e.g., a saline solution; e.g., a normal saline solution; e.g., a normal saline solution comprising 0.45% or 0.9% (w/v) NaCl), filters, needles, and syringes.

VIII. Examples

The following are examples of methods and compositions of the disclosure. It is understood that various other embodiments may be practiced, given the general description provided above, and the examples are not intended to limit the scope of the claims.

Example 1. Pharmaceutical Development

This example shows a method of formulating and using mosunetuzumab (BTCT4465A). For mosunetuzumab, the researchers observed that in the formulation, a relatively low protein concentration and relatively high surfactant concentration were considered preferable to ensure accurate delivery of low doses of mosunetuzumab.

Mosunetuzumab is based on a human IgG1 isotype and is intended for the treatment of B cell malignancies by T cell recruitment and activation. The CD20 arm of mosunetuzumab is directed against B-lymphocyte antigen CD20, a glycosylated phosphoprotein expressed on the surface of B cells. The CD3 arm binds to and recruits T cells, which are activated upon target engagement with CD20, resulting in robust T cell proliferation and cell killing.

The amino acid sequences comprising mosunetuzumab are summarized in the Table 1 above.

Recombinant mosunetuzumab was produced in two separate CHO cell lines using the knob-in-hole technology, including the glycosylation mutation N297G to reduce or eliminate ADCC function. Mosunetuzumab was composed of one anti-CD20 half antibody (an anti-CD20 arm) with a knob and one anti-CD3 half antibody (an anti-CD3 arm) with a hole, which half antibodies were assembled using a glutathione reduction. Mosunetuzumab was active against indolent (e.g., non-dividing) and chemo-resistant cells, and prior immune response to tumor was not a prerequisite for activity.

The dose range in subsequent and ongoing clinical trials varied due to the use of a step-fractionated dosing scheme in which, during cycle 1, patients received a low dose (e.g., 1 mg) on day 1, an intermediate dose (e.g., 2 mg) on day 8, and a full dose (e.g., 20 mg or 30 mg) on day 15. Several formulation options were considered when pairing protein concentration with low or high surfactant level (FIG. 1). In particular, a relatively low protein concentration and relatively high surfactant concentration were considered preferable to ensure accurate delivery of low doses using an intravenous fluid (IV) bag, to reduce or avoid the use of diluents, to permit flexibility of dosing, and to reduce or eliminate waste.

Example 2. Knowledge Building Study

A knowledge building study was executed after early-stage development to evaluate the impact of formulation parameters on stability of the formulations and to identify major risks of the formulations. Importantly, the results of this study suggested that oxidative degradation (e.g., oxidative degradation related to other forms of degradation, such as aggregation, fragmentation, and surfactant degradation) is a primary risk factor for clinical phase III DP formulation (i.e., a low-concentration mosunetuzumab DP formulation). In addition, the results of this study suggested that low-protein concentration mosunetuzumab formulations can be susceptible to oxidative degradation, particularly those formulations that have a high histidine concentration, low sucrose concentration, and a high PS20 concentration. Further, the results of this study suggested that the addition of methionine (L-methionine; L-Met) inhibited oxidative degradation, thereby reducing the risk of other forms of degradation (e.g., aggregation, fragmentation, and/or surfactant degradation).

Example 3. Formulation Development

The purpose of the studies in this Example was to characterize risks associated with pharmaceutical compositions having mosunetuzumab, and to identify formulation parameters that reduce these risks. The studies are summarized and characterize the effects of various components of the DS and DP formulations and the containers in which they can be stored. The studies also found that an important characteristic for such formulations was the molar ratio of mosunetuzumab to surfactant, where the protein was present at low molar concentrations and the surfactant at higher molar concentrations.

3.1. IV Bag Agitation Study

To determine the appropriate amount and composition of surfactant for use in formulations delivered using IV bags and without the use of a diluent which support a wide dose range, IV bag agitation studies were performed. Several factors were characterized, including protein concentration, dose, IV bag size, surfactant composition, and surfactant concentration.

Mosunetuzumab was formulated at various protein concentrations (1 mg/ml, 5 mg/ml, and 10 mg/ml) in 20 mM histidine acetate (HisOAc), 240 mM sucrose, pH 5.8. A range of doses (1 mg, 2 mg, 5 mg, 20 mg, and 30 mg) was tested, and 50-ml and 100-ml polyoxyethelene (PO) bags were assessed. 50-ml and 100-ml PO IV bags had been previously determined to be high-risk IV bags because of protein aggregation due to the relatively large headspace and high wall rigidity relative to polyvinyl chloride (PVC) IV bags of corresponding size. Three surfactants were evaluated: polysorbate 20 (PS20), poloxamer 188 (P188), and super-refined polysorbate 20 (srPS20). PS20 and P188 were tested over the full dose range, and limited testing was performed with srPS20, in view of its comparability to PS20 in agitation studies. SrPS20 was subsequently discontinued to simplify the studies.

In these experiments, DP surfactant concentration was varied to determine the minimum surfactant concentration in the IV bag required to prevent aggregation and particle formation during IV bag agitation stress. For each test condition, mosunetuzumab DP was injected into the IV bag and shaken at 100 rpm on an orbital shaker at 2-8° C. for up to 24 hours. Samples were taken at 0, 1, 6, and 24 hours and assessed for sub-visible particles by high accuracy liquid particle counting (HIAC), and soluble aggregates by size-exclusion high performance liquid chromatography (SE-HPLC). A condition was considered to pass if there was no substantial increase in soluble aggregate or particle counts. Increase in soluble aggregate was assessed by observed qualitative changes in the SE-HPLC chromatogram compared to time 0. Particle formation was observed as a significant increase in sub-visible particle counts compared to time 0 (an increase of >1000 in cumulative particle counts/ml at 2 μm).

Data from this study were analyzed to determine the minimum amount of surfactant in the IV bag required to support phase III and commercial dose administration without a diluent. FIG. 2 shows how DP protein concentration and dose together affected the minimum required PS20 concentration in a 100-ml PO IV bag. Similar results were observed for 50-ml PO IV bags. A relatively high ratio of PS20 concentration to protein concentration (e.g., for low doses, such as 1 mg/ml) ensured that there was a sufficient surfactant level in the final dose solution in IV bags. These results suggest that a high ratio of PS20 to protein concentrations may be better for ensuring protein stability, e.g., in IV bags, at low DP doses (e.g., 1 mg/ml).

Minimum suitable surfactant levels were determined for each surfactant composition for 1 mg/ml DP, which was identified as an effective protein concentration to support low dose administration, as shown in FIG. 3. It was determined that a minimum of 0.05% (w/v) PS20 (molar ratio of surfactant to mosunetuzumab of about 59) and super refined PS20 (srPS20), and a minimum of 0.08% (w/v) P188 (molar ratio of surfactant to mosunetuzumab of about 14), were necessary to prevent aggregation and particle formation during the shaking stress conditions described above. To support a manufacturing range, the PS20 target level was set at 0.06% (w/v) (molar ratio of surfactant to mosunetuzumab of about 71) and P188 target level was set at 0.10% (w/v) (molar ratio of surfactant to mosunetuzumab of about 17) for the following DP formulation development.

3.2. Product Quality Impact of Surfactant

Product quality impact (P01) of different surfactant types was evaluated in a stability study. Oxidation risk for mosunetuzumab was of particular interest due to the observed oxidation effects in the knowledge building study (Example 2). Additionally, PS20 is known to be susceptible to oxidation, and high levels of PS20 (e.g., 0.06%, selected by the IV bag agitation study) may increase the risk of protein oxidation. In this study, protein concentration (60 mg/ml, 10 mg/ml, and 1 mg/ml) and surfactant composition (PS20, srPS20, and P188) were evaluated in a full-factorial study. All materials were formulated at the respective protein concentration with 20 mM histidine acetate (HisOAc), 240 mM sucrose, and 0.1% (w/v) surfactant, at pH 5.8. For PS20 or srPS20 as the surfactant, with protein concentrations of 60 mg/ml, 10 mg/ml, and 1 mg/ml, the molar ratios of surfactant to mosunetuzumab were about 2, 12, and 119, respectively. For P188 as the surfactant, with protein concentrations of 60 mg/ml, 10 mg/ml, and 1 mg/ml, the molar ratios of surfactant to mosunetuzumab were about 0.3, 1.7, and 17, respectively. The samples were hand filled into 6-ml glass vials at a fill volume of 3 ml, stoppered and capped using standard components, and stored for up to one month at 40° C. and up to three months at 30° C. Assays included peptide mapping to quantify oxidation, HIAC to quantify aggregation and particle formation, evaporative light scattering detector (ELSD) to quantify surfactant degradation, and SE-HPLC to quantify size heterogeneity.

Figure 4A:
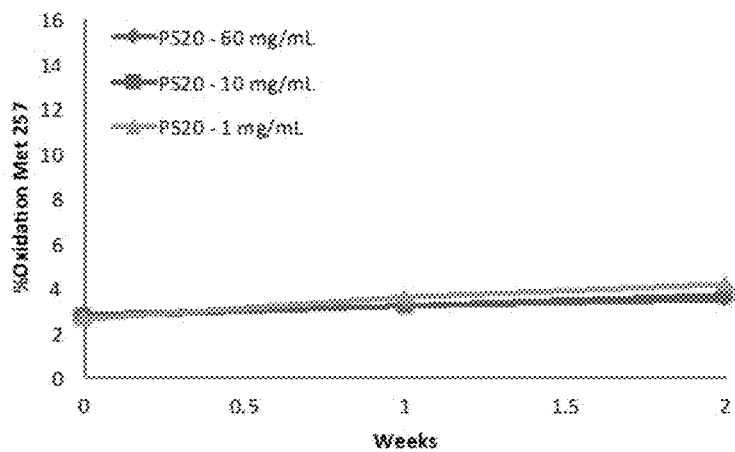
FIG. 4A is a graph showing kinetics of protein oxidation at methionine 257 (Met257) of mosunetuzumab (BTCT4465A) formulated with PS20 at 1 mg/ml (triangles), 10 mg/ml (squares), or 60 mg/ml (diamonds) at 40° C.
Figure 4B:
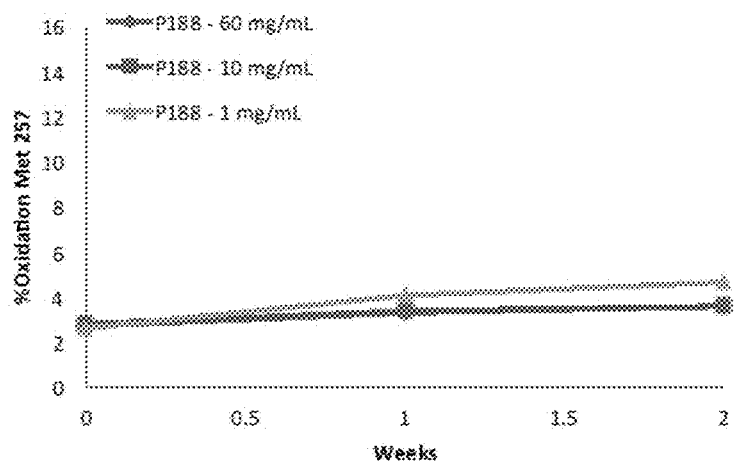
FIG. 4B is a graph showing kinetics of protein oxidation at methionine 257 of mosunetuzumab formulated with P188 at 1 mg/ml (triangles), 10 mg/ml (squares), or 60 mg/ml (diamonds) at 40° C.
Figure 4C:
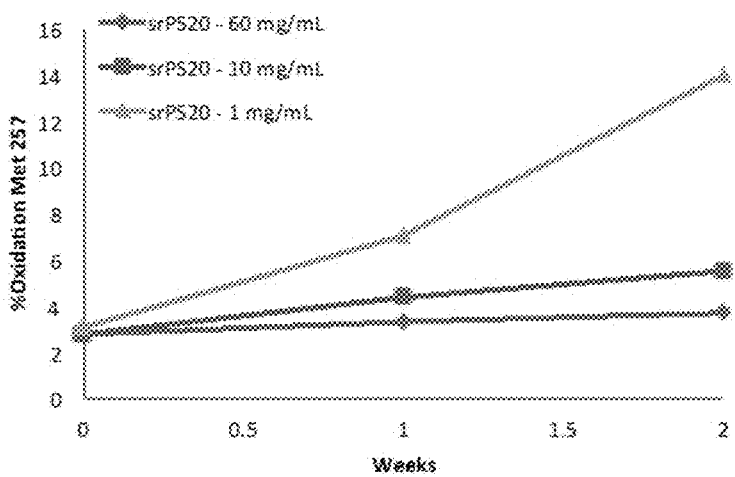
FIG. 4C is a graph showing kinetics of protein oxidation at methionine 257 of mosunetuzumab formulated with srPS20 at 1 mg/ml (triangles), 10 mg/ml (squares), or 60 mg/ml (diamonds) at 40° C.

In compositions including PS20 or P188, Met 257 (M257) oxidation increased only slightly as protein concentration decreased from 60 mg/ml to 1 mg/ml (FIG. 4A and FIG. 4B). However, for srPS20, oxidation increased significantly at 1 mg/ml protein concentration (FIG. 4C). In the 1 mg/ml srPS20 sample, increases in fragmentation and aggregation and loss of surfactant were also observed. Based on these results, srPS20 was excluded as a surfactant choice for mosunetuzumab formulation.

3.3. Histidine Concentration, Ambient Light Exposure, and Antioxidant Screen

Histidine is susceptible to oxidation and its presence in the formulation buffer can induce protein oxidation. In this example, the impact of histidine concentration was further characterized. The knowledge building study described in Example 2 and surfactant type studies described above revealed that mosunetuzumab is sensitive to oxidation from thermal stress. However, the impact of light stress on mosunetuzumab had not been characterized. Here, the sensitivity of tryptophan residues of mosunetuzumab to oxidation was quantified.

Two formulations were evaluated for thermal stress and four formulations were evaluated for light stress (Table 3). All formulations included 1 mg/ml mosunetuzumab, 160 mM sucrose, 0.04% (w/v) PS20, pH of 5.5, in addition to the specified composition. In this example, the molar ratio of surfactant to mosunetuzumab is about 48. Formulation 7 (F7) was identified in the knowledge building study as being at risk for high oxidation by thermal stress. A low histidine F7 formulation (F7-low His) was included in this study to evaluate the impact of decreasing histidine concentration. In light stress studies, F7 was supplemented with the antioxidant methionine, alone or in combination with N-acetyl tryptophan (NAT), to evaluate the effect of antioxidant on light stress-mediated degradation. The formulations were filled into 6-ml vials with a fill volume of 3 ml, stoppered, capped, and placed under thermal stress (up to one month at 40° C. and up to three months at 25° C.) and ambient light stress (300,000 lux-hours at 25° C.). Ambient light exposure was performed by incubating samples in a fluorescent light box maintained at room temperature and 5500 lux light intensity for 54 hours. Assays included peptide mapping to quantify oxidation, HIAC to quantify aggregation and particle formation, ELSD to quantify surfactant degradation, and SE-HPLC to quantify size heterogeneity (e.g., as a result of fragmentation and/or aggregation).

TABLE 3

Formulation summary for oxidation study

| Formulation | His (mM) | Met (mM) | NAT (mM) | Thermal stress | Light Stress |
|---|---|---|---|---|---|
| F7 | 30 | 0 | 0 | X | X |
| F7 + Met | 30 | 5 | 0 | | X |
| F7 + Met + NAT | 30 | 5 | 5 | | X |
| F7-low His | 10 | 0 | 0 | X | X |

Figure 5:
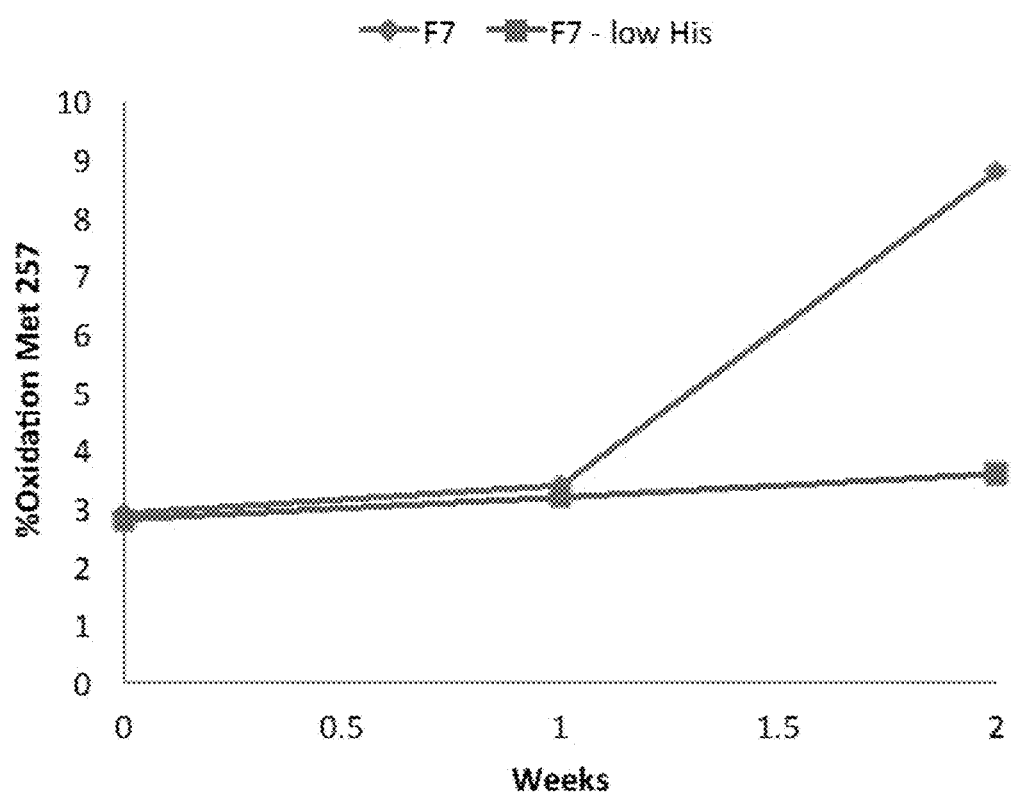
FIG. 5 is a graph showing kinetics of protein oxidation at methionine 257 of mosunetuzumab formulated with 30 mM histidine (diamonds) or 10 mM histidine (squares) at 40° C.

Compositions containing different levels of histidine (F7 and F7-low His) under 40° C. thermal stress conditions were compared. Both samples contained no antioxidant. As shown in FIG. 5, the 30 mM histidine composition exhibited approximately 6% M257 oxidation after two weeks at 40° C., whereas the 10 mM histidine composition exhibited less than 1% M257 oxidation. In addition, the aggregation level for both dimer and high molecular weight species (HMWS) was also higher in the 30 mM histidine sample. Results suggest that higher surfactant level and lower histidine acetate (HisOAc) concentration may be better for preventing oxidative stress under thermal stress conditions.

Figure 6:
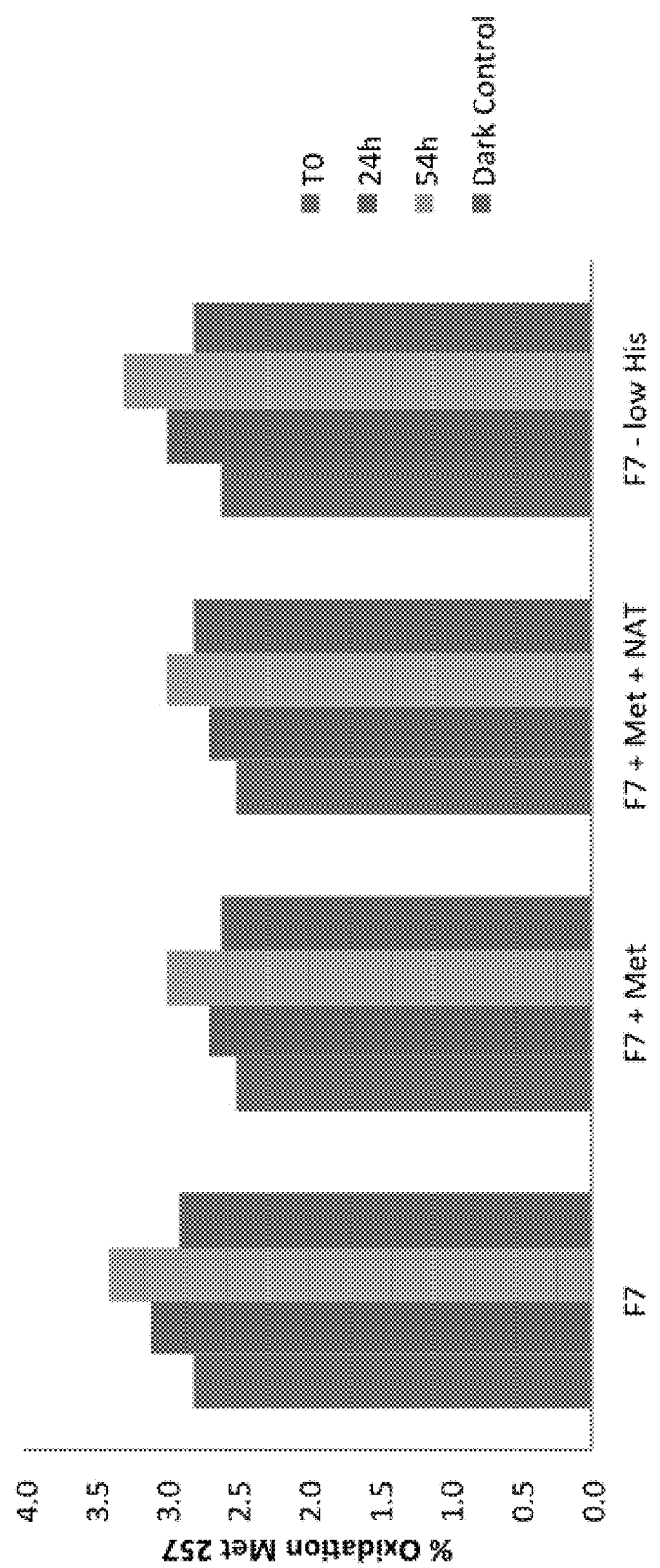
FIG. 6 is a graph showing percent oxidation at methionine 257 of mosunetuzumab in various formulations after up to 300,000 lux-hours of ambient light exposure (at 5,500 lux light intensity). The first bar for each formulation on the x-axis (left to right) represents time=0; the second bar, 24 hours; the third bar, 54 hours; and the last (fourth) bar, dark control.

Effects of histidine concentration and antioxidant were evaluated under ambient light exposure, a sensitive stress type that can induce oxidation. As shown in FIG. 6, no substantial change in oxidation at any site (Met or Trp) was observed in any sample tested, indicating that F7 is stable under the relevant ambient light stress, despite being at high-risk for oxidation. NAT provided no additional benefit and was therefore not included in subsequent formulation development.

3.4. Methionine Concentration Optimization

Hydrogen peroxide spiking studies were performed to identify preferable concentrations of methionine, which was identified as an important excipient. Samples containing 1 mg/ml mosunetuzumab, 15 mM histidine acetate, 0.08% (w/v) PS20, 160 mM sucrose, at pH of 5.8 (control formulation) were prepared with or without hydrogen peroxide ($H_2O_2$) and different levels of Met (Table 4). In these samples the molar ratio of surfactant to mosunetuzumab is about 95. The control formulation has a high-risk for oxidation, as it contains a relatively high concentration of histidine, a relatively high concentration of PS20, and a relatively low concentration of sucrose.

Hydrogen peroxide (2,000 ng/ml) was used as an oxidative stress challenge to antioxidant protection. Samples were filled into 20 cc vials with a fill volume of 3 ml to represent container conditions at high risk for oxidation due to a large headspace. Vials were stoppered, capped, and placed on thermal stability for one month at 40° C. or six months at 25° C., or on real-time stability, i.e., at 2-8° C. In ambient light studies, samples were subject to ambient light exposure up to 300,000 lux-hours (54 hours at 5,500 lux) at room temperature. Samples were obtained from the ambient light study at time points of 0 hours, 24 hours, 48 hours, and 54 hours, and an aluminum foil-wrapped dark control was included. The AMPLEX® hydrogen peroxide/peroxidase assay (ThermoFisher Scientific; Waltham, MA) was used to measure hydrogen peroxide concentration. Assays used to monitor product quality (e.g., stability) included color, pH, turbidity (by ultraviolet spectrometry (UV-spec)), strength (by UV-spec), charge variants (by imaged capillary isoelectric focusing (icIEF) and microchip sieving electrophoresis (MCE-SDS)), size heterogeneity (by SE-HPLC), visible and sub-visible particles (by HIAC), potency, oxidation (by peptide mapping), methionine concentration (by mass spectrometry), and polysorbate concentration (by ELSD).

TABLE 4

Formulation summary for methionine study

| Sample[a] | Met (mM) | H$_2$O$_2$ (ng/ml) |
|---|---|---|
| Control | 0 | 0 |
| + H$_2$O$_2$ | 0 | 2000 |
| + H$_2$O$_2$ + Met 2.5 | 2.5 | 2000 |
| + Met 5 | 5 | 0 |
| + H$_2$O$_2$ + Met 5 | 5 | 2000 |
| + H$_2$O$_2$ + Met 10 | 10 | 2000 |

[a] All samples contained 1 mg/ml mosunetuzumab, 15 mM histidine acetate, 0.08% (w/v) PS20, 160 mM sucrose, and a pH of 5.8 in addition to the composition specified in the table.

Figure 7A:
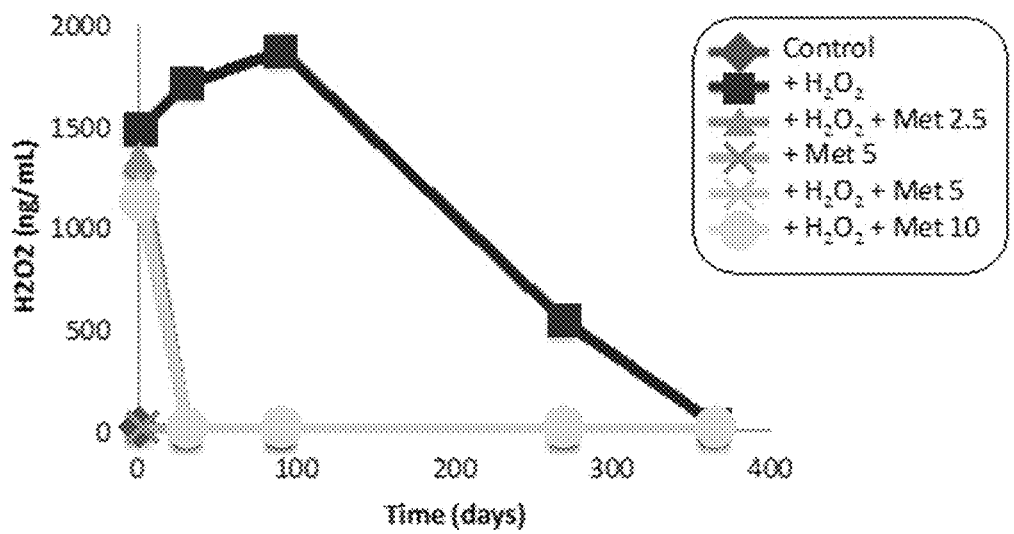
FIG. 7A is a graph showing kinetics of hydrogen peroxide ($H_2O_2$) concentration in various mosunetuzumab (BTCT4465A) compositions stored at 5° C. for up to 12 months. Mosunetuzumab compositions tested included composition alone (1 mg/ml mosunetuzumab, 15 mM histidine acetate, 0.08% (w/v) PS20, 160 mM sucrose, pH 5.8; control, diamonds), composition +$H_2O_2$ (squares), composition +$H_2O_2$+2.5 mM methionine (triangles), composition +5 mM methionine (dark X's), composition +$H_2O_2$+5 mM methionine (light X's), and composition +$H_2O_2$+10 mM methionine (light X's). $H_2O_2$ concentrations were measured by AMPLEX® Red assay.
Figure 7B:
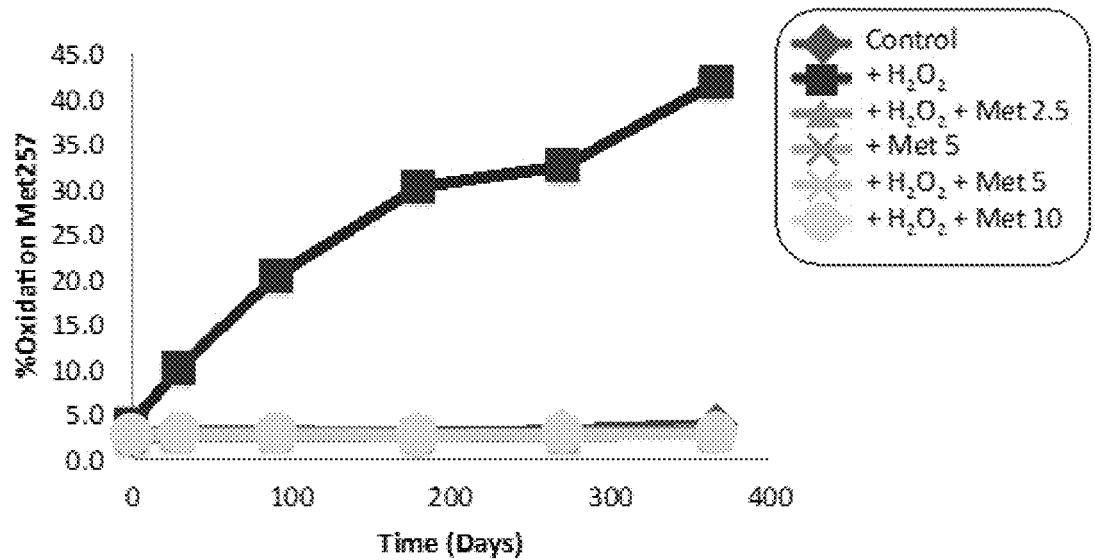
FIG. 7B is a graph showing kinetics of oxidation at methionine 257 in various mosunetuzumab compositions stored at 5° C. for up to 12 months. Mosunetuzumab compositions tested included composition alone (1 mg/ml mosunetuzumab, 15 mM histidine acetate, 0.08% (w/v) PS20, 160 mM sucrose, pH 5.8; control, diamonds), composition +$H_2O_2$ (squares), composition +$H_2O_2$+2.5 mM methionine (triangles), composition +5 mM methionine (dark X's), composition +$H_2O_2$+5 mM methionine (light X's), and composition +$H_2O_2$+10 mM methionine (light X's). Oxidation was measured by peptide mapping.

After storage for 12 months at 2-8° C. (e.g., 5° C.), the H$_2$O$_2$ present in formulations containing no Met was completely depleted (FIG. 7A). At 12 months, 41.5% M257 oxidation was observed, as opposed to 3.7% M257 oxidation in the control sample (FIG. 7B). With a minimum of 2.5 mM Met added to the formulation, the H$_2$O$_2$ was consumed completely after one month (FIG. 7A), and M257 oxidation remained equivalent with the control sample throughout the duration of the study (FIG. 7B). No differences were observed between formulations containing 2.5 mM, 5 mM, and 10 mM Met. No changes in other attributes were observed.

Figure 8A:
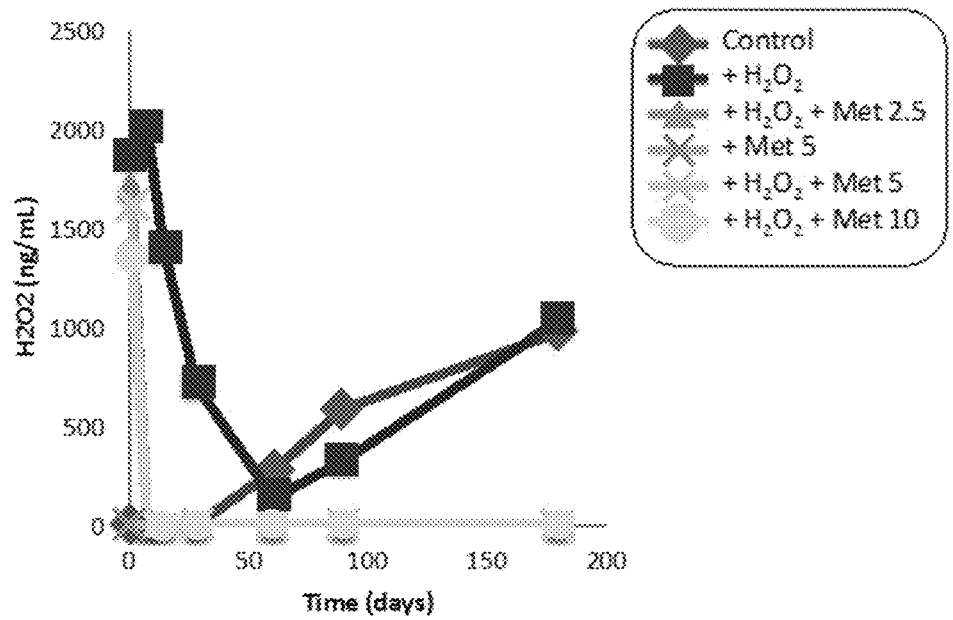
FIG. 8A is a graph showing kinetics of hydrogen peroxide ($H_2O_2$) concentration in various mosunetuzumab compositions stored at 25° C. for up to six months. Mosunetuzumab compositions tested included composition alone (1 mg/ml mosunetuzumab, 15 mM histidine acetate, 0.08% (w/v) PS20, 160 mM sucrose, pH 5.8; control, diamonds), composition +$H_2O_2$ (squares), composition +$H_2O_2$+2.5 mM methionine (triangles), composition +5 mM methionine (dark X's), composition +$H_2O_2$+5 mM methionine (light X's), and composition +$H_2O_2$+10 mM methionine (light X's). $H_2O_2$ concentrations were measured by AMPLEX® Red assay.
Figure 8B:
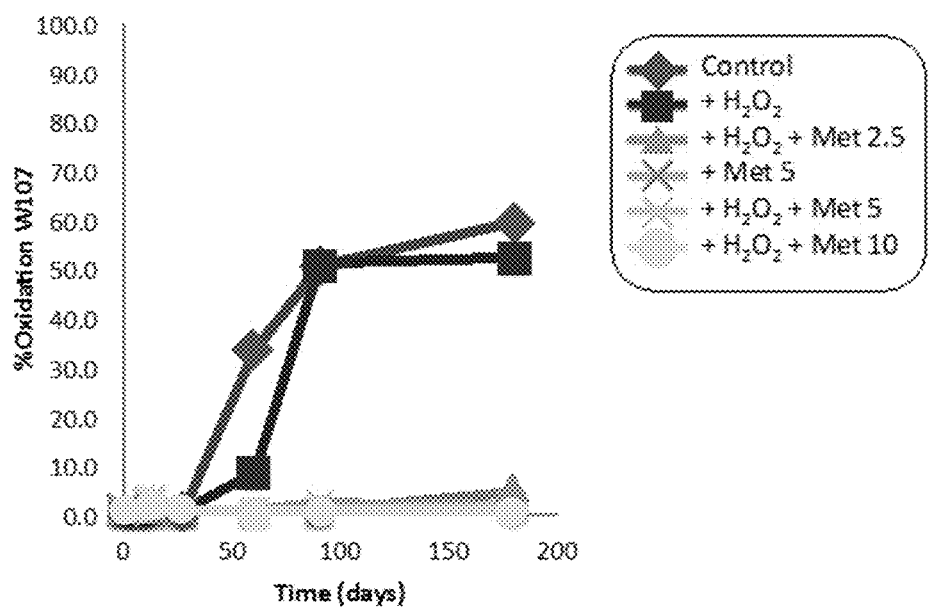
FIG. 8B is a graph showing kinetics of oxidation at tryptophan 107 in the CD20 arm of various mosunetuzumab compositions stored at 25° C. for up to six months. Mosunetuzumab compositions tested included composition alone (1 mg/ml mosunetuzumab, 15 mM histidine acetate, 0.08% (w/v) PS20, 160 mM sucrose, pH 5.8; control, diamonds), composition +$H_2O_2$ (squares), composition +$H_2O_2$+2.5 mM methionine (triangles), composition +5 mM methionine (dark X's), composition +$H_2O_2$+5 mM methionine (light X's), and composition +$H_2O_2$+10 mM methionine (light X's). Oxidation was measured by peptide mapping.
Figure 8C:
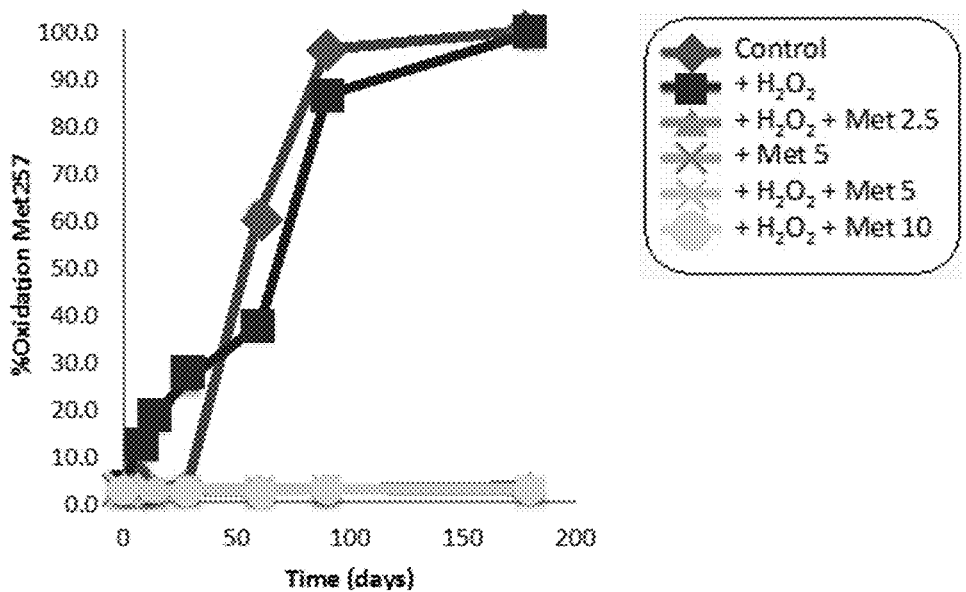
FIG. 8C is a graph showing kinetics of oxidation at methionine 257 of various mosunetuzumab compositions stored at 25° C. for up to six months. Mosunetuzumab compositions tested included composition alone (1 mg/ml mosunetuzumab, 15 mM histidine acetate, 0.08% (w/v) PS20, 160 mM sucrose, pH 5.8; control, diamonds), composition +$H_2O_2$ (squares), composition +$H_2O_2$+2.5 mM methionine (triangles), composition +5 mM methionine (dark X's), composition +$H_2O_2$+5 mM methionine (light X's), and composition +$H_2O_2$+10 mM methionine (light X's). Oxidation was measured by peptide mapping.
Figure 8D:
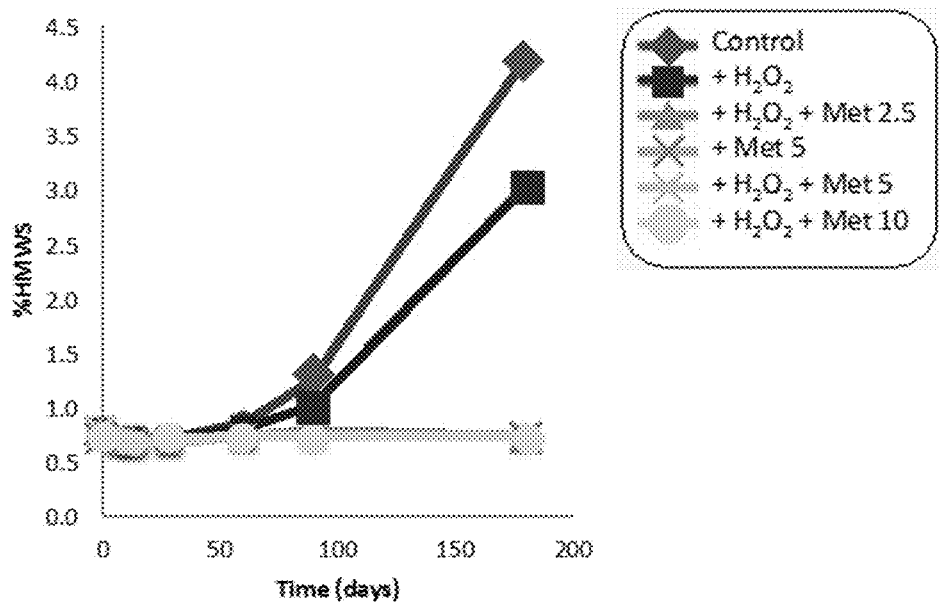
FIG. 8D is a graph showing kinetics of high molecular weight species (HMWS) levels, measured by SEC, in various mosunetuzumab compositions stored at 25° C. for up to six months. Mosunetuzumab compositions tested included composition alone (1 mg/ml mosunetuzumab, 15 mM histidine acetate, 0.08% (w/v) PS20, 160 mM sucrose, pH 5.8; control, diamonds), composition +$H_2O_2$ (squares), composition +$H_2O_2$+2.5 mM methionine (triangles), composition +5 mM methionine (dark X's), composition +$H_2O_2$+5 mM methionine (light X's), and composition +$H_2O_2$+10 mM methionine (light X's).
Figure 8E:
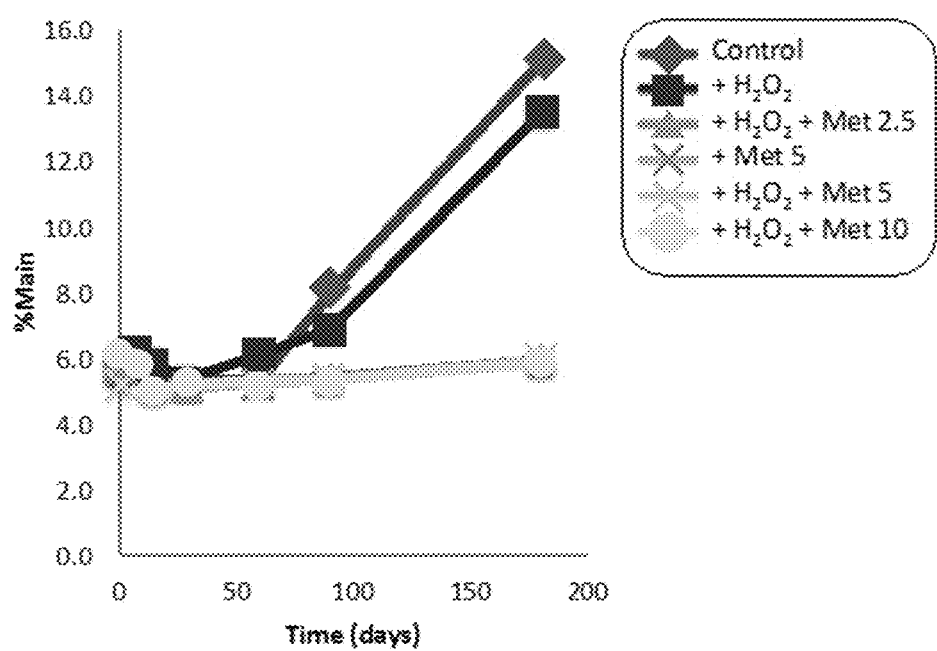
FIG. 8E is a graph showing kinetics of levels of low molecular weight species, measured by mCE-SDS, in various mosunetuzumab compositions stored at 25° C. for up to six months. Mosunetuzumab compositions tested included composition alone (1 mg/ml mosunetuzumab, 15 mM histidine acetate, 0.08% (w/v) PS20, 160 mM sucrose, pH 5.8; control, diamonds), composition $+H_2O_2$ (squares), composition $+H_2O_2+2.5$ mM methionine (triangles), composition $+5$ mM methionine (dark X's), composition $+H_2O_2+5$ mM methionine (light X's), and composition $+H_2O_2+10$ mM methionine (light X's).

At accelerated thermal conditions (i.e., 25° C.), the level of H$_2$O$_2$ in samples containing no Met decreased to 130 ng/ml at two months and subsequently accumulated back to a level of 1,000 ng/ml by six months (FIG. 8A). The control sample also exhibited an increase of H$_2$O$_2$ after two months (FIG. 8A). This observation is consistent with a slow phase of Met oxidation increase represented by M257 in the first two months for the spiked sample containing no Met and a fast phase of Met oxidation (FIG. 8C) in the later part up to 6 months for both the spiked sample with no Met and the control. This observation is also consistent with the increase in tryptophan 107 (i.e., Trp107 or W107) oxidation in the CD20 arm (FIG. 8B), protein aggregation (FIG. 8D), and fragmentation (FIG. 8E) between two and six months for both the spiked sample containing no Met and control sample. This observed H$_2$O$_2$ production is likely related to oxidative PS20 degradation in both the control and spiked sample with no Met, which can trigger further protein degradation. In contrast, upon addition of 2.5-10 mM Met, H$_2$O$_2$ was consumed completely after one week and did not re-accumulate over the course of the six-month incubation (FIG. 8A). Increases in M257 oxidation, W107 oxidation, aggregation, fragmentation, and PS20 degradation were greatly reduced by 2.5 mM Met and completely inhibited by 5 mM and 10 mM Met through the six-month incubation (FIG. 8B-FIG. 8E), suggesting that 5 mM Met was the minimal requirement as antioxidant for this formulation under these conditions. A similar trend was observed from stress stability results at 40° C. on a shorter time scale.

The samples in Table 5 were all also subjected to ambient light stress (up to 300,000 lux-hours) at 25° C. Consistent with the histidine concentration study, ambient light did not cause extensive oxidation, and the minor M257 oxidation generated in the sample without Met was completely inhibited by 2.5 mM Met addition.

TABLE 5

DP formulation summary

| Formulation[a] | His acetate (mM) | pH | PS20 (% w/v) | Sucrose (mM) | Met (mM) |
|---|---|---|---|---|---|
| 1 (Target) | 10 | 5.8 | 0.06 | 240 | 5 |
| 2 | 15 | 5.5 | 0.08 | 160 | 2.5 |
| 3 | 15 | 5.8 | 0.08 | 160 | 2.5 |
| 4 | 15 | 6.1 | 0.08 | 160 | 2.5 |
| 5 | 15 | 5.8 | 0.08 | 160 | 5 |

[a] All formulations contained 1 mg/ml mosunetuzumab.

3.5 DP Formulation Screen

A DP formulation screening study was performed based on information obtained from the studies described above. The target formulation and high-risk oxidation (high His, high PS20, low sucrose) were evaluated with varied pH and Met concentrations. Each formulation was sterile-filtered and filled into 15-ml glass vials with a 5-ml fill volume. Vials were stoppered with 20-mm Daikyo D777-1 liquid stoppers (Daikyo; Tochigi, Japan), capped with aluminum flip-top caps, and stored upright on stability according to the program specified in Table 6. Assays were configured to observe color, pH, turbidity (by UV-spec), strength (by UV-spec), charge variants (by icIEF and mCE-SDS), size heterogeneity (by SE-HPLC), visible and sub-visible particles (by HIAC), potency, oxidation (by peptide mapping), methionine concentration (by mass spectrometry), and polysorbate concentration (by ELSD).

TABLE 6

DP formulation sample time points

| Storage temperature/ Time Point | T$_0$ | 3 D | 1 W | 2 W | 3 W | 1 M | 2 M | 3 M | 6 M | 9 M | 12 M | 18 M | 24 M |
|---|---|---|---|---|---|---|---|---|---|---|---|---|---|
| 5° C. | X* | | | | | | X | X | X | X | X | X | X |
| 25° C., 65% RH | | | | X | | X | X | X | X | | | | |
| 40° C., 75% RH | | X | X | X | X | X | | | | | | | |

X = 3 vials;
X* = 5 vials;
D = days,
W = weeks,
M = months

Time zero ($T_0$) characterization of the formulations is summarized in Table 7. No change was observed for any formulation after 12 months at 5° C. (Table 8). After storage at 5° C. for 24 months, consistent changes through all five formulation were observed by iCIEF and CE-SDS. There is a small increase in percent acidic variants by icIEF, and the CE-SDS results for pre-peaks appear to show a slight increase after 24 months at 5° C., but were observed to increase the same across all formulations. No changes were observed by any other assay.

After storage at 25° C., 60% relative humidity (RH; accelerated condition) for six months (Table 9), similar changes were observed across all five formulations for SE-HPLC main peak decrease (0.3-0.4%), icIEF acidic increase and main peak decrease (12.6-17%), and mCE-SDS main peak decrease and pre-peaks increase (1.0%). No changes were observed by any other assay conducted.

Figure 9A:
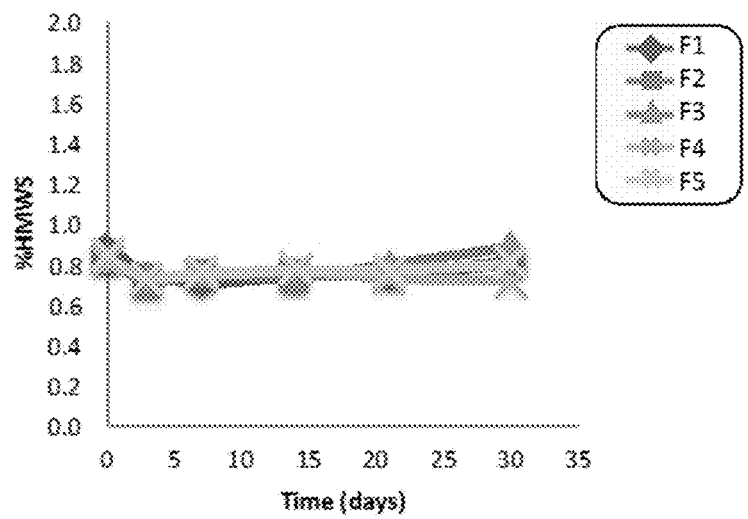
FIG. 9A is a graph showing change in HMWS levels over time, measured by SE-HPLC, in various mosunetuzumab formulations stored at 40° C. and 75% relative humidity (RH) for up to one month. Formulations F1-F5 are characterized in Table 6.
Figure 9B:
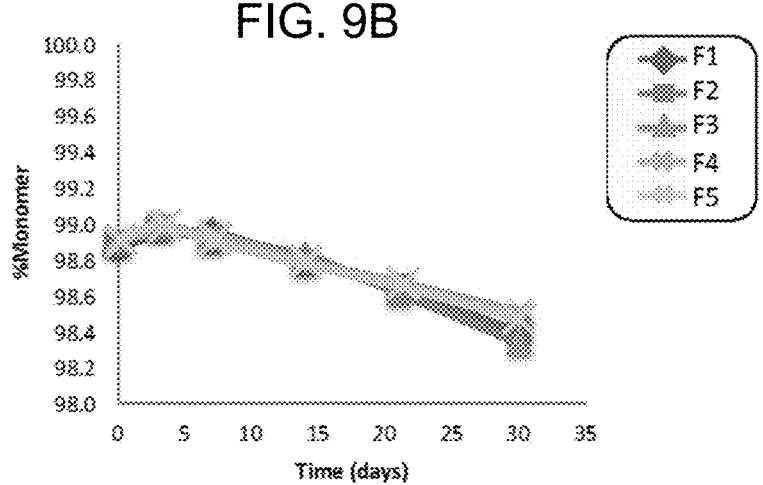
FIG. 9B is a graph showing change in monomer levels over time, measured by SE-HPLC, in various mosunetuzumab formulations stored at 40° C. and 75% RH for up to one month. Formulations F1-F5 are characterized in Table 6.
Figure 9C:
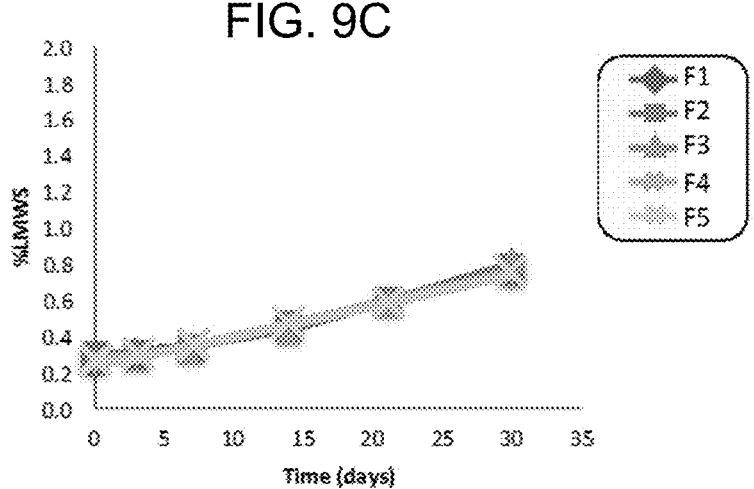
FIG. 9C is a graph showing change in LMWS levels over time, measured by SE-HPLC, in various mosunetuzumab formulations stored at 40° C. and 75% RH for up to one month. Formulations F1-F5 are characterized in Table 6.
Figure 10A:
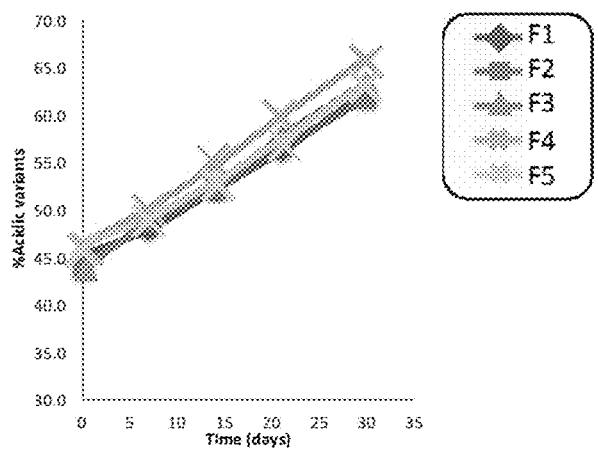
FIG. 10A is a graph showing change in acidic variants over time, measured by icIEF, in various mosunetuzumab formulations stored at 40° C. and 75% RH for up to one month. Formulations F1-F5 are characterized in Table 6.
Figure 10B:
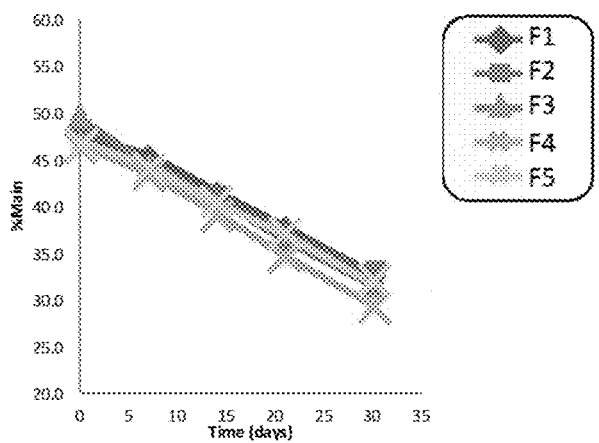
FIG. 10B is a graph showing change in main peak over time, measured by icIEF, in various mosunetuzumab formulations stored at 40° C. and 75% RH for up to one month. Formulations F1-F5 are characterized in Table 6.
Figure 10C:
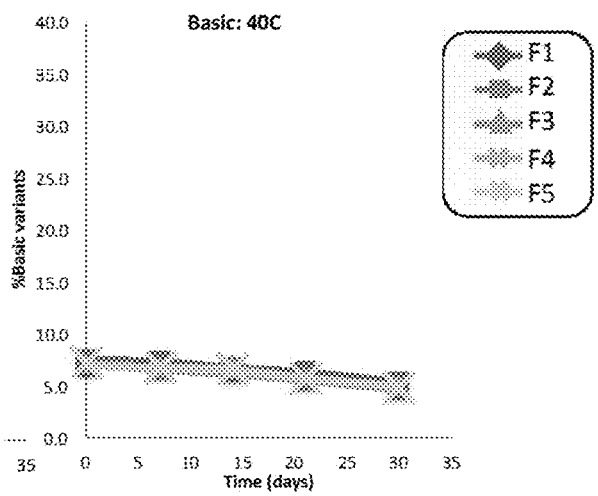
FIG. 10C is a graph showing change in basic variants over time, measured by icIEF, in various mosunetuzumab formulations stored at 40° C. and 75% RH for up to one month. Formulations F1-F5 are characterized in Table 6.
Figure 11A:
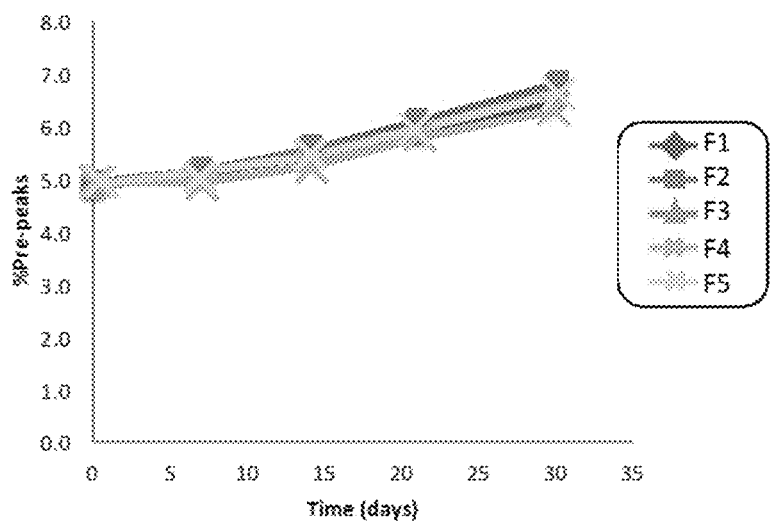
FIG. 11A is a graph showing change of sum of pre-peaks over time, measured by mCE-SDS, in various mosunetuzumab formulations stored at 40° C. and 75% RH for up to one month. Formulations F1-F5 are characterized in Table 6.
Figure 11B:
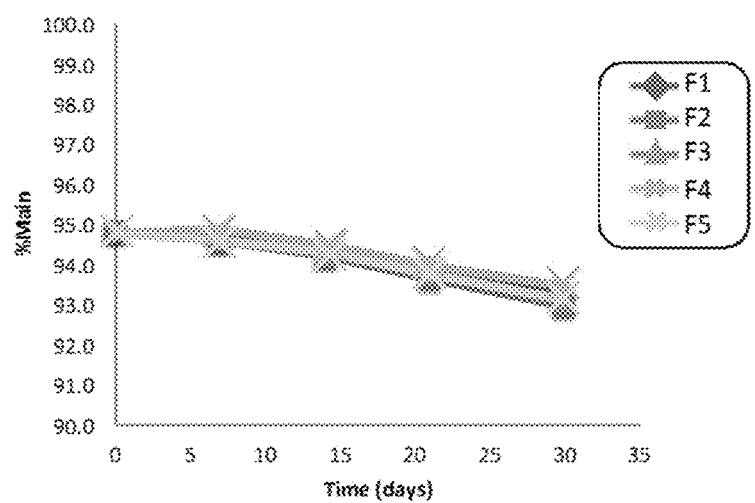
FIG. 11B is a graph showing change of sum of main peaks over time, measured by mCE-SDS, in various mosunetuzumab formulations stored at 40° C. and 75% RH for up to one month. Formulations F1-F5 are characterized in Table 6.

After storage at 40° C., 75% RH (stress condition) for one month (Table 10), similar changes were observed across all five formulations for SE-HPLC main peak decrease (0.4-0.6%, FIG. 9A-FIG. 9C), icIEF acidic increase and main peak decrease (17.1-19.8%, FIG. 10A-FIG. 10C), and mCE-SDS main peak decrease and pre-peak increase (1.4-1.9%, FIG. 11A and FIG. 11B). No change was observed for other assay conducted.

Results of this study indicated that mosunetuzumab DP was stable within pH 5.5-6.1, even at the high-risk condition for oxidation (high L-histidine, low sucrose, low L-methionine, high polysorbate).

TABLE 7

Formulation screen-$T_0$

| Formulation | Time (months) | CAC (Color/ Appearance) | Turbidity | Osmolality (mOsm/kg) | pH | Strength (mg/ml) | icIEF (% Acidic) | icIEF (% Main Peak) | icIEF (% Basic) | SE-HPLC (% HMWS) | SE-HPLC (% Main Peak) | SE-HPLC (% LMWS) |
|---|---|---|---|---|---|---|---|---|---|---|---|---|
| 1 (Target) | T = 0 | ≤BY7 | 0.03 | 286 | 5.8 | 1.01 | 45.3 | 47.5 | 7.2 | 0.9 | 98.9 | 0.3 |
| 2 | T = 0 | ≤BY7 | 0.02 | 203 | 5.5 | 1.02 | 44.3 | 48.2 | 7.5 | 0.8 | 98.9 | 0.3 |
| 3 | T = 0 | ≤BY7 | 0.02 | 201 | 5.8 | 0.99 | 43.7 | 49.2 | 7.1 | 0.8 | 98.9 | 0.3 |
| 4 | T = 0 | ≤BY7 | 0.03 | 195 | 6.2 | 0.98 | 46.4 | 46.5 | 7.1 | 0.8 | 98.9 | 0.3 |
| 5 | T = 0 | ≤BY7 | 0.01 | 203 | 5.8 | 1.02 | 46.2 | 46.9 | 6.9 | 0.8 | 98.9 | 0.3 |

| Formulation | Time (months) | Non-Reduced CE-SDS Sum of Pre-Peaks (%) | Non-Reduced CE-SDS (% Main Peak) | Visible Particulates | Subvisible Particulates (Cumulative Counts/ml) ≥2 μm | ≥5 μm | ≥10 μm | ≥25 μm | Potency | Oxidation L-Met (mM) | Oxidation Met 257 (%) | PS20 (% w/v) |
|---|---|---|---|---|---|---|---|---|---|---|---|---|
| 1 (Target) | T = 0 | 4.9 | 94.8 | PFVP | 16 | 7 | 1 | 0 | 103 | 4.6 | 2.8 | 0.06 |
| 2 | T = 0 | 4.9 | 94.8 | PFVP | 73 | 26 | 13 | 4 | 106 | 2.3 | 2.6 | 0.08 |
| 3 | T = 0 | 4.9 | 94.8 | PFVP | 8 | 3 | 0 | 0 | 113 | 2.3 | 2.6 | 0.08 |
| 4 | T = 0 | 4.9 | 94.8 | PFVP | 28 | 3 | 1 | 0 | 102 | 2.4 | 2.5 | 0.08 |
| 5 | T = 0 | 4.9 | 94.8 | PFVP | 137 | 25 | 7 | 1 | 109 | 4.8 | 2.7 | 0.08 |

TABLE 8

DP formulation screen results at 2-8° C.

| Formulation | Time (months) | Color | Turbidity | pH | Strength (mg/ml) | icIEF (% Acidic) | icIEF (% Main Peak) | icIEF (% Basic) | SE-HPLC (% HMWS) | SE-HPLC (% Main Peak) | SE-HPLC (% LMWS) |
|---|---|---|---|---|---|---|---|---|---|---|---|
| 1 (Target) | 1 | NT | 0.01 | 5.8 | NT | 45.0 | 47.8 | 7.2 | 0.8 | 98.9 | 0.3 |
| | 2 | ≤BY7 | 0.02 | 5.8 | NT | 47.1 | 45.4 | 7.5 | 0.7 | 99.0 | 0.3 |
| | 3 | ≤BY7 | NT | 5.8 | NT | 45.2 | 47.9 | 6.9 | 0.8 | 98.9 | 0.4 |
| | 6 | ≤B9* | 0.01 | 5.8 | 1.02 | 44.6 | 47.0 | 8.4 | 0.7 | 99.0 | 0.3 |
| | 9 | NT | 0.00 | 5.9 | NT | NT | NT | NT | 0.7 | 99.0 | 0.3 |
| | 12 | ≤B9* | 0.01 | 5.8 | NT | 45.3 | 46.7 | 8.0 | 0.7 | 99.0 | 0.3 |
| 2 | 1 | NT | 0.00 | 5.5 | NT | 43.1 | 49.3 | 7.6 | 0.8 | 99.0 | 0.2 |
| | 2 | ≤BY7 | 0.02 | 5.5 | NT | 45.0 | 46.6 | 8.4 | 0.8 | 99.0 | 0.3 |
| | 3 | ≤BY7 | NT | 5.5 | NT | 45.2 | 47.5 | 7.3 | 0.6 | 99.1 | 0.3 |
| | 6 | ≤B9* | 0.01 | 5.5 | 1.01 | 45.7 | 46.2 | 8.1 | 0.7 | 99.0 | 0.3 |
| | 9 | NT | 0.01 | 5.5 | NT | NT | NT | NT | 0.7 | 99.0 | 0.3 |
| | 12 | ≤B9* | 0.01 | 5.5 | NT | 43.7 | 46.7 | 9.7 | 0.7 | 99.0 | 0.3 |
| 3 | 1 | NT | 0.01 | 5.8 | NT | 44.4 | 48.2 | 7.4 | 0.8 | 99.0 | 0.3 |
| | 2 | ≤BY7 | 0.01 | 5.8 | NT | 45.7 | 46.7 | 7.6 | 0.8 | 98.9 | 0.3 |
| | 3 | ≤BY7 | NT | 5.8 | NT | 45.9 | 47.5 | 6.6 | 0.8 | 99.0 | 0.3 |
| | 6 | ≤B9* | 0.01 | 5.8 | 1.04 | 45.4 | 47.3 | 7.3 | 0.7 | 99.0 | 0.3 |
| | 9 | NT | 0.01 | 5.8 | NT | NT | NT | NT | 0.7 | 99.0 | 0.3 |
| | 12 | ≤B9* | 0.01 | 5.8 | NT | 45.7 | 46.3 | 8.1 | 0.7 | 99.0 | 0.3 |
| 4 | 1 | NT | 0.01 | 6.2 | NT | 45.1 | 48.0 | 6.9 | 0.8 | 98.9 | 0.3 |
| | 2 | ≤BY7 | 0.02 | 6.2 | NT | 46.8 | 46.0 | 7.3 | 0.8 | 98.9 | 0.3 |
| | 3 | ≤BY7 | NT | 6.2 | NT | 46.7 | 46.4 | 6.9 | 0.7 | 99.0 | 0.3 |

TABLE 8-continued

DP formulation screen results at 2-8° C.

|   |   |   |   |   |   |   |   |   |   |   |   |
|---|---|---|---|---|---|---|---|---|---|---|---|
|   | 6 | ≤B9* | 0.01 | 6.2 | 1.04 | 45.7 | 46.8 | 7.5 | 0.7 | 99.0 | 0.3 |
|   | 9 | NT | 0.01 | 6.2 | NT | NT | NT | NT | 0.7 | 99.0 | 0.3 |
|   | 12 | ≤B9* | 0.01 | 6.2 | NT | 47.1 | 45.1 | 7.8 | 0.8 | 99.0 | 0.3 |
| 5 | 1 | NT | −0.01 | 5.7 | NT | 44.8 | 48.2 | 7.0 | 0.8 | 98.9 | 0.3 |
|   | 2 | ≤BY7 | 0.00 | 5.8 | NT | 46.0 | 46.3 | 7.7 | 0.8 | 99.0 | 0.2 |
|   | 3 | ≤BY7 | NT | 5.8 | NT | 45.5 | 47.4 | 7.0 | 0.8 | 98.9 | 0.4 |
|   | 6 | ≤B9* | 0.00 | 5.8 | 1.02 | 45.9 | 46.0 | 8.1 | 0.7 | 99.0 | 0.3 |
|   | 9 | NT | 0.01 | 5.8 | NT | NT | NT | NT | 0.7 | 99.0 | 0.3 |
|   | 12 | ≤B9* | 0.01 | 5.8 | NT | 46.5 | 45.3 | 8.2 | 0.7 | 99.0 | 0.3 |

| | | Non-Reduced CE-SDS | | | Subvisible Particulates (Cumulative Counts/ml) | | | | | | Oxidation Met | |
|---|---|---|---|---|---|---|---|---|---|---|---|---|
| Formulation | Time (months) | Sum of Pre-Peaks (%) | (% Main Peak) | Visible Particulates | ≥2 µm | ≥5 µm | ≥10 µm | ≥25 µm | Potency (%) | L-Met (mM) | 257 (%) | (% w/v) |
| 1 | 1 | 5.1 | 94.6 | PFVP | 356 | 73 | 9 | 2 | NT | 4.9 | 2.6 | 0.06 |
|   | 2 | 5.0 | 94.7 | PFVP | 301 | 79 | 8 | 2 | NT | 4.5 | 2.6 | 0.06 |
|   | 3 | 5.0 | 94.8 | PFVP | 493 | 38 | 7 | 1 | NT | 3.9 | 2.5 | 0.06 |
|   | 6 | 4.9 | 94.8 | PFVP | 333 | 33 | 3 | 0 | NT | 4.8 | 2.6 | 0.06 |
|   | 9 | NT | NT | PFVP | 479 | 62 | 8 | 2 | NT | NT | NT | 0.06 |
|   | 12 | 5.0 | 94.7 | PFVP | 447 | 58 | 4 | 0 | 102 | 5.2 | 2.2 | 0.06 |
| 2 | 1 | 5.1 | 94.6 | PFVP | 42 | 13 | 6 | 2 | NT | 2.4 | 2.8 | 0.08 |
|   | 2 | 4.9 | 94.9 | PFVP | 351 | 68 | 9 | 2 | NT | 2.3 | 2.6 | 0.08 |
|   | 3 | 5.0 | 94.7 | PFVP | 738 | 163 | 23 | 0 | NT | 1.9 | 2.5 | 0.08 |
|   | 6 | 4.8 | 94.8 | PFVP | 271 | 73 | 6 | 0 | NT | 2.4 | 2.6 | 0.08 |
|   | 9 | NT | NT | PFVP | 34 | 9 | 3 | 1 | NT | NT | NT | 0.08 |
|   | 12 | 5.0 | 94.8 | PFVP | 787 | 107 | 2 | 0 | 107 | 2.6 | 2.3 | 0.08 |
| 3 | 1 | 5.2 | 94.4 | PFVP | 202 | 19 | 2 | 0 | NT | 2.5 | 2.7 | 0.08 |
|   | 2 | 5.0 | 94.7 | PFVP | 435 | 127 | 23 | 4 | NT | 2.3 | 2.5 | 0.08 |
|   | 3 | 4.9 | 94.8 | PFVP | 593 | 72 | 3 | 1 | NT | 2.1 | 2.5 | 0.08 |
|   | 6 | 4.8 | 94.9 | PFVP | 427 | 52 | 0 | 0 | NT | 2.4 | 2.7 | 0.08 |
|   | 9 | NT | NT | PFVP | 15 | 4 | 1 | 0 | NT | NT | NT | 0.08 |
|   | 12 | 5.0 | 94.7 | PFVP | 25 | 4 | 1 | 0 | 100 | 2.6 | 2.3 | 0.08 |
| 4 | 1 | 5.1 | 94.5 | PFVP | 395 | 67 | 13 | 2 | NT | 2.6 | 2.6 | 0.08 |
|   | 2 | 5.0 | 94.8 | PFVP | 242 | 38 | 3 | 0 | NT | 2.3 | 2.8 | 0.08 |
|   | 3 | 4.9 | 94.8 | PFVP | 242 | 27 | 4 | 1 | NT | 2.2 | 2.5 | 0.08 |
|   | 6 | 4.8 | 94.8 | PFVP | 755 | 135 | 15 | 0 | NT | 2.4 | 2.6 | 0.08 |
|   | 9 | NT | NT | PFVP | 143 | 12 | 2 | 0 | NT | NT | NT | 0.08 |
|   | 12 | 5.1 | 94.4 | PFVP | 733 | 60 | 3 | 0 | 93 | 2.6 | 2.3 | 0.08 |
| 5 | 1 | 5.2 | 94.4 | PFVP | 377 | 88 | 12 | 0 | NT | 4.8 | 2.6 | 0.08 |
|   | 2 | 5.0 | 94.8 | PFVP | 370 | 112 | 25 | 1 | NT | 4.5 | 2.6 | 0.08 |
|   | 3 | 4.9 | 94.8 | PFVP | 199 | 58 | 11 | 1 | NT | 4.0 | 2.5 | 0.08 |
|   | 6 | 4.8 | 94.9 | PFVP | 351 | 48 | 5 | 0 | NT | 4.9 | 2.7 | 0.08 |
|   | 9 | NT | NT | PFVP | 1047 | 148 | 2 | 0 | NT | NT | NT | 0.08 |
|   | 12 | 4.9 | 94.8 | PFVP | 229 | 20 | 0 | 0 | 2.2 | 0.08 | 4.9 | 94.8 |

TABLE 9

DP formulation screen results at 25° C./60% RH

| | | | | | | icIEF | | | SE-HPLC | | |
|---|---|---|---|---|---|---|---|---|---|---|---|
| Formulation | Time (months) | Color | Turbidity | pH | Strength (mg/ml) | (% Acidic) | (% Main Peak) | (% Basic) | (% HMWS) | (% Main Peak) | (% LMWS) |
| 1 | 0.5 | NT | NT | 5.8 | NT | 45.7 | 47.4 | 6.9 | 0.8 | 99.0 | 0.3 |
|   | 1 | NT | 0.02 | 5.8 | NT | 46.3 | 47.1 | 6.6 | 0.7 | 99.0 | 0.3 |
|   | 2 | NT | −0.01 | 5.8 | NT | 50.1 | 42.1 | 7.8 | 0.7 | 98.9 | 0.4 |
|   | 3 | NT | 0.01 | 5.8 | NT | 51.9 | 41.6 | 6.5 | 0.7 | 98.9 | 0.5 |
|   | 6 | ≤B9* | 0.00 | 5.8 | 1.04 | 57.9 | 35.3 | 6.8 | 0.7 | 98.6 | 0.7 |
| 2 | 0.5 | NT | NT | 5.5 | NT | 44.7 | 47.9 | 7.4 | 0.7 | 99.0 | 0.3 |
|   | 1 | NT | 0.03 | 5.5 | NT | 45.8 | 47.5 | 6.8 | 0.7 | 98.9 | 0.4 |
|   | 2 | NT | 0.02 | 5.5 | NT | 50.3 | 41.9 | 7.7 | 0.8 | 98.9 | 0.4 |
|   | 3 | NT | 0.00 | 5.5 | NT | 51.6 | 41.9 | 6.6 | 0.7 | 98.8 | 0.5 |
|   | 6 | ≤B9* | 0.01 | 5.5 | 1.04 | 57.3 | 35.1 | 7.6 | 0.8 | 98.5 | 0.7 |
| 3 | 0.5 | NT | NT | 5.8 | NT | 45.2 | 47.9 | 6 | 0.7 | 99.0 | 0.3 |
|   | 1 | NT | 0.07 | 5.7 | NT | 46.6 | 47.0 | 6.5 | 0.7 | 99.0 | 0.3 |
|   | 2 | NT | 0.00 | 5.8 | NT | 50.3 | 42.2 | 7.5 | 0.8 | 98.9 | 0.4 |
|   | 3 | NT | 0.00 | 5.8 | NT | 53.4 | 39.9 | 6.7 | 0.6 | 98.9 | 0.5 |
|   | 6 | ≤B9* | 0.00 | 5.8 | 1.04 | 60.3 | 33.3 | 6.4 | 0.8 | 98.5 | 0.7 |
| 4 | 0.5 | NT | NT | 6.2 | NT | 46.8 | 46.6 | 6.6 | 0.7 | 99.0 | 0.3 |
|   | 1 | NT | 0.05 | 6.2 | NT | 47.3 | 46.3 | 6.4 | 0.7 | 98.9 | 0.3 |
|   | 2 | NT | 0.01 | 6.2 | NT | 52.5 | 40.3 | 7.2 | 0.7 | 98.9 | 0.4 |

TABLE 9-continued

DP formulation screen results at 25° C./60% RH

| Formulation | Time (months) | Color | Turbidity | pH | Turbidity | (% Acidic) | (% Main Peak) | (% Basic) | (% HMWS) | (% Main Peak) | (% LMWS) |
|---|---|---|---|---|---|---|---|---|---|---|---|
|  | 3 | NT | 0.01 | 6.2 | NT | 56.0 | 38.0 | 6.0 | 0.7 | 98.8 | 0.5 |
|  | 6 | ≤B9* | 0.00 | 6.2 | 1.04 | 63.4 | 30.4 | 6.2 | 0.8 | 98.5 | 0.7 |
| 5 | 0.5 | NT | NT | 5.8 | NT | 45.1 | 47.8 | 7.2 | 0.8 | 99.0 | 0.3 |
|  | 1 | NT | 0.04 | 5.8 | NT | 47.6 | 45.7 | 6.8 | 0.7 | 98.9 | 0.3 |
|  | 2 | NT | −0.01 | 5.8 | NT | 50.2 | 42.6 | 7.2 | 0.8 | 98.9 | 0.4 |
|  | 3 | NT | 0.01 | 5.8 | NT | 52.7 | 41.8 | 5.6 | 0.7 | 98.8 | 0.6 |
|  | 6 | ≤B9* | 0.01 | 5.8 | 1.04 | 59.1 | 35.0 | 5.9 | 0.8 | 98.5 | 0.7 |

| Formulation | Time (months) | Non-Reduced CE-SDS Sum of Pre-Peaks (%) | (% Main Peak) | Visible Particulates | Subvisible Particulates (Cumulative Counts/ml) ≥2 μm | ≥5 μm | ≥10 μm | ≥25 μm | Potency (%) | L-Met (mM) | Oxidation Met257 (%) | PS20 (% w/v) |
|---|---|---|---|---|---|---|---|---|---|---|---|---|
| 1 | 0.5 | 5.0 | 94.7 | PFVP | 133 | 30 | 5 | 0 | NT | 4.8 | 2.7 | 0.06 |
|  | 1 | 5.1 | 94.6 | PFVP | 286 | 48 | 8 | 0 | NT | 4.8 | 2.6 | 0.06 |
|  | 2 | 5.1 | 94.7 | PFVP | 675 | 150 | 26 | 0 | NT | 4.5 | 2.7 | 0.06 |
|  | 3 | 5.3 | 94.5 | PFVP | 230 | 43 | 7 | 0 | NT | 3.8 | 2.5 | 0.06 |
|  | 6 | 5.8 | 94.0 | PFVP | 39 | 6 | 2 | 0 | 88 | 4.6 | 2.7 | 0.06 |
| 2 | 0.5 | 5.0 | 94.7 | PFVP | 42 | 13 | 6 | 2 | NT | 2.4 | 2.8 | 0.08 |
|  | 1 | 5.2 | 94.5 | PFVP | 351 | 68 | 9 | 2 | NT | 2.4 | 2.8 | 0.08 |
|  | 2 | 5.3 | 94.5 | PFVP | 738 | 163 | 23 | 0 | NT | 2.3 | 2.6 | 0.08 |
|  | 3 | 5.4 | 94.3 | PFVP | 366 | 64 | 18 | 0 | NT | 2.0 | 2.6 | 0.08 |
|  | 6 | 5.8 | 94.0 | PFVP | 217 | 73 | 8 | 0 | 86 | 2.4 | 2.7 | 0.08 |
| 3 | 0.5 | 4.9 | 94.8 | PFVP | 268 | 89 | 22 | 0 | NT | 2.5 | 2.8 | 0.08 |
|  | 1 | 5.1 | 94.6 | PFVP | 45 | 14 | 3 | 0 | NT | 2.4 | 3.0 | 0.08 |
|  | 2 | 5.2 | 94.6 | PFVP | 395 | 101 | 23 | 2 | NT | 2.4 | 2.8 | 0.08 |
|  | 3 | 5.4 | 94.4 | PFVP | 355 | 80 | 8 | 0 | NT | 1.7 | 2.7 | 0.08 |
|  | 6 | 5.8 | 94.0 | PFVP | 409 | 78 | 11 | 0 | 93 | 2.4 | 2.9 | 0.08 |
| 4 | 0.5 | 5.0 | 94.8 | PFVP | 98 | 40 | 6 | 0 | NT | 2.5 | 2.9 | 0.08 |
|  | 1 | 5.0 | 94.7 | PFVP | 36 | 8 | 2 | 0 | NT | 2.5 | 2.7 | 0.08 |
|  | 2 | 5.1 | 94.7 | PFVP | 653 | 148 | 20 | 0 | NT | 2.3 | 2.6 | 0.08 |
|  | 3 | 5.3 | 94.5 | PFVP | 578 | 128 | 23 | 0 | NT | 1.9 | 2.6 | 0.08 |
|  | 6 | 5.8 | 94.0 | PFVP | 77 | 18 | 3 | 0 | 79 | 2.4 | 2.9 | 0.08 |
| 5 | 0.5 | 5.0 | 94.7 | PFVP | 243 | 78 | 21 | 1 | NT | 5.2 | 2.7 | 0.08 |
|  | 1 | 5.1 | 94.7 | PFVP | 194 | 37 | 3 | 0 | NT | 4.9 | 2.7 | 0.08 |
|  | 2 | 5.2 | 94.6 | PFVP | 448 | 118 | 28 | 0 | NT | 4.5 | 2.6 | 0.08 |
|  | 3 | 5.4 | 94.4 | PFVP | 333 | 104 | 14 | 0 | NT | 4.1 | 2.6 | 0.08 |
|  | 6 | 4.8 | 94.8 | PFVP | 335 | 79 | 12 | 0 | 82 | 4.8 | 2.7 | 0.08 |

TABLE 10

DP formulation screen results at 40° C./75% RH

| Formulation | Time (months) | Color | Turbidity | pH | icIEF (% Acidic) | (% Main Peak) | (% Basic) | SE-HPLC (% HMWS) | (% Main Peak) | (% LMWS) |
|---|---|---|---|---|---|---|---|---|---|---|
| 1 | 0.1 | NT | NT | 5.8 | NT | NT | NT | 0.7 | 99.0 | 0.3 |
|  | 0.25 | NT | NT | 5.8 | 47.7 | 45.5 | 6.8 | 0.7 | 99.0 | 0.3 |
|  | 0.5 | NT | NT | 5.8 | 52.2 | 41.5 | 6.4 | 0.7 | 98.8 | 0.5 |
|  | 0.75 | NT | NT | 5.8 | 56.2 | 37.8 | 6.0 | 0.7 | 98.7 | 0.6 |
|  | 1 | ≤BY7 | 0.01 | 5.8 | 62.3 | 32.7 | 5.0 | 0.8 | 98.5 | 0.7 |
| 2 | 0.1 | NT | NT | 5.5 | NT | NT | NT | 0.7 | 99.0 | 0.3 |
|  | 0.25 | NT | N | 5.5 | 48.3 | 44.2 | 7.4 | 0.8 | 98.9 | 0.3 |
|  | 0.5 | NT | NT | 5.5 | 52.1 | 41.1 | 6.8 | 0.8 | 98.8 | 0.5 |
|  | 0.75 | NT | NT | 5.5 | 56.5 | 37.2 | 6.4 | 0.8 | 98.6 | 0.6 |
|  | 1 | ≤BY7 | 0.01 | 5.5 | 61.9 | 32.8 | 5.4 | 0.8 | 98.4 | 0.8 |
| 3 | 0.1 | NT | NT | 5.8 | NT | NT | NT | 0.7 | 99.0 | 0.3 |
|  | 0.25 | NT | NT | 5.8 | 48.8 | 44.5 | 6.7 | 0.8 | 98.9 | 0.4 |
|  | 0.5 | NT | NT | 5.8 | 52.3 | 40.8 | 6.9 | 0.7 | 98.8 | 0.4 |
|  | 0.75 | NT | NT | 5.7 | 57.8 | 36.4 | 5.8 | 0.8 | 98.6 | 0.6 |
|  | 1 | ≤BY7 | 0.00 | 5.7 | 63.5 | 31.5 | 4.9 | 0.9 | 98.3 | 0.8 |
| 4 | 0.1 | NT | NT | 6.2 | NT | NT | NT | 0.7 | 99.0 | 0.3 |
|  | 0.25 | NT | NT | 6.2 | 50.0 | 43.5 | 6.5 | 0.7 | 98.9 | 0.3 |
|  | 0.5 | NT | NT | 6.2 | 54.6 | 39.3 | 6.1 | 0.8 | 98.8 | 0.5 |
|  | 0.75 | NT | NT | 6.2 | 59.8 | 34.7 | 5.5 | 0.7 | 98.7 | 0.6 |
|  | 1 | ≤BY7 | 0.01 | 6.2 | 66.0 | 29.3 | 4.6 | 0.7 | 98.5 | 0.8 |

TABLE 10-continued

DP formulation screen results at 40° C./75% RH

| | | | | | | | | | | | |
|---|---|---|---|---|---|---|---|---|---|---|---|
| 5 | 0.1 | NT | NT | 5.8 | NT | NT | NT | 0.7 | 99.0 | | 0.3 | |
| | 0.25 | NT | NT | 5.8 | 48.9 | 44.3 | 6.8 | 0.8 | 98.9 | | 0.4 | |
| | 0.5 | NT | NT | 5.8 | 53.1 | 40.4 | 6.6 | 0.8 | 98.8 | | 0.5 | |
| | 0.75 | NT | NT | 5.8 | 57.4 | 36.9 | 5.7 | 0.8 | 98.7 | | 0.6 | |
| | 1 | ≤BY7 | 0.00 | 5.8 | 63.4 | 31.6 | 5.0 | 0.8 | 98.5 | | 0.7 | |

| Formulation | Time (months) | Non-Reduced CE-SDS Sum of Pre-Peaks (%) | Non-Reduced CE-SDS (% Main Peak) | Visible Particulates | Subvisible Particulates (Cumulative Counts/ml) ≥2 μm | ≥5 μm | ≥10 μm | ≥25 μm | Potency (%) | L-Met (mM) | Oxidation Met257 (%) | PS20 (% w/v) |
|---|---|---|---|---|---|---|---|---|---|---|---|---|
| 1 | 0.1 | NT | NT | PFVP | NT | NT | NT | NT | NT | NT | NT | 0.06 |
| | 0.25 | 5.1 | 94.7 | PFVP | 38 | 6 | 0 | 0 | NT | 4.8 | 2.6 | 0.06 |
| | 0.5 | 5.4 | 94.3 | PFVP | 344 | 83 | 23 | 0 | NT | 4.9 | 2.7 | 0.06 |
| | 0.75 | 5.8 | 93.9 | PFVP | 26 | 3 | 0 | 0 | NT | 5.0 | 2.7 | 0.06 |
| | 1 | 6.5 | 93.3 | PFVP | 16 | 3 | 1 | 0 | 82 | 5.1 | 2.7 | 0.06 |
| 2 | 0.1 | NT | NT | PFVP | NT | NT | NT | NT | NT | NT | NT | 0.08 |
| | 0.25 | 5.2 | 94.6 | PFVP | 296 | 80 | 12 | 0 | NT | 2.4 | 2.7 | 0.08 |
| | 0.5 | 5.6 | 94.2 | PFVP | 411 | 99 | 25 | 0 | NT | 2.5 | 2.9 | 0.08 |
| | 0.75 | 6.1 | 93.6 | PFVP | 928 | 273 | 38 | 0 | NT | 2.5 | 2.8 | 0.08 |
| | 1 | 6.8 | 92.9 | PFVP | 133 | 55 | 11 | 0 | 90 | 2.4 | 2.8 | 0.08 |
| 3 | 0.1 | NT | NT | PFVP | NT | NT | NT | NT | NT | NT | NT | 0.08 |
| | 0.25 | 5.1 | 94.9 | PFVP | 31 | 8 | 1 | 0 | NT | 2.4 | NR | 0.08 |
| | 0.5 | 5.5 | 94.5 | PFVP | 172 | 46 | 18 | 0 | NT | 2.5 | 2.8 | 0.08 |
| | 0.75 | 6.0 | 94.0 | PFVP | 403 | 93 | 9 | 0 | NT | 2.6 | 2.8 | 0.08 |
| | 1 | 6.7 | 93.4 | PFVP | 167 | 59 | 8 | 0 | 101 | 2.4 | 2.9 | 0.08 |
| 4 | 0.1 | NT | NT | PFVP | NT | NT | NT | NT | NT | NT | NT | 0.08 |
| | 0.25 | 4.9 | 94.9 | PFVP | 123 | 44 | 4 | 0 | NT | 2.5 | 2.8 | 0.08 |
| | 0.5 | 5.3 | 94.5 | PFVP | 246 | 60 | 12 | 2 | NT | 2.5 | 2.9 | 0.08 |
| | 0.75 | 5.8 | 94.0 | PFVP | 489 | 114 | 9 | 0 | NT | 2.5 | 2.7 | 0.08 |
| | 1 | 6.3 | 93.4 | PFVP | 61 | 18 | 1 | 0 | 79 | 2.4 | 2.9 | 0.08 |
| 5 | 0.1 | NT | NT | PFVP | NT | NT | NT | NT | NT | NT | NT | 0.08 |
| | 0.25 | 5.1 | 94.6 | PFVP | 237 | 60 | 8 | 0 | NT | 4.9 | 2.7 | 0.09 |
| | 0.5 | 5.4 | 94.3 | PFVP | 312 | 68 | 20 | 0 | NT | 5.0 | 2.8 | 0.08 |
| | 0.75 | 6.0 | 93.8 | PFVP | 322 | 124 | 2 | 0 | NT | 4.9 | 2.9 | 0.08 |
| | 1 | 6.6 | 93.1 | PFVP | 105 | 36 | 8 | 0 | 99 | 4.8 | 2.8 | 0.08 |

3.6 DS Formulation Screen

DS stability was assessed in stainless steel mini-cans. Samples included the target formulation (Formulation 1), Formulation 2, and Formulation 3, having compositions shown in Table 11. All formulations contained 10 mg/ml mosunetuzumab and 0.06% (w/v) PS20. In these examples the molar ratio of surfactant to mosunetuzumab is about 7. Formulations 2 and 3 are high-risk formulations for oxidation at a relatively low pH and high pH, respectively. The risk of accelerated protein oxidation by metal leachables was assessed by incubating DS in surface-worn mini-cans with various fill volumes to quantify the impact of headspace.

TABLE 11

DS formulation summary

| Formulation | His acetate (mM) | pH | Sucrose (mM) | Methionine (mM) |
|---|---|---|---|---|
| 1 (Target) | 10 | 5.8 | 240 | 5 |
| 2 | 15 | 5.5 | 160 | 2.5 |
| 3 | 15 | 6.1 | 160 | 2.5 |

Each formulation was sterile-filled and filled into 316L 25 ml stainless steel mini-cans with a 15 ml fill volume. The mini-cans were stored upright on stability at real-time (−20° C.), accelerated (2° C.-8° C.), stressed (25° C., 60% relative humidity; RH) conditions, and selectively at −40° C. Mini-cans were stored under frozen conditions underwent no more than three freeze-thaw cycles. In order to control for mini-can variability, two cans were placed on stability for most temperature conditions.

To test for protein oxidation induced by metal leachables, a total of four 45-ml mini-cans that exhibited surface wear (pitting, scratches, etc.) were selected and filled with the low pH formulation (pH 5.5), which was considered high-risk for protein oxidation. These mini-cans were placed on stability at 2-8° C. and 25° C., 60% RH (two mini-cans at each temperature). The DS fill volumes were varied with a high fill volume (40 ml) and low fill volume (15 ml) in the mini-cans to generate variability in headspace.

Assays were performed to observe pH, oxidation (by peptide mapping), size variations (by SE-HPLC), charge variants (by mCE-SDS and iCIEF), color and appearance, sub-visible particles (by HIAC), visible particles, concentration (by UV-Spec Scan), turbidity, potency, and PS20 concentration (by ELSD). No changes were observed for any formulation tested after storage for 12 months at −40° C. or −20° C., and no changes were observed for any formulation tested after storage at 5° C. for six months. The high and low fill samples in the surface-worn 45-ml mini-cans showed no difference compared to samples stored in the 25-ml mini-cans at 5° C.

In summary, mosunetuzumab DS was stable within pH 5.5-6.1, even at the high-risk formulations for oxidation formulation conditions (high His and low Met for oxidation, low sucrose for frozen stability), and when challenging for metal-leachable induced oxidation (low fill volume in surface worn mini-can). Thus, these data show that such compositions (e.g., compositions having high His, low Met, and low sucrose) can also be used with levels of protein up to about 10 mg/ml, as necessary in some DS formulations.

3.7 DS Formulations Confirmatory Stability Study (Additional Formulations)

Additional DS formulations were tested to assess whether low histidine and high Met concentrations had an impact on DS stability. Stability had not previously been tested for histidine acetate concentrations less than the targeted 10 mM, or for methionine concentrations greater than 10 mM. Formulations are shown in Table 12, below. All formulations contained 10 mg/ml mosunetuzumab and 0.06% (w/v) PS20. In these formulations the molar ratio of surfactant mosunetuzumab is about 7.

TABLE 12

DS formulation confirmatory stability study (additional formulations)

| Formulation | His acetate (mM) | pH | Sucrose (mM) | Methionine (mM) |
|---|---|---|---|---|
| 1 (Target) | 10 | 5.8 | 240 | 10 |
| 2 | 5 | 5.8 | 240 | 15 |

Each formulation was sterile-filtered and filled into 316L 25-ml stainless steel mini-cans with a 16 ml fill volume. The mini-cans were stored upright on stability at accelerated (2-8° C.) and stressed (25° C./60% RH). In order to control for mini-can variability, two cans were placed on stability.

Assays were conducted to test for pH, oxidation (by peptide mapping), methionine concentration, potency, size variants (by SE-HPLC), charge variants (by mCE-SDS and iCIEF), color and appearance, visible particles, concentration (by UV-Spec Scan), turbidity, and PS20 concentration (ELSD).

No change was observed for any formulation tested after storage for one month at 5° C. High methionine and low histidine formulations showed no difference compared to target samples. After storage at 25° C. for one month, consistent changes through both DS formulations were observed, with a slight increase in LMWS by SE-HPLC (0.2%) and CE-SDS and a decrease in main peak and increase in acidic peak by iCIEF. No change was observed for other assays. This study demonstrated that mosunetuzumab DS was stable within a methionine concentration range of 10-15 mM and a histidine acetate concentration range of 5-10 mM.

3.8 DS Freeze-Thaw Stability

Freeze-thaw stability of DS was evaluated by stressing each formulation specified in Table 11 with seven freeze-thaw cycles in mini-cans. The 25 ml 316L stainless steel mini-cans were filled with 16 ml of sterile-filtered material. One mini-can was prepared for each formulation. A freeze-thaw cycle consisted of two hours at −40° C., followed by at least 8 hours at −20° C., followed by storage at room temperature until the samples are completely thawed (approximately 2-3 hours). Before sampling, material was mixed by gently inverting the can approximately ten times. Each mini-can was sampled for 2.5 ml aseptically after the third, fourth, fifth, and seventh cycles.

Assays tested for sub-visible particles (HIAC), visible particles, turbidity (UV spec), oxidation (peptide map), and sizing (SE-HPLC). As shown in Table 13, no changes were observed. These data confirmed that the DS was stable through seven freeze-thaw cycles.

TABLE 13

Freeze and thaw stability of DS formulation screen samples

| Freeze Thaw Cycle | Color | Turbidity | Oxidation (% Met257) | SE-HPLC (% HMWS) | (% Main Peak) | (% LMWS) | Visible Particles | Subvisible Particulates (Cumulative Counts/ml) | | | |
|---|---|---|---|---|---|---|---|---|---|---|---|
| | | | | | | | | ≥2 μm | ≥5 μm | ≥10 μm | ≥25 μm |
| 1 (Target) | 0 | ≤BY7 | 0.05 | 2.8 | 1.0 | 98.7 | 0.3 | PFVP | 33 | 8 | 3 | 0 |
| | 3 | ≤BY7 | 0.07 | NT | 1.0 | 98.7 | 0.3 | PFVP | 19 | 9 | 8 | 2 |
| | 4 | ≤BY7 | 0.05 | NT | 1.0 | 98.8 | 0.3 | PFVP | 240 | 83 | 40 | 1 |
| | 5 | ≤BY7 | 0.05 | NT | 1.0 | 98.8 | 0.3 | PFVP | 317 | 90 | 37 | 2 |
| | 7 | ≤BY7 | 0.03 | 2.8 | 1.0 | 98.8 | 0.3 | PFVP | 543 | 150 | 49 | 2 |
| 2 | 0 | ≤BY7 | 0.05 | 2.8 | 0.9 | 98.8 | 0.3 | PFVP | 14 | 8 | 8 | 3 |
| | 3 | ≤BY7 | 0.04 | NT | 1.0 | 98.8 | 0.3 | PFVP | 165 | 50 | 22 | 4 |
| | 4 | ≤BY7 | 0.07 | NT | 1.0 | 98.7 | 0.3 | PFVP | 353 | 117 | 44 | 2 |
| | 5 | ≤BY7 | 0.05 | NT | 0.9 | 98.8 | 0.3 | PFVP | 532 | 162 | 73 | 3 |
| | 7 | ≤BY7 | 0.03 | 2.8 | 1.0 | 98.8 | 0.3 | PFVP | 806 | 252 | 73 | 4 |
| 3 | 0 | ≤BY7 | 0.05 | 2.8 | 1.0 | 98.7 | 0.3 | PFVP | 23 | 3 | 1 | 0 |
| | 3 | ≤BY7 | 0.04 | NT | 1.0 | 98.7 | 0.3 | PFVP | 132 | 20 | 3 | 0 |
| | 4 | ≤BY7 | 0.04 | NT | 1.0 | 98.7 | 0.3 | PFVP | 181 | 55 | 15 | 0 |
| | 5 | ≤BY7 | 0.02 | NT | 1.0 | 98.7 | 0.3 | PFVP | 403 | 123 | 33 | 1 |
| | 7 | ≤BY7 | 0.04 | 2.8 | 1.0 | 98.8 | 0.2 | PFVP | 643 | 210 | 67 | 2 |

3.9 Donnan Effect

Donnan Effect (an unequal distribution of permeant charged ions on either side of a semipermeable membrane which occurs in the presence of impermeant charged ions) was assessed by measuring pH of in-process samples taken from each diavolume during diafiltration (DF). The pH of DF buffer, conditioning buffer, recovered pool, diluted pool, and conditioned material was also measured. L-histidine concentration was measured in LSPD for select samples using a UPLC analysis for free histidine assay.

Figure 12:
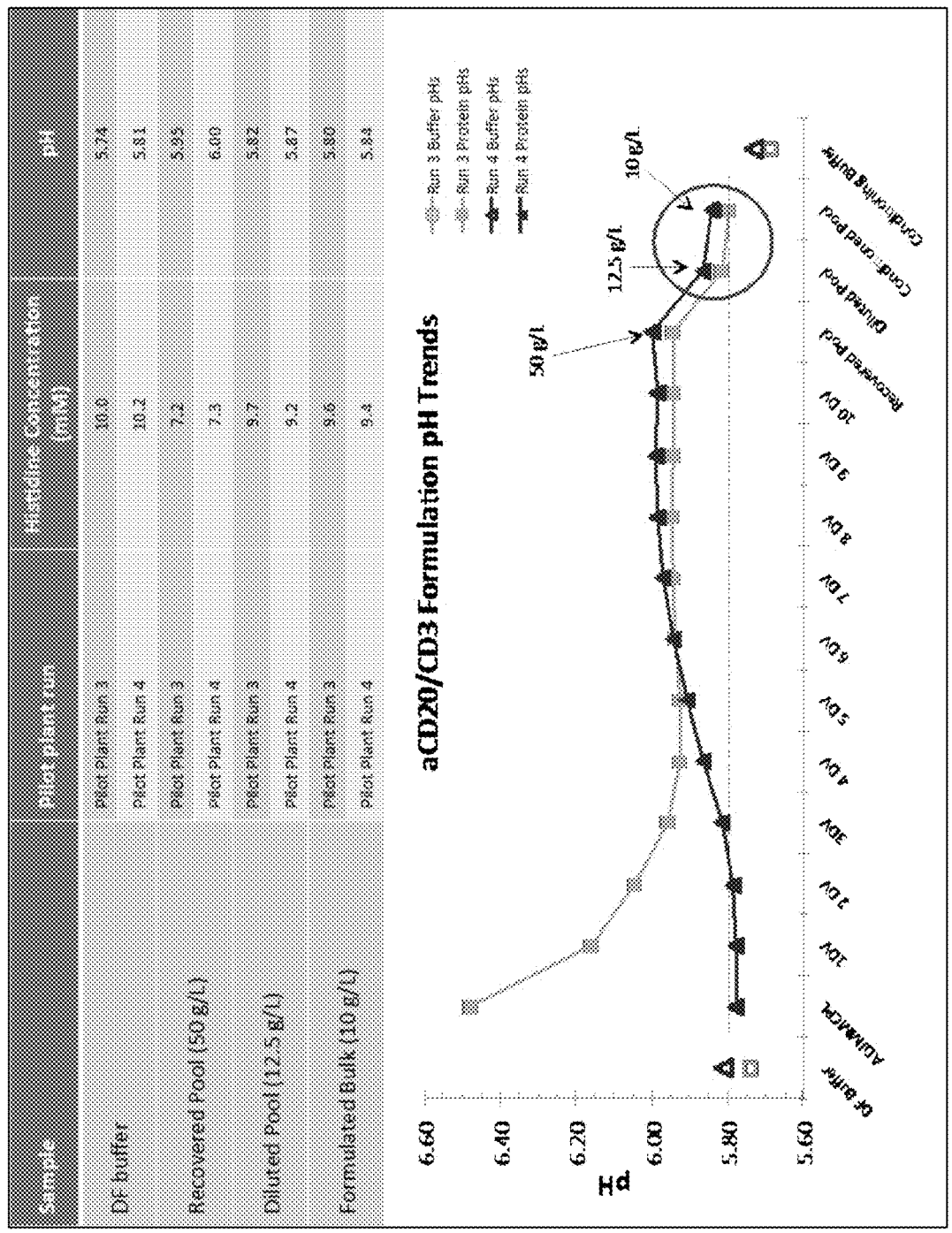
FIG. 12 is a graph showing the Donnan Effect on pH values of mosunetuzumab compositions.

Results of the experiment are summarized in FIG. 12. Donnan Effect was observed with a pH increase of about 0.2 (relative to the DF buffer pH of 5.8) in the recovered pool at a protein centration of about 50 g/L. With a 5× dilution factor after dilution and conditioning to a protein concentration of 10 g/L, the pH returned to the target of pH 5.8. The histidine concentration in the diluted pool and conditioned pool was approximately 10 mM.

Example 4: Component Selection Based on Formulation Development

The formulation development studies described in Example 3 above informed selection of various components (e.g., protein, surfactant, antioxidant, buffer, pH, sucrose, and containers) as described below.

4.1. Protein

Protein concentration was selected to deliver the Phase III dose accurately via IV bag without the use of a diluent. The day-one fractionated dose was anticipated to be as low as 0.8-1.0 mg. IV bag shaking studies of Example 3.1 demonstrated that, to deliver such a low dose, a low DP protein concentration is necessary to ensure there is sufficient surfactant in the diluted dose solution to protect the protein against mechanical agitation. Further, a lower protein concentration allows a larger dose volume and, accordingly, more accurate dose delivery. For these reasons, DP protein concentration was selected as 1 mg/ml. The DS concentration was selected as 10 mg/ml to balance a reasonable dilution factor from DS to DP and the facility fit for DS storage.

4.2. Surfactant

Three surfactant types were evaluated: PS20, super refined PS20 (srPS20), and P188. SrPS20 was ruled out due to its increased risk of inducing protein oxidation, fragmentation, and aggregation in low protein concentration formulations (Example 3.2). The minimum required level of PS20 and P188 was determined to be 0.05% (w/v) and 0.08% (w/v), respectively from the IV bag agitation study (Example 3.1). Both PS20 and P188 showed no impact on protein quality under thermal stress (Example 3.2). PS20 was selected as the surfactant type, in view of the relatively low concentration required, the low risk of ester bond hydrolysis due to low protein concentration (and, accordingly, low abundance of any lipase impurities), and low risk of surfactant oxidation due to the inclusion of antioxidant. Based on the minimum required level determined from IV bag shaking studies (Example 3.1), 0.06% (w/v) was selected as PS20 target concentration (molar ratio of surfactant to mosunetuzumab of about 71 for formulations containing 1 mg/ml mosunetuzumab, and 0.05-0.07% (w/v) was determined as DS release specification for PS20.

4.3. Antioxidant

Oxidation was identified as a major risk for the low protein concentration formulation of mosunetuzumab in the knowledge building study, and L-Met protected the formulation from oxidation. During formulation development, oxidation was considered the major risk for evaluation, and the worst-case formulation for oxidation was challenged under thermal stress and ambient light stress conditions (Example 3.3). These studies indicated that Met is required, whereas NAT does not add additional benefit with respect to light-stress induced oxidation.

Met concentration was optimized in a hydrogen peroxide spiking study with thermal stress (Example 3.4). In this stress model, 5 mM Met was required to fully protect the formulation from protein oxidation. Met-mediated quenching of oxidation immediately after addition of hydrogen peroxide is beneficial for formulation stability, since DS and DP may experience residual hydrogen peroxide challenge during the manufacturing process, given that vaporized hydrogen peroxide is a common sterilization reagent for equipment, such as isolators. To ensure the DS and DP formulation stability against oxidation stress from multiple sources, and considering manufacturing variability of Met concentration, 10 mM was selected as the concentration of Met in the DS and DP formulations.

4.4. Buffer

Histidine acetate (His) was used as the buffer species in the formulation 1 and demonstrated capability of buffering the DS and DP formulation at pH 5.5-6.1. Therefore, His was selected as the buffer species for the formulation. The knowledge building study showed His concentration positively impacted acidic peak formation in the range of 10-30 mM. Further studies demonstrated that formulations with 10 mM His are less prone to oxidation compared to those with 30 mM His, in the absence of antioxidant (Example 3.3). His concentrations of 10 mM and lower (e.g., 5 mM) were sufficient to buffer the DS and DP solution at pH 5.5-6.1. The pH was confirmed to be stable on long term real-time, accelerated, and stress stability in formulations containing 10 mM His (Examples 3.5 and 3.6). From the manufacturing perspective, given the pH shift observed in the Donnan Effect evaluation (Example 3.8), His concentration may shift in the recovered pool at 50 g/L. However, given the high dilution factor from recovered pool to diluted pool (12.5 g/L) and DS (10 g/L), the His concentration returned to close to 10 mM. Therefore, the impact of Donnan Effect on the final DS and DP His concentration is minimal. With all these considerations, 10 mM histidine acetate was selected as the target buffer concentration.

4.5. pH

Long-term stability of the early stage formulation demonstrated that the target pH 5.8 is adequate for stability. The knowledge building study showed that pH has a small positive impact on acidic peak formation and no impact on aggregation or fragmentation. DP and DS screening studies on target formulation and high-risk oxidation formulations showed that the impact of pH (5.5-6.1) is minimal on real-time, accelerated, and stress stability (Examples 3.5 and 3.6). Based on these results, the formulation pH was selected as pH 5.8.

4.6. Sucrose

Knowledge-building studies did not show any significant impact of sucrose concentration on product quality attributes when the high-risk oxidation formulation was excluded from statistical analysis. A relatively low concentration of sucrose (160 mM) was evaluated in the DP and DS screen study, as well as the multiple freeze and thaw study for DS, and showed no impact on stability when compared to target formulation (Examples 3.5, 3.6, and 3.7).

4.7. Containers 316L stainless steel mini-cans were used in the DS formulation screen. Multiple freeze-thaw studies demonstrated adequate stability (Examples 3.6 and 3.7). Stainless steel is considered a high-risk container for metal leachable-induced degradation of protein (e.g., compared to HASTELLOY®). These results suggest that the DS formulation is stable in stainless steel and HASTELLOY®. 316L stainless steel and HASTELLOY® mini-cans will be evaluated in the DS representative study to provide additional supportive data for allowing use of either type of container for DS storage.

It is necessary that DP vial configuration supports delivery of a wide range of doses in clinical trials, according to the double step-fractionated dosing scheme, which calls for two low fractional doses (e.g., 1 mg and 2 mg) and one full dose (e.g., 5-20 mg). To best support this range of doses, a 20 ml vial with a 13.5 ml nominal fill was selected.

IX. Embodiments

Some embodiments of the technology described herein can be defined according to any of the following numbered embodiments:

1. A pharmaceutical composition comprising mosunetuzumab, polysorbate 20 (PS20), methionine, a buffering agent, and a carrier, wherein the concentration of PS20 is from 0.01% to 0.1% weight-by-volume (w/v), the concentration of methionine is from 1 mM to 50 mM, and the concentration of the buffering agent is from 5 mM to 20 mM.

2. The pharmaceutical composition of embodiment 1, wherein the concentration of mosunetuzumab is about 15 mg/ml or less.

3. The pharmaceutical composition of embodiment 1 or 2, wherein the molar ratio of the PS20 to mosunetuzumab is less than 100.

4. The pharmaceutical composition of embodiment 3, wherein the molar ratio of the PS20 to mosunetuzumab is between 50 and 100.

5. The pharmaceutical composition of embodiment 4, wherein the molar ratio of the PS20 to mosunetuzumab is about 71.

6. The pharmaceutical composition of any one of embodiments 1-5, wherein the concentration of mosunetuzumab is between about 0.5 mg/ml to about 2 mg/ml.

7. The pharmaceutical composition of embodiment 6, wherein the concentration of mosunetuzumab is about 1 mg/ml.

8. The pharmaceutical composition of any one of embodiments 1-7, wherein the pharmaceutical composition is formulated as a drug product (DP).

9. The pharmaceutical composition of any one of embodiments 1-8, wherein the concentration of methionine is from about 2.5 mM to about 20 mM.

10. The pharmaceutical composition of embodiment 9, wherein the concentration of methionine is about 10 mM.

11. The pharmaceutical composition of any one of embodiments 1-10, wherein the buffering agent is a histidine, a phosphate, a succinate, an acetate, or a combination thereof.

12. The pharmaceutical composition of embodiment 11, wherein the buffering agent is a histidine.

13. The pharmaceutical composition of embodiment 12, wherein the histidine is histidine acetate.

14. The pharmaceutical composition of any one of embodiments 1-13, wherein the concentration of the buffering agent is from about 8 mM to about 12 mM.

15. The pharmaceutical composition of embodiment 14, wherein the concentration of the buffering agent is about 10 mM.

16. The pharmaceutical composition of any one of embodiments 1-15, wherein the buffering agent is histidine acetate at a concentration from about 8 mM to about 12 mM.

17. The pharmaceutical composition of embodiment 16, wherein the concentration of histidine acetate is about 10 mM.

18. The pharmaceutical composition of any one of embodiments 1-17, further comprising a tonicity agent.

19. The pharmaceutical composition of embodiment 18, wherein the tonicity agent is a sugar, an amino acid, or a salt.

20. The pharmaceutical composition of embodiment 19, wherein the tonicity agent is a sugar.

21. The pharmaceutical composition of embodiment 20, wherein the sugar is sucrose, glucose, glycerol, or trehalose.

22. The pharmaceutical composition of embodiment 21, wherein the sugar is sucrose.

23. The pharmaceutical composition of any one of embodiments 18-22, wherein the tonicity agent is at a concentration from about 100 mM to about 500 mM.

24. The pharmaceutical composition of embodiment 23, wherein the concentration of the tonicity agent is from about 200 mM to about 300 mM.

25. The pharmaceutical composition of embodiment 24, wherein the concentration of the tonicity agent is about 240 mM.

26. The pharmaceutical composition of any one of embodiments 1-25, wherein the pharmaceutical composition has a pH from about 4.5 to about 8.

27. The pharmaceutical composition of embodiment 26, wherein the pH of the pharmaceutical composition is from about 5.5 to about 6.1.

28. The pharmaceutical composition of embodiment 27, wherein the pH of the pharmaceutical composition is about 5.8.

29. The pharmaceutical composition of any one of embodiments 1-28, wherein mosunetuzumab has a methionine at position 257 of the Fc region (EU numbering), and wherein oxidation of the methionine at position 257 of the Fc region is less than about 10% over two weeks at 40° C.

30. The pharmaceutical composition of embodiment 29, wherein the oxidation of methionine at position 257 of the Fc region is no more than about 6% over two weeks at 40° C.

31. A pharmaceutical composition comprising mosunetuzumab, a surfactant, methionine, and a carrier, wherein the pharmaceutical composition has a pH of about 5.8, and wherein:
  (i) the concentration of mosunetuzumab is about 10 mg/ml or less,
  (ii) the concentration of the surfactant is from about 0.05% to about 0.1% (w/v), and
  (iii) the concentration of methionine is of about 10 mM.

32. The pharmaceutical composition of embodiment 31, wherein the molar ratio of the surfactant to mosunetuzumab is 100 or less.

33. The pharmaceutical composition of embodiment 31 or 32, wherein the surfactant is PS20 or poloxamer 188 (P188).

34. The pharmaceutical composition of embodiment 33, wherein the surfactant is PS20 and the concentration of PS20 is about 0.06% (w/v).

35. The pharmaceutical composition of embodiment 34, wherein the molar ratio of the PS20 to mosunetuzumab is from about 50 to about 100.

36. The pharmaceutical composition of embodiment 35, wherein the molar ratio of the PS20 to mosunetuzumab is about 71.

37. The pharmaceutical composition of embodiment 33, wherein the surfactant is P188 and the concentration of P188 is about 0.1% (w/v).

38. The pharmaceutical composition of embodiment 37, wherein the molar ratio of the P188 to mosunetuzumab is from about 5 to about 25.

39. The pharmaceutical composition of embodiment 38, wherein the molar ratio of the P188 to mosunetuzumab is about 17.

40. The pharmaceutical composition of any one of embodiments 31-39, wherein the concentration of mosunetuzumab is between about 0.5 mg/ml to about 2 mg/ml.

41. The pharmaceutical composition of embodiment 40, wherein the concentration of mosunetuzumab is about 1 mg/ml.

42. The pharmaceutical composition of any one of embodiments 35-41, wherein the pharmaceutical composition is formulated as a DP.

43. The pharmaceutical composition of any one of embodiments 31-42, further comprising histidine acetate at a concentration of about 10 mM and/or sucrose at a concentration of about 240 mM.

44. The pharmaceutical composition of any one of embodiments 1-43, wherein the pharmaceutical composition is in a unit dosage form.

45. The pharmaceutical composition of embodiment 44, wherein the unit dosage form is a liquid formulation for dilution.

46. The pharmaceutical composition of embodiment 45, wherein the liquid formulation for dilution is supplied in a container having a volume of about 50 ml.

47. The pharmaceutical composition of embodiment 45, wherein the liquid formulation for dilution is supplied in a container having a volume of about 2 ml.

48. The pharmaceutical composition of embodiment 45 or 46, wherein the volume of the liquid formulation for dilution is between 20-40 ml.

49. The pharmaceutical composition of embodiment 48, wherein the volume of the liquid formulation for dilution is about 30 ml.

50. The pharmaceutical composition of embodiment 45 or 47, wherein the volume of the liquid formulation for dilution is between 0.2-2 ml.

51. The pharmaceutical composition of embodiment 50, wherein the volume of the liquid formulation for dilution is about 1 ml.

52. The pharmaceutical composition of any one of embodiments 45-51, wherein the liquid formulation is for dilution with a normal saline solution comprising 0.45% or 0.9% (w/v) NaCl.

53. The pharmaceutical composition of any one of embodiments 1-52, wherein the pharmaceutical composition comprises no more than 1,000 particles having a diameter 2 μm per ml as detected by high accuracy liquid particle counting (HIAC).

54. The pharmaceutical composition of any one of embodiments 1-53, wherein the carrier is water.

55. The pharmaceutical composition of any one of embodiments 1-54, wherein the pharmaceutical composition has a shelf-life of at least 36 months when stored at 5° C.±3° C. and protected from light.

56. The pharmaceutical composition of any one of embodiments 1-55, wherein the pharmaceutical composition is stable through one or more freeze-thaw cycles.

57. The pharmaceutical composition of embodiment 56, wherein the pharmaceutical composition is stable through three or more freeze-thaw cycles.

58. The pharmaceutical composition of any one of embodiments 1-57, wherein the pharmaceutical composition is stable for about two weeks or longer at about 25° C.

59. The pharmaceutical composition of embodiment 58, wherein the pharmaceutical composition is stable for about four weeks or longer at about 25° C.

60. The pharmaceutical composition of any one of embodiments 1-59, wherein the pharmaceutical composition is stable for about 48 months or longer at −20° C.

61. The pharmaceutical composition of any one of embodiments 56-60, wherein stability is assessed by size-exclusion high-performance liquid chromatography (SE-HPLC).

62. The pharmaceutical composition of embodiment 61, wherein the pharmaceutical composition is determined to be stable if the pharmaceutical composition maintains a purity that is changed by less than 5% as measured by SE-HPLC.

63. The pharmaceutical composition of any one of embodiments 56-60, wherein stability is assessed by non-reduced capillary electrophoresis sodium dodecyl sulfate (CE-SDS) assay.

64. The pharmaceutical composition of embodiment 63, wherein the pharmaceutical composition is determined to be stable if the pharmaceutical composition maintains a purity that is changed by less than 5% as measured by non-reduced CE-SDS assay.

65. The pharmaceutical composition of embodiment 63 or 64, wherein the non-reduced CE-SDS assay is a microchip CE-SDS (mCE-SDS) assay.

66. The pharmaceutical composition of any one of embodiments 1-65, wherein the pharmaceutical composition has a purity of about 85% or higher as assessed by SE-HPLC.

67. The pharmaceutical composition of embodiment 66, wherein the pharmaceutical composition has a purity of about 90% or higher as assessed by SE-HPLC.

68. The pharmaceutical composition of embodiment 67, wherein the pharmaceutical composition has a purity of about 95% or higher as assessed by SE-HPLC.

69. The pharmaceutical composition of any one of embodiments 66-68, wherein the purity of the pharmaceutical composition as assessed by SE-HPLC is maintained about the same for about 36 months or longer at about 5° C.

70. The pharmaceutical composition of embodiment 69, wherein the purity of the pharmaceutical composition as assessed by SE-HPLC is maintained about the same for about 42 months or longer at about 5° C.

71. The pharmaceutical composition of embodiment 70, wherein the purity of the pharmaceutical composition as assessed by SE-HPLC is maintained about the same for about 64 months or longer at about 5° C.

72. The pharmaceutical composition of any one of embodiments 1-71, wherein the pharmaceutical composition has a purity of about 75% or higher as assessed by non-reduced CE-SDS assay.

73. The pharmaceutical composition of embodiment 72, wherein the pharmaceutical composition has a purity of about 80% or higher as assessed by non-reduced CE-SDS assay.

74. The pharmaceutical composition of embodiment 73, wherein the pharmaceutical composition has a purity of about 85% or higher as assessed by non-reduced CE-SDS assay.

75. The pharmaceutical composition of any one of embodiments 72-74, wherein the purity of the pharmaceutical composition as assessed by non-reduced CE-SDS assay is maintained for about 36 months or longer at about 5° C.

76. The pharmaceutical composition of embodiment 75, wherein the purity of the pharmaceutical composition as assessed by non-reduced CE-SDS assay is maintained for about 42 months or longer at about 5° C.

77. The pharmaceutical composition of any one of embodiments 72-76, wherein the non-reduced CE-SDS assay is a microchip CE-SDS (mCE-SDS) assay.

78. The pharmaceutical composition of any one of embodiments 1-77, wherein the pharmaceutical composition is formulated for intravenous administration.

79. The pharmaceutical composition of any one of embodiments 1-78, wherein the pharmaceutical composition does not contain a preservative.

80. The pharmaceutical composition of any one of embodiments 1-79, wherein the pharmaceutical composition comprises 1 mg/ml mosunetuzumab, 10 mM L-histidine acetate, 240 mM sucrose, 0.06% (w/v) PS20, and 10 mM methionine, pH 5.8, and wherein the pharmaceutical composition is formulated for administration by infusion after dilution with a normal saline solution comprising 0.45% or 0.9% NaCl.

81. The pharmaceutical composition of any one of embodiments 1-80 for use as a medicament.

82. The pharmaceutical composition of any one of embodiments 1-80 for use in treating or delaying progression of a cancer in a subject in need thereof.

83. The pharmaceutical composition of any one of embodiments 1-80 for use in enhancing immune function in a subject having a cancer.

84. The pharmaceutical composition of any one of embodiments 1-80 for use in treating or delaying progression of cancer, or for use in enhancing immune function in a subject having a cancer, wherein the cancer is a non-Hodgkin's lymphoma selected from the group consisting of chronic lymphoid leukemia (CLL), B cell lymphoma, splenic diffuse red pulp small B cell lymphoma, B cell lymphoma with features intermediate between diffuse large B cell lymphoma and Burkitt lymphoma, B cell lymphoma with features intermediate between diffuse large B cell lymphoma and classical Hodgkin lymphoma, diffuse large B cell lymphoma (DLBCL), germinal center B cell-like (GCB) DLBCL, activated B cell-like (ABC) DLBCL, primary cutaneous follicle center lymphoma, T-cell/histiocyte rich large B cell lymphoma, primary DLBCL of the central nervous system, primary cutaneous DLBCL (leg type), Epstein-Barr virus (EBV)-positive DLBCL of the elderly, DLBCL associated with chronic inflammation, primary mediastinal (thymic) large B cell lymphoma, intravascular large B cell lymphoma, ALK-positive large B cell lymphoma, large B cell lymphoma arising in HHV8-associated multicentric Castleman disease, B cell leukemia, follicular lymphoma (FL), mantle cell lymphoma (MCL), acute myeloid leukemia (AML), marginal zone lymphoma (MZL), small lymphocytic leukemia (SLL), lymphoplasmacytic lymphoma (LL), Waldenstrom macroglobulinemia (WM), central nervous system lymphoma (CNSL), Burkitt's lymphoma (BL), B cell prolymphocytic leukemia, splenic marginal zone lymphoma, hairy cell leukemia, splenic lymphoma/leukemia, hairy cell leukemia variant, α heavy chain disease, γ heavy chain disease, μ heavy chain disease, plasma cell myeloma, solitary plasmacytoma of bone, extraosseous plasmacytoma, extranodal marginal zone lymphoma of mucosa-associated lymphoid tissue (MALT lymphoma), nodal marginal zone lymphoma, pediatric nodal marginal zone lymphoma, pediatric follicular lymphoma, lymphomatoid granulomatosis, plasmablastic lymphoma, and primary effusion lymphoma.

85. The pharmaceutical composition for use of embodiment 84, wherein the NHL is GCB DLBCL, ABC DLBCL, FL, MCL, AML, CLL, MZL, SLL, LL, WM, CNSL, or BL.

86. The pharmaceutical composition for use of embodiment 85, wherein the NHL is FL.

87. The pharmaceutical composition for use of embodiment 86, wherein the FL is relapsed and/or refractory (R/R).

88. The pharmaceutical composition for use of embodiment 87, wherein the subject having the R/R FL has relapsed after or is refractory to at least two prior systemic therapies.

89. The pharmaceutical composition for use of embodiment 88, wherein the subject has received prior systemic therapy comprising an anti-CD20 monoclonal antibody.

90. The pharmaceutical composition for use of embodiment 88 or 89, wherein the subject has received prior systemic therapy comprising an alkylating agent.

91. The pharmaceutical composition for use of any one of embodiments 82-90, wherein mosunetuzumab is formulated for administration to the subject at a dose from about 0.1 mg to about 100 mg.

92. The pharmaceutical composition for use of embodiment 91, wherein mosunetuzumab is formulated for administration to the subject at a dose from about 1 mg to about 60 mg.

93. The pharmaceutical composition for use of embodiment 92, wherein mosunetuzumab is formulated for administration to the subject at a dose of about 1 mg, 2 mg, 6 mg, 9 mg, 13.5 mg, 20 mg, 30 mg, or 60 mg.

94. The pharmaceutical composition for use of embodiment 93, wherein mosunetuzumab is formulated for administration to the subject at a dose of about 1 mg, 2 mg, 30 mg, or 60 mg.

95. The pharmaceutical composition for use of any one of embodiments 82-94, wherein the pharmaceutical composition is formulated for administration to the subject after dilution with a normal saline solution comprising 0.45% or 0.9% (w/v) NaCl.

96. The pharmaceutical composition for use of embodiment 95, wherein after dilution with the normal saline solution, the concentration of mosunetuzumab is from about 0.01 mg/ml to about 0.3 mg/ml.

97. The pharmaceutical composition for use of embodiment 96, wherein after dilution with the normal saline solution, the concentration of mosunetuzumab is about 0.01 mg/ml, about 0.02 mg/ml, about 0.04 mg/ml, about 0.12 mg/ml, about 0.24 mg/ml, or about 0.3 mg/ml.

98. The pharmaceutical composition for use of any one of embodiments 82-97, wherein the pharmaceutical composition is for use in combination with at least one additional therapeutic agent.

99. The pharmaceutical composition for use of embodiment 98, wherein the at least one additional therapeutic agent comprises a PD-1 axis binding antagonist.

100. The pharmaceutical composition for use of embodiment 99, wherein the PD-1 axis binding antagonist is selected from the group consisting of a PD-L1 binding antagonist, a PD-1 binding antagonist, and a PD-L2 binding antagonist.

101. The pharmaceutical composition for use of embodiment 100, wherein the PD-1 axis binding antagonist is a PD-L1 binding antagonist.

102. The pharmaceutical composition for use of embodiment 101, wherein the PD-L1 binding antagonist is selected from the group consisting of atezolizumab (MPDL3280A), MDX-1105 (BMS-936559), and MED14736 (durvalumab).

103. The pharmaceutical composition for use of embodiment 100, wherein the PD-1 axis binding antagonist is a PD-1 binding antagonist.

104. The pharmaceutical composition for use of embodiment 103, wherein the PD-1 binding antagonist is selected from the group consisting of MDX-1106 (nivolumab), MK-3475 (lambrolizumab), AMG 404, REGN2810 (cemiplimab), and AMP-224.

105. The pharmaceutical composition for use of embodiment 100, wherein the PD-1 axis binding antagonist is a PD-L2 binding antagonist.

106. The pharmaceutical composition for use of embodiment 105, wherein the PD-L2 binding antagonist is an antibody or an immunoadhesin.

107. The pharmaceutical composition for use of embodiment 98, wherein the at least one additional therapeutic agent comprises obinutuzumab, rituximab, a corticosteroid, or tocilizumab.

108. The pharmaceutical composition for use of embodiment 98, wherein the at least one additional therapeutic agent comprises an antibody-drug conjugate (ADC)

109. The pharmaceutical composition for use of embodiment 108, wherein the ADC is an anti-CD79b ADC.

110. The pharmaceutical composition for use of embodiment 109, wherein the anti-CD79b ADC is polatuzumab vedotin.

111. The pharmaceutical composition for use of any one of embodiments 82-110, wherein the pharmaceutical composition is formulated for administration intravenously.

112. The pharmaceutical composition for use of any one of embodiments 82-111, wherein the subject is a human.

113. A method of treating or delaying the progression of a cancer in a subject in need thereof, the method comprising administering to the subject an effective amount of the pharmaceutical composition of any one of embodiments 1-80.

114. A method of enhancing immune function in a subject having a cancer, the method comprising administering to the subject an effective amount of the pharmaceutical composition of any one of embodiments 1-80.

115. A method of treating or delaying the progression of a cancer in a subject in need thereof or enhancing immune function in a subject having a cancer, the method comprising administering to the subject an effective amount of the pharmaceutical composition of any one of embodiments 1-80, wherein the cancer is an NHL selected from the group consisting of CLL, B cell lymphoma, splenic diffuse red pulp small B cell lymphoma, B cell lymphoma with features intermediate between diffuse large B cell lymphoma and Burkitt lymphoma, B cell lymphoma with features intermediate between diffuse large B cell lymphoma and classical Hodgkin lymphoma, DLBCL, GCB DLBCL, ABC DLBCL, primary cutaneous follicle center lymphoma, T-cell/histiocyte rich large B cell lymphoma, primary DLBCL of the central nervous system, primary cutaneous DLBCL (leg type), EBV-positive DLBCL of the elderly, DLBCL associated with chronic inflammation, primary mediastinal (thymic) large B cell lymphoma, intravascular large B cell lymphoma, ALK-positive large B cell lymphoma, large B cell lymphoma arising in HHV8-associated multicentric Castleman disease, B cell leukemia, FL, MCL, AML, MZL, SLL, LL, WM, CNSL, BL, B cell prolymphocytic leukemia, splenic marginal zone lymphoma, hairy cell leukemia, splenic lymphoma/leukemia, hairy cell leukemia variant, α heavy chain disease, γ heavy chain disease, μ heavy chain disease, plasma cell myeloma, solitary plasmacytoma of bone, extraosseous plasmacytoma, MALT lymphoma, nodal marginal zone lymphoma, pediatric nodal marginal zone lymphoma, pediatric follicular lymphoma, lymphomatoid granulomatosis, plasmablastic lymphoma, and primary effusion lymphoma.

116. The method of embodiment 115, wherein the NHL is GCB DLBCL, ABC DLBCL, FL, MCL, AML, CLL, MZL, SLL, LL, WM, CNSL, or BL.

117. The method of embodiment 116, wherein the NHL is FL.

118. The method of embodiment 117, wherein the FL is relapsed and/or refractory (R/R).

119. The method of embodiment 118, wherein the subject having the R/R FL has relapsed after or is refractory to at least two prior systemic therapies.

120. The method of embodiment 119, wherein the subject has received prior systemic therapy comprising an anti-CD20 monoclonal antibody.

121. The method of embodiment 119 or 120, wherein the subject has received prior systemic therapy comprising an alkylating agent.

122. The method of any one of embodiments 113-121, wherein mosunetuzumab is administered to the subject at a dose from about 0.1 mg to about 100 mg.

123. The method of embodiment 122, wherein mosunetuzumab is administered to the subject at a dose from about 1 mg to about 60 mg.

124. The method of embodiment 123, wherein mosunetuzumab is administered to the subject at a dose of about 1 mg, 2 mg, 6 mg, 9 mg, 13.5 mg, 20 mg, 30 mg, or 60 mg.

125. The method of embodiment 124, wherein mosunetuzumab is administered to the subject at a dose of about 1 mg, 2 mg, 30 mg, or 60 mg.

126. The method of any one of embodiments 113-125, wherein the pharmaceutical composition is administered to the subject after dilution with a normal saline solution comprising 0.45% or 0.9% (w/v) NaCl.

127. The method of embodiment 126, wherein after dilution with the normal saline solution, the concentration of mosunetuzumab is from about 0.01 mg/ml to about 0.3 mg/ml.

128. The method of embodiment 127, wherein after dilution with the normal saline solution, the concentration of mosunetuzumab is about 0.01 mg/ml, about 0.02 mg/ml, about 0.04 mg/ml, about 0.12 mg/ml, about 0.24 mg/ml, or about 0.3 mg/ml.

129. The method of any one of embodiments 113-128, wherein mosunetuzumab is administered to the subject in a dosing regimen comprising at least three 21-day dosing cycles, wherein
(a) the first 21-day dosing cycle comprises a first dose (C1D1), a second dose (C1D2), and a third dose (C1D3) of mosunetuzumab administered to the subject on days 1, 8, and 15, respectively, of the first dosing cycle, wherein the C1D1 is about 1 mg, the C1D2 is about 2 mg, and the C1D3 is about 60 mg;
(b) the second dosing cycle comprises a single dose (C2D1) of mosunetuzumab administered to the subject on day 1 of the second dosing cycle, wherein the C2D1 is about 60 mg; and
(c) the third dosing cycle comprises a single dose (C3D1) of mosunetuzumab administered to the subject on day 1 of the third dosing cycle, wherein the C3D1 is about 30 mg.

130. The method of embodiment 129, wherein the dosing regimen comprises one to fourteen additional dosing cycles each comprising an additional single dose of about 30 mg of mosunetuzumab.

131. The method of embodiment 130, wherein the dosing regimen comprises one to five additional dosing cycles.

132. The method of embodiment 131, wherein the dosing regimen comprises five additional dosing cycles.

133. The method of any one of embodiments 130-132, wherein each additional single dose of mosunetuzumab is administered to the subject on day 1 of each respective additional dosing cycle.

134. The method of any one of embodiments 113-133, wherein the subject is co-administered at least one additional therapeutic agent.

135. The method of embodiment 134, wherein the at least one additional therapeutic agent comprises a PD-1 axis binding antagonist.

136. The method of embodiment 135, wherein the PD-1 axis binding antagonist is selected from the group consisting of a PD-L1 binding antagonist, a PD-1 binding antagonist, and a PD-L2 binding antagonist.

137. The method of embodiment 136, wherein the PD-1 axis binding antagonist is a PD-L1 binding antagonist.

138. The method of embodiment 137, wherein the PD-L1 binding antagonist is selected from the group consisting of atezolizumab (MPDL3280A), MDX-1105 (BMS-936559), and MED14736 (durvalumab).

139. The method of embodiment 136, wherein the PD-1 axis binding antagonist is a PD-1 binding antagonist.

140. The method of embodiment 139, wherein the PD-1 binding antagonist is selected from the group consisting of MDX-1106 (nivolumab), MK-3475 (lambrolizumab), AMG 404, REGN2810 (cemiplimab), and AMP-224.

141. The method of embodiment 136, wherein the PD-1 axis binding antagonist is a PD-L2 binding antagonist.

142. The method of embodiment 141, wherein the PD-L2 binding antagonist is an antibody or an immunoadhesin.

143. The method of embodiment 134, wherein the at least one additional therapeutic agent comprises obinutuzumab, rituximab, a corticosteroid, or tocilizumab.

144. The method of embodiment 134, wherein the at least one additional therapeutic agent comprises an ADC.

145. The method of embodiment 144, wherein the ADC is an anti-CD79b ADC.

146. The method of embodiment 145, wherein the anti-CD79b ADC is polatuzumab vedotin.

147. The method of any one of embodiments 113-146, wherein the pharmaceutical composition is administered intravenously.

148. The method of any one of embodiments 113-147, wherein the subject is a human.

149. Use of the pharmaceutical composition of any one of embodiments 1-80 in the manufacture of a medicament for treating or delaying the progression of a cancer in a subject in need thereof.

150. Use of the pharmaceutical composition of any one of embodiments 1-80 in the manufacture of a medicament for enhancing immune function in a subject having a cancer.

151. Use of the pharmaceutical composition of any one of embodiments 1-80 for treating or delaying the progression of a cancer in a subject in need thereof.

152. Use of the pharmaceutical composition of any one of embodiments 1-80 for enhancing immune function in a subject having a cancer.

153. The use of any one of embodiments 149-152, wherein the cancer is an NHL selected from the group consisting of CLL, B cell lymphoma, splenic diffuse red pulp small B cell lymphoma, B cell lymphoma with features intermediate between diffuse large B cell lymphoma and Burkitt lymphoma, B cell lymphoma with features intermediate between diffuse large B cell lymphoma and classical Hodgkin lymphoma, DLBCL, GCB DLBCL, ABC DLBCL, primary cutaneous follicle center lymphoma, T-cell/histiocyte rich large B cell lymphoma, primary DLBCL of the central nervous system, primary cutaneous DLBCL (leg type), EBV-positive DLBCL of the elderly, DLBCL associated with chronic inflammation, primary mediastinal (thymic) large B cell lymphoma, intravascular large B cell lymphoma, ALK-positive large B cell lymphoma, large B cell lymphoma arising in HHV8-associated multicentric Castleman disease, B cell leukemia, FL, MCL, AML, MZL, SLL, LL, WM, CNSL, BL, B cell prolymphocytic leukemia, splenic marginal zone lymphoma, hairy cell leukemia, splenic lymphoma/leukemia, hairy cell leukemia variant, α heavy chain disease, γ heavy chain disease, μ heavy chain disease, plasma cell myeloma, solitary plasmacytoma of bone, extraosseous plasmacytoma, MALT lymphoma, nodal marginal zone lymphoma, pediatric nodal marginal zone lymphoma, pediatric follicular lymphoma, lymphomatoid granulomatosis, plasmablastic lymphoma, and primary effusion lymphoma.

154. The use of embodiment 153, wherein the NHL is GCB DLBCL, ABC DLBCL, FL, MCL, AML, CLL, MZL, SLL, LL, WM, CNSL, or BL.

155. The use of embodiment 154, wherein the NHL is FL.

156. The use of embodiment 155, wherein the FL is relapsed and/or refractory (R/R).

157. The use of embodiment 156, wherein the subject having the R/R FL has relapsed after or is refractory to at least two prior systemic therapies.

158. The use of embodiment 157, wherein the subject has received prior systemic therapy comprising an anti-CD20 monoclonal antibody.

159. The use of embodiment 157 or 158, wherein the subject has received prior systemic therapy comprising an alkylating agent.

160. The use of any one of embodiments 149-159, wherein mosunetuzumab is formulated for administration to the subject at a dose from about 0.1 mg to about 100 mg.

161. The use of embodiment 160, wherein mosunetuzumab is formulated for administration to the subject at a dose from about 1 mg to about 60 mg.

162. The use of embodiment 161, wherein mosunetuzumab is formulated for administration to the subject at a dose of about 1 mg, 2 mg, 6 mg, 9 mg, 13.5 mg, 20 mg, 30 mg, or 60 mg.

163. The use of embodiment 162, wherein mosunetuzumab is formulated for administration to the subject at a dose of about 1 mg, 2 mg, 30 mg, or 60 mg.

164. The use of any one of embodiments 149-163, wherein the pharmaceutical composition is formulated for administration to the subject after dilution with a normal saline solution comprising 0.45% or 0.9% (w/v) NaCl.

165. The use of embodiment 164, wherein after dilution with the normal saline solution, the concentration of mosunetuzumab is from about 0.01 mg/ml to about 0.3 mg/ml.

166. The use of embodiment 165, wherein after dilution with the normal saline solution, the concentration of mosunetuzumab is about 0.01 mg/ml, about 0.02 mg/ml, about 0.04 mg/ml, about 0.12 mg/ml, about 0.24 mg/ml, or about 0.3 mg/ml.

167. The use of any one of embodiments 149-166, wherein the subject is to be co-administered at least one additional therapeutic agent.

168. The use of embodiment 167, wherein the at least one additional therapeutic agent comprises a PD-1 axis binding antagonist.

169. The use of embodiment 168, wherein the PD-1 axis binding antagonist is selected from the group consisting of a PD-L1 binding antagonist, a PD-1 binding antagonist, and a PD-L2 binding antagonist.

170. The use of embodiment 169, wherein the PD-1 axis binding antagonist is a PD-L1 binding antagonist.

171. The use of embodiment 170, wherein the PD-L1 binding antagonist is selected from the group consisting of atezolizumab (MPDL3280A), MDX-1105 (BMS-936559), and MED14736 (durvalumab).

172. The use of embodiment 169, wherein the PD-1 axis binding antagonist is a PD-1 binding antagonist.

173. The use of embodiment 172, wherein the PD-1 binding antagonist is selected from the group consisting of MDX-1106 (nivolumab), MK-3475 (lambrolizumab), AMG 404, REGN2810 (cemiplimab), and AMP-224.

174. The use of embodiment 169, wherein the PD-1 axis binding antagonist is a PD-L2 binding antagonist.

175. The use of embodiment 174, wherein the PD-L2 binding antagonist is an antibody or an immunoadhesin.

176. The use of embodiment 167, wherein the at least one additional therapeutic agent comprises obinutuzumab, rituximab, a corticosteroid, or tocilizumab.

177. The use of embodiment 167, wherein the at least one additional therapeutic agent comprises an ADC.

178. The use of embodiment 177, wherein the ADC is an anti-CD79b ADC.

179. The use of embodiment 178, wherein the anti-CD79b ADC is polatuzumab vedotin.

180. The use of any one of embodiments 149-179, wherein the pharmaceutical composition is to be administered intravenously.

181. The use of any one of embodiments 149-180, wherein the subject is a human.

182. The pharmaceutical composition for use of any one of embodiments 82-97 or the use of any one of embodiments 149-166, wherein mosunetuzumab is to be administered to the subject in a dosing regimen comprising at least three 21-day dosing cycles, wherein
(a) the first 21-day dosing cycle comprises a first dose (C1D1), a second dose (C1D2), and a third dose (C1D3) of mosunetuzumab to be administered to the subject on days 1, 8, and 15, respectively, of the first dosing cycle, wherein the C1D1 is about 1 mg, the C1D2 is about 2 mg, and the C1D3 is about 60 mg;
(b) the second dosing cycle comprises a single dose (C2D1) of mosunetuzumab to be administered to the subject on day 1 of the second dosing cycle, wherein the C2D1 is about 60 mg; and
(c) the third dosing cycle comprises a single dose (C3D1) of mosunetuzumab to be administered to the subject on day 1 of the third dosing cycle, wherein the C3D1 is about 30 mg.

183. The pharmaceutical composition for use or use of embodiment 182, wherein the dosing regimen comprises one to fourteen additional dosing cycles each comprising an additional single dose of about 30 mg of mosunetuzumab.

184. The pharmaceutical composition for use or use of embodiment 183, wherein the dosing regimen comprises one to five additional dosing cycles.

185. The pharmaceutical composition for use or use of embodiment 184, wherein the dosing regimen comprises five additional dosing cycles.

186. The pharmaceutical composition for use or use of any one of embodiments 182-185, wherein each additional single dose of mosunetuzumab is to be administered to the subject on day 1 of each respective additional dosing cycle.

187. The pharmaceutical composition for use or use of any one of embodiments 182-186, wherein the pharmaceutical composition is to be administered intravenously.

188. The pharmaceutical composition for use or use of any one of embodiments 182-187, wherein the subject is human.

Other Embodiments

Although the foregoing disclosure has been described in some detail by way of illustration and example for purposes of clarity of understanding, the descriptions and examples should not be construed as limiting the scope of the disclosure. The disclosures of all patent and scientific literature cited herein are expressly incorporated in their entirety by reference.

What is claimed is:

1. A pharmaceutical composition comprising about 1 mg/ml mosunetuzumab, about 10 mM L-histidine, about 240 mM sucrose, about 0.06% (w/v) PS20, and about 10 mM methionine, wherein the pharmaceutical composition has a pH of about 5.8.

2. The pharmaceutical composition of claim 1, wherein the pharmaceutical composition is in a unit dosage form.

3. The pharmaceutical composition of claim 1, wherein mosunetuzumab has a methionine at position 257 of the Fc region (EU numbering), and wherein oxidation of the methionine at position 257 of the Fc region is less than about 10% over two weeks at 40° C.

4. The pharmaceutical composition of claim 2, wherein the unit dosage form is a liquid formulation for dilution.

5. The pharmaceutical composition of claim 4, wherein the liquid formulation for dilution is supplied in a container having a volume of about 50 ml.

6. The pharmaceutical composition of claim 1, wherein the pharmaceutical composition:
   (a) has a shelf-life of at least 36 months when stored at 5° C.±3° C. and protected from light;
   (b) is stable through one or more freeze-thaw cycles;
   (c) is stable for about two weeks or longer at about 25° C.; or
   (d) is stable for about 48 months or longer at −20° C.

7. The pharmaceutical composition of claim 6, wherein stability is assessed by size-exclusion high-performance liquid chromatography (SE-HPLC) or by non-reduced capillary electrophoresis sodium dodecyl sulfate (CE-SDS) assay.

8. The pharmaceutical composition of claim 7, wherein:
   (a) the pharmaceutical composition is determined to be stable if the pharmaceutical composition maintains a purity that is changed by less than 5% as measured by SE-H PLC;
   (b) the pharmaceutical composition has a purity of about 85% or higher as assessed by SE-HPLC;
   (c) the purity of the pharmaceutical composition as assessed by SE-HPLC is maintained about the same for about 36 months or longer at about 5° C.;
   (d) the pharmaceutical composition is determined to be stable if the pharmaceutical composition maintains a purity that is changed by less than 5% as measured by non-reduced CE-SDS assay;

(e) the pharmaceutical composition has a purity of about 75% or higher as assessed by non-reduced CE-SDS assay; or (f) the purity of the pharmaceutical composition as assessed by non-reduced CE-SDS assay is maintained for about 36 months or longer at about 5° C.

9. The pharmaceutical composition of claim 1, wherein the pharmaceutical composition is formulated for administration by infusion after dilution with a normal saline solution comprising 0.45% or 0.9% NaCl.

10. The pharmaceutical composition of claim 1, wherein the pharmaceutical composition further comprises histidine acetate.

11. The pharmaceutical composition of claim 1, wherein the pharmaceutical composition is formulated as a drug product (DP).

12. The pharmaceutical composition of claim 1, wherein the pharmaceutical composition is formulated for intravenous administration.

13. The pharmaceutical composition of claim 12, wherein the pharmaceutical composition is formulated for administration by infusion.

14. The pharmaceutical composition of claim 1, wherein the pharmaceutical composition does not contain a preservative.

15. The pharmaceutical composition of claim 4, wherein the volume of the liquid formulation for dilution is between 20-40 ml.

16. The pharmaceutical composition of claim 1, wherein the pharmaceutical composition comprises no more than 1,000 particles having a diameter $\geq 2$ μm per ml as detected by high accuracy liquid particle counting (HIAC).

17. The pharmaceutical composition of claim 4, wherein the volume of the liquid formulation for dilution is between 0.2-2 ml.

* * * * *